(12) United States Patent
Hirano et al.

(10) Patent No.: US 7,001,917 B2
(45) Date of Patent: Feb. 21, 2006

(54) PYRAZOLE COMPOUNDS AS ANTI-INFLAMMATORY AND ANALGESIC AGENTS

(75) Inventors: Misato Hirano, Aichi-ken (JP); Kazunari Nakao, Aichi-ken (JP); Seiji Nukui, San Diego, CA (US); Tatsuya Yamagishi, Aichi-ken (JP)

(73) Assignee: Warner Lambert Company LLC, Morris Plains, NJ (US)

( * ) Notice: Subject to any disclaimer, the term of this patent is extended or adjusted under 35 U.S.C. 154(b) by 0 days.

(21) Appl. No.: 10/409,881

(22) Filed: Apr. 9, 2003

(65) Prior Publication Data
US 2004/0019045 A1 Jan. 29, 2004

Related U.S. Application Data
(60) Provisional application No. 60/372,047, filed on Apr. 12, 2002.

(51) Int. Cl.
*A61K 31/415* (2006.01)
*C07D 231/10* (2006.01)
*A61P 29/00* (2006.01)

(52) U.S. Cl. .................................... 514/406; 548/375.1
(58) Field of Classification Search .............. 548/375.1; 514/406
See application file for complete search history.

(56) References Cited

FOREIGN PATENT DOCUMENTS

| WO | WO 00/64888 | 12/1998 |
|---|---|---|
| WO | WO 99/19300 | 4/1999 |
| WO | WO 99/47497 | 9/1999 |
| WO | WO 98/56377 | 11/2000 |
| WO | WO 02/32900 | 4/2002 |

*Primary Examiner*—Taofiq Solola
*Assistant Examiner*—Robert Shiao
(74) *Attorney, Agent, or Firm*—Suzanne M. Harvey; David R. Kurlandsky; Charles W. Ashbrook

(57) ABSTRACT

This invention provides a compound of the formula (I):

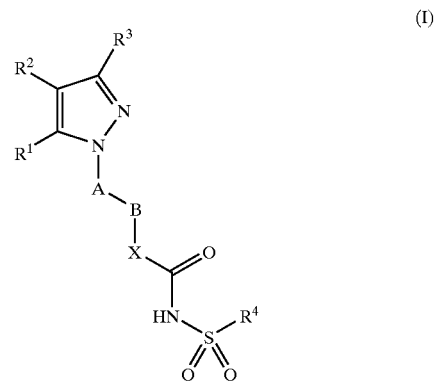

wherein:
$R^1$ represents a hydrogen atom, an alkyl group, etc.; $R^2$ represents a hydrogen atom, a halogen atom, etc.; $R^3$ represents an alkyl group, etc.; $R^4$ represents an aryl group, etc.;
A represents an $aryl^1$, etc; B represents an alkylene etc.; X represents NH, etc.;
or a pharmaceutically acceptable ester of such compound, and pharmaceutically acceptable salts thereof.

These compounds are useful for the treatment of medical conditions mediated by prostaglandin such as pain, fever or inflammation, etc. This invention also provides a pharmaceutical composition comprising the above compound.

13 Claims, No Drawings

PYRAZOLE COMPOUNDS AS ANTI-INFLAMMATORY AND ANALGESIC AGENTS

This application claims benefit of U.S. Provisional Application No. 60/372,047 filed Apr. 12, 2002.

TECHNICAL FIELD

This invention relates to pyrazole compounds, and their pharmaceutically acceptable salts, pharmaceutical compositions containing them, and their medical uses. The compounds of this invention have activity as prostaglandin $E_2$ receptor antagonists, and these are useful in the treatment or alleviation of pain and inflammation and other inflammation-associated disorders, such as arthritis, and intreating or preventing disorders or medical conditions selected from pain, inflammatory diseases and the like.

BACKGROUND ART

Prostaglandins are mediators of pain, fever and other symptoms associated with inflammation. Prostaglandin $E_2$ ($PGE_2$) is the predominant eicosanoid detected in inflammation conditions. In addition, it is also involved in various physiological and/or pathological conditions such as hyperalgesia, uterine contraction, digestive peristalsis, awakeness, suppression of gastric acid secretion, blood pressure, platelet function, bone metabolism, angiogenesis or the like.

Four $PGE_2$ receptor subtypes ($EP_1$, $EP_2$, $EP_3$ and $EP_4$) displaying different pharmacological properties have been cloned. The $EP_4$ subtype, a Gs-coupled receptor, stimulates cAMP production, and is distributed in a wide variety of tissue suggesting a major role in $PGE_2$-mediated biological events.

WO99/47497 discloses carboxylic acids and acylsulfonamides compounds as prostaglandin-receptor antagonists. Although heteroaryl compounds synthesized are described in WO00/64888, it relates to peroxisome proliferataor-activated receptors (PPAR) ligands. Further, pyrazole compounds synthesized for different uses are described in WO98/56377, such as treatment of cytokine mediated diseases.

The invention addresses the problem of providing $EP_4$ receptor modulators (e.g., agonists and antagonists) which have improved $EP_4$ receptor modulating activities (e.g., angonist or antagonist activities).

BRIEF DISCLOSURE OF THE INVENTION

The present invention provides a compound of the following formula (I):

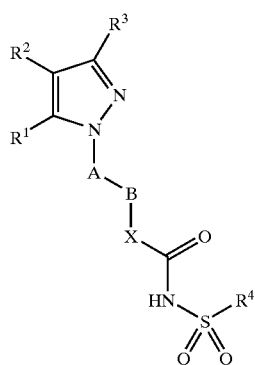

(I)

wherein:
$R^1$ represents a hydrogen atom, an alkyl group having from 1 to 6 carbon atoms, an amino group, mono- or di-alkylamino groups, the alkyl group(s) having from 1 to 6 carbon atoms, an aryl group or a heteroaryl group;

$R^2$ represents a hydrogen atom, a halogen atom, an alkyl group having from 1 to 6 carbon atoms, a cycloalkyl group having from 3 to 8 carbon atoms, a cycloalkenyl group having from 3 to 10 carbon atoms, an aralkyl group, an aryl group, or a heteroaryl group;

$R^3$ represents an alkyl group having from 1 to 6 carbon atoms, a haloalkyl group having from 1 to 6 carbon atoms, a hydroxyalkyl group having from 1 to 6 carbon atoms, an aryl group or a heteroaryl group;

$R^4$ represents an aryl group, or a heteroaryl group;

A represents an aryl$^1$ group having from 6 to 10 carbon atoms or an heteroaryl$^1$ group having from 5 to 7 atoms, wherein 1 to 4 of said atoms of the heteroaryl$^1$ group are independently selected from the group consisting of sulfur atoms, oxygen atoms and nitrogen atoms;

B represents an alkylene group having from 1 to 6 carbon atoms;

X represents NH, N[$(C_1-C_6)$alkyl], oxygen or sulfur;

said aryl groups have 6 to 14 carbon atoms;

said heteroaryl groups are 5- to 14-membered aromatic heterocyclic groups containing from 1 to 4 heteroatoms selected from the group consisting of sulfur atoms, oxygen atoms and nitrogen atoms;

said aryl groups and said heteroaryl groups are unsubstituted or are substituted by at least one substituent selected from the group consisting of substituents α, defined below;

said aralkyl groups are alkyl groups having from 1 to 6 carbon atoms and which are substituted by at least one aryl group as defined above;

said substituents α are selected from the group consisting of alkyl group having from 1 to 6 carbon atoms, an aryl group defined above, a heteroaryl group defined above, hydroxy group, halogen atoms, alkoxy group having from 1 to 6 carbon atoms, alkylthio group having from 1 to 6 carbon atoms, alkanoyl group having from 1 to 6 carbon atoms, alkanoylamino group having from 1 to 6 carbon atoms, alkanoylaminoalkyl group having from 1 to 6 carbon atoms in the alkanoyl and alkyl part, amino group, mono- or di-alkylamino group, the alkyl group(s) having from 1 to 6 carbon atoms, haloalkyl group having from 1 to 6 carbon atoms, haloalkoxy group having from 1 to 6 carbon atoms, carbamoyl group, cyano group, a hydroxyalkyl group having from 1 to 6 carbon atoms, alkylsufinyl group having from 1 to 6 carbon atoms, alkylsufonyl group having from 1 to 6 carbon atoms, aminoalkoxy group having from 1 to 6 carbon atoms, mono- or di-alkylaminoalkoxy group, the alkyl group(s) having from 1 to 6 carbon atoms in the alkyl and alkoxy part, alkylsulfonylamino group having from 1 to 6 carbon atoms and aminosulfonyl group;

with the proviso that said aryl group and said heteroaryl group in said substituents α are not substituted by an aryl group or an heteroaryl group: or a pharmaceutically acceptable ester of such compound, or a pharmaceutically acceptable salt thereof.

The pyrazole compounds of this invention have an antagonistic action towards prostaglandin and are thus useful in therapeutics, particularly for the treatment of a disorder or condition selected from the group consisting of pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures or bone fracture, immune and autoimmune diseases such as systemic lupus erythematosus; AIDS (acquired immuno deficiency syndrome), gastrointestinal cancers such as colon cancer; cellular neoplastic transformations or metastic tumor growth; diabetic retinopathy, tumor angiogenesis; prostanoid-induced smooth muscle contraction associated with dysmenorrhea, premature labor, allergic rhinitis, atopic dermatitis, asthma or eosinophil related disorders, hyperimmunoglobulinaemia, Castleman's disease, myeloma; Alzheimer's disease, sleep disorders, endocrine disturbance; glaucoma; bone loss; osteoporosis; promotion of bone formation; Paget's disease: cytoprotection in peptic ulcers, gastritis, regional enteritis, ulcerative colitis, diverticulitis or other gastrointestinal lesions; GI bleeding and patients undergoing chemotherapy; coagulation disorders selected from hypoprothrombinemia, haemophilia and other bleeding problems; kidney disease;

thrombosis; occlusive vascular disease; presurgery; and anti-coagulation, or the like in mammalian, especially humans.

The present invention provides a pharmaceutical composition for the treatment of a disorder or condition mediated by prostaglandin, in a mammalian including a human, which comprises administering to said subject a therapeutically effective amount of a
compound of formula (I)

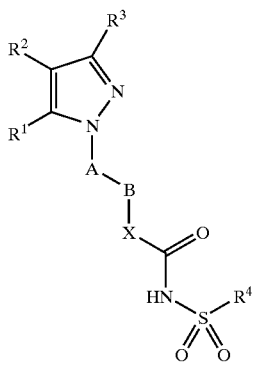

wherein:
$R^1$ represents a hydrogen atom, an alkyl group having from 1 to 6 carbon atoms, an amino group, mono- or di-alkylamino groups, the alkyl group(s) having from 1 to 6 carbon atoms, an aryl group or a heteroaryl group;
$R^2$ represents a hydrogen atom, a halogen atom, an alkyl group having from 1 to 6 carbon atoms, a cycloalkyl group having from 3 to 8 carbon atoms, a cycloalkenyl group having from 3 to 10 carbon atoms, an aralkyl group, an aryl group, or a heteroaryl group;
$R^3$ represents an alkyl group having from 1 to 6 carbon atoms, a haloalkyl group having from 1 to 6 carbon atoms, a hydroxyalkyl group having from 1 to 6 carbon atoms, an aryl group or a heteroaryl group;
$R^4$ represents an aryl group, or a heteroaryl group;
A represents an $aryl^1$ group having from 6 to 10 carbon atoms or an $heteroaryl^1$ group having from 5 to 7 atoms, wherein 1 to 4 of said atoms of the $heteroaryl^1$ group are independently selected from the group consisting of sulfur atoms, oxygen atoms and nitrogen atoms;
B represents an alkylene group having from 1 to 6 carbon atoms;
X represents NH, $N[(C_1-C_6)alkyl]$, oxygen or sulfur;
said aryl groups have 6 to 14 carbon atoms;

said heteroaryl groups are 5- to 14-membered aromatic heterocyclic groups containing from 1 to 4 heteroatoms selected from the group consisting of sulfur atoms, oxygen atoms and nitrogen atoms;
said aryl groups and said heteroaryl groups are unsubstituted or are substituted by at least one substituent selected from the group consisting of substituents α, defined below;
said aralkyl groups are alkyl groups having from 1 to 6 carbon atoms and which are substituted by at least one aryl group as defined above;
said substituents α are selected from the group consisting of alkyl group having from 1 to 6 carbon atoms, an aryl group defined above, a heteroaryl group defined above, hydroxy group, halogen atoms, alkoxy group having from 1 to 6 carbon atoms, alkylthio group having from 1 to 6 carbon atoms, alkanoyl group having from 1 to 6 carbon atoms, alkanoylamino group having from 1 to 6 carbon atoms, alkanoylaminoalkyl group having from 1 to 6 carbon atoms in the alkanoyl and alkyl part, amino group, mono- or di-alkylamino group having from 1 to 6 carbon atoms, haloalkyl group having from 1 to 6 carbon atoms, haloalkoxy group having from 1 to 6 carbon atoms, carbamoyl group, cyano group, a hydroxyalkyl group having from 1 to 6 carbon atoms, alkylsufinyl group having from 1 to 6 carbon atoms, alkylsufonyl group having from 1 to 6 carbon atoms, aminoalkoxy group having from 1 to 6 carbon atoms, mono- or di-alkylaminoalkoxy group, the alkyl group(s) having from 1 to 6 carbon atoms in the alkyl and alkoxy part, alkylsulfonylamino group having from 1 to 6 carbon atoms and aminosulfonyl group;
with the proviso that said aryl group and said heteroaryl group in said substituents α are not substituted by an aryl group or an heteroaryl group: or ester or salt thereof and a pharmaceutically acceptable diluent or carrier. Further, the present invention also provides a pharmaceutical composition for the treatment of a disorder or condition selected from the group consisting of pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures, bone fracture, immune and autoimmune diseases such as systemic lupus erythematosus; AIDS (acquired immuno deficiency syndrome), gastrointestinal cancers such as colon cancer; cellular neoplastic transformations or metastic tumor growth;

diabetic retinopathy, tumor angiogenesis; prostanoid-induced smooth muscle contraction associated with dysmenorrhea, premature labor, allergic rhinitis, atopic dermatitis, asthma or eosinophil related disorders, hyperimmunoglobulinaemia, Castleman's disease, myeloma; Alzheimer's disease, sleep disorders, endocrine disturbance; glaucoma; bone loss; osteoporosis; promotion of bone formation;
Paget's disease: cytoprotection in peptic ulcers, gastritis, regional enteritis, ulcerative colitis, diverticulitis or other gastrointestinal lesions; GI bleeding and patients undergoing chemotherapy; coagulation disorders selected from hypoprothrombinemia, haemophilia and other bleeding problems; kidney disease;
thrombosis; occlusive vascular disease; presurgery; and anti-coagulation, or the like, which comprises a therapeutically effective amount of the aryl or heteroaryl fused imidazole compound of formula (I) or its pharmaceutically acceptable ester or salt together with a pharmaceutically acceptable diluent or carrier.

Also, the present invention provides a method for the treatment of a disorder or condition mediated by prostaglandin, in a mammalian including a human, which comprises administering to said subject a therapeutically effective amount of a compound of formula (I)

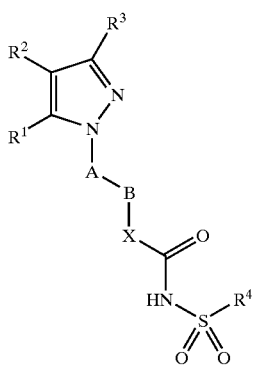

(I)

wherein:
$R^1$ represents a hydrogen atom, an alkyl group having from 1 to 6 carbon atoms, an amino group, mono- or di-alkylamino groups, the alkyl group(s) having from 1 to 6 carbon atoms, an aryl group or a heteroaryl group;
$R^2$ represents a hydrogen atom, a halogen atom, an alkyl group having from 1 to 6 carbon atoms, a cycloalkyl group having from 3 to 8 carbon atoms, a cycloalkenyl group having from 3 to 10 carbon atoms, an aralkyl group, an aryl group, or a heteroaryl group;
$R^3$ represents an alkyl group having from 1 to 6 carbon atoms, a haloalkyl group having from 1 to 6 carbon atoms, a hydroxyalkyl group having from 1 to 6 carbon atoms, an aryl group or a heteroaryl group;
$R^4$ represents an aryl group, or a heteroaryl group;
A represents an $aryl^1$ group having from 6 to 10 carbon atoms or an $heteroaryl^1$ group having from 5 to 7 atoms, wherein 1 to 4 of said atoms of the $heteroaryl^1$ group are independently selected from the group consisting of sulfur atoms, oxygen atoms and nitrogen atoms;
B represents an alkylene group having from 1 to 6 carbon atoms;
X represents NH, $N[(C_1-C_6)alkyl]$, oxygen or sulfur;
said aryl groups have 6 to 14 carbon atoms;
said heteroaryl groups are 5- to 14-membered aromatic heterocyclic groups containing from 1 to 4 heteroatoms selected from the group consisting of sulfur atoms, oxygen atoms and nitrogen atoms;
said aryl groups and said heteroaryl groups are unsubstituted or are substituted by at least one substituent selected from the group consisting of substituents α, defined below;
said aralkyl groups are alkyl groups having from 1 to 6 carbon atoms and which are substituted by at least one aryl group as defined above;
said substituents α are selected from the group consisting of alkyl group having from 1 to 6 carbon atoms, an aryl group defined above, a heteroaryl group defined above, hydroxy group, halogen atoms, alkoxy group having from 1 to 6 carbon atoms, alkylthio group having from 1 to 6 carbon atoms, alkanoyl group having from 1 to 6 carbon atoms, alkanoylamino group having from 1 to 6 carbon atoms, alkanoylaminoalkyl group having from 1 to 6 carbon atoms in the alkanoyl and alkyl part, amino group, mono- or di-alkylamino group having from 1 to 6 carbon atoms, haloalkyl group having from 1 to 6 carbon atoms, haloalkoxy group having from 1 to 6 carbon atoms, carbamoyl group, cyano group, a hydroxyalkyl group having from 1 to 6 carbon atoms, alkylsufinyl group having from 1 to 6 carbon atoms, alkylsufonyl group having from 1 to 6 carbon atoms, aminoalkoxy group having from 1 to 6 carbon atoms, mono- or di-alkylaminoalkoxy group, the alkyl group(s) having from 1 to 6 carbon atoms in the alkyl and alkoxy part, alkylsulfonylamino group having from 1 to 6 carbon atoms and aminosulfonyl group; with the proviso that said aryl group and said heteroaryl group in said substituents α are not substituted by an aryl group or an heteroaryl group: or a pharmaceutically acceptable ester of such compound, or a pharmaceutically acceptable salt thereof.

Further, the present invention provides a method for the treatment of pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures, bone fracture, immune and autoimmune diseases such as systemic lupus erythematosus; AIDS, gastrointestinal cancers such as colon cancer; cellular neoplastic transformations or metastic tumor growth; diabetic retinopathy, tumor angiogenesis;
prostanoid-induced smooth muscle contraction associated with dysmenorrhea, premature labor, allergic rhinitis, atopic dermatitis, asthma or eosinophil related disorders, hyperimmunoglobulinaemia, Castleman's disease, myeloma; Alzheimer's disease, sleep disorders, endocrine disturbance; glaucoma; bone loss; osteoporosis; promotion of bone formation; Paget's disease: cytoprotection in peptic ulcers, gastritis, regional enteritis, ulcerative colitis, diverticulitis or other gastrointestinal lesions; GI bleeding and patients undergoing chemotherapy; coagulation disorders selected from hypoprothrombinemia, haemophilia and other bleeding problems; kidney disease; thrombosis; occlusive vascular disease;
presurgery; and anti-coagulation or the like, in a mammalian subject, which comprises administering to said subject a therapeutically effective amount of a compound of formula (I)

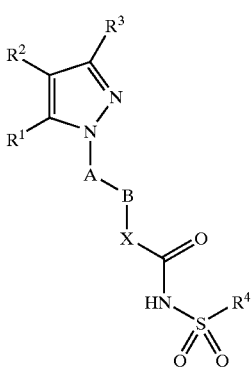

(I)

wherein:
$R^1$ represents a hydrogen atom, an alkyl group having from 1 to 6 carbon atoms, an amino group, mono- or di-alkylamino groups, the alkyl group(s) having from 1 to 6 carbon atoms, an aryl group or a heteroaryl group;

$R^2$ represents a hydrogen atom, a halogen atom, an alkyl group having from 1 to 6 carbon atoms, a cycloalkyl group having from 3 to 8 carbon atoms, a cycloalkenyl group having from 3 to 10 carbon atoms, an aralkyl group, an aryl group, or a heteroaryl group;

$R^3$ represents an alkyl group having from 1 to 6 carbon atoms, a haloalkyl group having from 1 to 6 carbon atoms, a hydroxyalkyl group having from 1 to 6 carbon atoms, an aryl group or a heteroaryl group;

$R^4$ represents an aryl group, or a heteroaryl group;

A represents an aryl$^1$ group having from 6 to 10 carbon atoms or an heteroaryl$^1$ group having from 5 to 7 atoms, wherein 1 to 4 of said atoms of the heteroaryl$^1$ group are independently selected from the group consisting of sulfur atoms, oxygen atoms and nitrogen atoms;

B represents an alkylene group having from 1 to 6 carbon atoms;

X represents NH, N[($C_1$–$C_6$)alkyl], oxygen or sulfur;

said aryl groups have 6 to 14 carbon atoms;

said heteroaryl groups are 5- to 14-membered aromatic heterocyclic groups containing from 1 to 4 heteroatoms selected from the group consisting of sulfur atoms, oxygen atoms and nitrogen atoms;

said aryl groups and said heteroaryl groups are unsubstituted or are substituted by at least one substituent selected from the group consisting of substituents α, defined below;

said aralkyl groups are alkyl groups having from 1 to 6 carbon atoms and which are substituted by at least one aryl group as defined above;

said substituents α are selected from the group consisting of alkyl group having from 1 to 6 carbon atoms, an aryl group defined above, a heteroaryl group defined above, hydroxy group, halogen atoms, alkoxy group having from 1 to 6 carbon atoms, alkylthio group having from 1 to 6 carbon atoms, alkanoyl group having from 1 to 6 carbon atoms, alkanoylamino group having from 1 to 6 carbon atoms, alkanoylaminoalkyl group having from 1 to 6 carbon atoms in the alkanoyl and alkyl part, amino group, mono- or di-alkylamino group having from 1 to 6 carbon atoms, haloalkyl group having from 1 to 6 carbon atoms, haloalkoxy group having from 1 to 6 carbon atoms, carbamoyl group, cyano group, a hydroxyalkyl group having from 1 to 6 carbon atoms, alkylsufinyl group having from 1 to 6 carbon atoms, alkylsufonyl group having from 1 to 6 carbon atoms, aminoalkoxy group having from 1 to 6 carbon atoms, mono- or di-alkylaminoalkoxy group, the alkyl group(s) having from 1 to 6 carbon atoms in the alkyl and alkoxy part, alkylsulfonylamino group having from 1 to 6 carbon atoms and aminosulfonyl group; with the proviso that said aryl group and said heteroaryl group in said substituents α are not substituted by an aryl group or an heteroaryl group: or a pharmaceutically acceptable ester of such compound, or a pharmaceutically acceptable salt thereof.

Also, the present invention provides a pharmaceutical formulation comprising a compound of formula (I), a pharmaceutically acceptable diluent or carrier and, optionally, one or more other pharmacologically active ingredients.

Also, the present invention provides combination, including a pharmaceutical formulation, comprising a compound of formula (I), or an ester or salt thereof and, one or more other pharmacologically active ingredient(s) selected from a COX-2 selective, COX-1 selective or non-selective NSAID (nonsteroidal anti-inflammatory drug), opioid, anticonvulsant, antidepressant, local anesthetic, disease-modifying anti-rheumatoid drug, or steroid.

DETAILED DESCRIPTION OF THE INVENTION

As used herein, the term "halogen" means fluoro, chloro, bromo and iodo, preferably fluoro or chloro.

As used herein, the term "alkyl" means straight or branched chain saturated radicals, including, but not limited to methyl, ethyl, n-propyl, isopropyl, n-butyl, iso-butyl, secondary-butyl, tertiary-butyl.

As used herein, the term "alkoxy" means alkyl-O—, including, but not limited to methoxy, ethoxy, n-propoxy, isopropoxy, n-butoxy, iso-butoxy, secondary-butoxy, tertiary-butoxy.

As used herein, the term "alkanoyl" means a group having carbonyl such as R'—C(O)— wherein R' is $C_{1-6}$ alkyl, phenyl or $C_{3-6}$ cycloalkyl, including, but not limited to formyl, acetyl, ethyl-C(O)—, n-propyl-C(O)—, isopropyl-C(O)—, n-butyl-C(O)—, iso-butyl-C(O)—, secondary-butyl-C(O)—, tertiary-butyl-C(O)—, cyclopropyl-C(O)—, cyclobutyl-C(O)—, cyclopentyl-C(O)—, cyclohexyl-C(O)—, cycloheptyl-C(O)—, and the like.

As used herein, the term "aryl" means a monocyclic or bicyclic aromatic carbocyclic ring of 6 to 14 carbon atoms, preferably 6 to 10 carbon atoms including, but not limited to, phenyl, naphthyl, indanyl, preferably phenyl and naphthyl.

As used herein, the term "aryl$^1$" means a divalent aromatic hydrocarbon ring having from 6 to 14 carbon atoms such as phenylene and naphthylene, preferably a p-phenylene group.

As used herein, the term "heteroaryl$^1$" means a divalent heteroaromatic ring having from 5 to 7 ring atoms containing from 1 to 4 heteroatoms selected from the group consisting of sulfur atoms, oxygen atoms and nitrogen atoms, such as pyridylene pyrazolylene, furylene, thienylene, oxazolylene, tetrazolylene, thiazolylene, imidazolylene, thiadiazolylene, pyrimidinylene, pyrrolylene, thiophenylene, pyrazinylene, pyridazinylene, isooxazolylene, isothiazolylene, triazolylene, furazanylene and the like, preferably a pyridylene group.

As used herein, the term "aralkyl" means an alkyl radical which is substituted by an aryl group as defined above, e.g. benzyl.

The term "alkylene", as used herein, means saturated hydrocarbon (straight chain or branched) wherein a hydrogen atom is removed from each of the terminal carbons such as methylene, ethylene, methylethylene, propylene, butylene, pentylene, hexylene and the like.

The term "cycloalkyl", as used herein, means a saturated carbocyclic radical ring of 3 to 8 carbon atoms, including, but not limited to, cyclopropyl, cyclobutyl, cyclohexyl, cycloheptyl, cyclooctyl, cyclononyl, cyclodecyl and the like.

The term "cycloalkenyl", as used herein, means a unsaturated carbocyclic radical ring of 3 to 10 carbon atoms having at least one double bond including, but not limited to, cyclopropenyl, cyclobutenyl, cyclohexenyl, cycloheptenyl, cyclooctenyl, cyclononenyl, cyclodecenyl and the like.

The term "haloalkyl", as used herein, means an alkyl radical which is substituted by halogenatoms as defined above including, but not limited to, fluoromethyl, difluoromethyl, trifluoromethyl, 2-fluoroethyl, 2,2-difluoroethyl, 2,2,2-trifluoroethyl, 2,2,2-trichloroethyl, 3-fluoropropyl, 4-fluorobutyl, chloromethyl, trichloromethyl, iodomethyl and bromomethyl groups and the like.

The term "haloalkoxy", as used herein, means haloalkyl-O—, including, but not limited to, fluoromethoxy, difluoromethoxy, trifluoromethoxy, 2-fluoroethoxy, 2,2-difluoroethoxy, 2,2,2-trifluoroethoxy, 2,2,2-trichloroethoxy, 3-fluoropropoxy, 4-fluorobutoxy, chloromethoxy, trichloromethoxy, iodomethoxy and bromomethoxy groups and the like.

The term "heteroaryl" means a 5- to 14-membered aromatic heterocyclic ring which consists of from 1 to 4 heteroatoms independently selected from the group consisting of N, O and S, including, but not limited to, pyrazolyl, furyl, thienyl, oxazolyl, tetrazolyl, thiazolyl, imidazolyl, thiadiazolyl, pyridyl, pyrimidinyl, pyrrolyl, thiophenyl, pyrazinyl, pyridazinyl, isooxazolyl, isothiazolyl, triazolyl, furazanyl and the like.

Where the compounds of formula (I) contain hydroxy groups, they may form esters. Examples of such esters include esters with a hydroxy group and esters with a carboxy group. The ester residue may be an ordinary protecting group or a protecting group which can be cleaved in vivo by a biological method such as hydrolysis.

The term "ordinary protecting group" means a protecting group which can be cleaved by a chemical method such as hydrogenolysis, hydrolysis, electrolysis or photolysis.

The term "protecting group which can be cleaved in vivo by a biological method such as hydrolysis" means a protecting group which is cleaved in vivo by a biological method such as hydrolysis and forms a free acid or salt thereof. Whether a compound is such a derivative or not can be determined by administering it by intravenous injection to an experimental animal, such as a rat or mouse, and then studying the body fluids of the animal to determine whether or not the compound or a pharmaceutically acceptable salt thereof can be detected.

Preferred examples of such ordinary protecting groups for an ester of a hydroxy group include: lower aliphatic acyl groups, for example: alkanoyl groups, such as the formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl and henicosanoyl groups; halogenated alkylcarbonyl groups, such as the chloroacetyl, dichloroacetyl, trichloroacetyl, and trifluoroacetyl groups; alkoxyalkylcarbonyl groups, such as the methoxyacetyl group; and unsaturated alkylcarbonyl groups, such as the acryloyl, propioloyl, methacryloyl, crotonoyl, isocrotonoyl and (E)-2-methyl-2-butenoyl groups; more preferably, the lower aliphatic acyl groups having from 1 to 6 carbon atoms; aromatic acyl groups, for example: arylcarbonyl groups, such as the benzoyl, α-naphthoyl and β-naphthoyl groups; halogenated arylcarbonyl groups, such as the 2-bromobenzoyl and 4-chlorobenzoyol groups; lower alkylated arylcarbonyl groups, such as the 2,4,6-trimethylbenzoyl and 4-toluoyl groups; lower alkoxylated arylcarbonyl groups, such as the 4-anisoyl group; nitrated arylcarbonyl groups, such as the 4-nitrobenzoyl and 2-nitrobenzoyl groups; lower alkoxycarbonylated arylcarbonyl groups, such as the 2-(methoxycarbonyl)benzoyl group; and arylated arylcarbonyl groups, such as the 4-phenylbenzoyl group; alkoxycarbonyl groups, for example: lower alkoxycarbonyl groups, such as the methoxycarbonyl, ethoxycarbonyl, propoxycarbonyl, butoxycarbonyl, sec-butoxycarbonyl, t-butoxycarbonyl and isobutoxycarbonyl groups; and halogen- or tri(lower alkyl)silyl-substituted lower alkoxycarbonyl groups, such as the 2,2,2-trichloroethoxycarbonyl and 2-trimethylsilylethoxycarbonyl groups; tetrahydropyranyl or tetrahydrothiopyranyl groups, such as: tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl groups; tetrahydrofuranyl or tetrahydrothiofuranyl groups, such as: tetrahydrofuran-2-yl and tetrahydrothiofuran-2-yl groups; silyl groups, for example: tri(lower alkyl)silyl groups, such as the trimethylsilyl, triethylsilyl, isopropyldimethylsilyl, t-butyldimethylsilyl, methyldiisopropylsilyl, methyldi-t-butylsilyl and triisopropylsilyl groups; and tri(lower alkyl) silyl groups substituted by 1 or 2 aryl groups, such as the diphenylmethylsilyl, diphenylbutylsilyl, diphenylisopropylsilyl and phenyldiisopropylsilyl groups; alkoxymethyl groups, for example: lower alkoxymethyl groups, such as the methoxymethyl, 1,1-dimethyl-1-methoxymethyl, ethoxymethyl, propoxymethyl, isopropoxymethyl, butoxymethyl and t-butoxymethyl groups; lower alkoxylated lower alkoxymethyl groups, such as the 2-methoxyethoxymethyl group; and halo(lower alkoxy) methyl groups, such as the 2,2,2-trichloroethoxymethyl and bis(2-chloroethoxy)methyl groups; substituted ethyl groups, for example: lower alkoxylated ethyl groups, such as the 1-ethoxyethyl and 1-(isopropoxy)ethyl groups; and halogenated ethyl groups, such as the 2,2,2-trichloroethyl group; aralkyl groups, for example: lower alkyl groups substituted by from 1 to 3 aryl groups, such as the benzyl, α-naphthylmethyl, β-naphthylmethyl, diphenylmethyl, triphenylmethyl, α-naphthyldiphenylmethyl and 9-anthrylmethyl groups; and lower alkyl groups substituted by from 1 to 3 substituted aryl groups, where one or more of the aryl groups is substituted by one or more lower alkyl, lower alkoxy, nitro, halogen or cyano substituents, such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups; alkenyloxycarbonyl groups: such as the vinyloxycarbonyl and aryloxycarbonyl groups; and aralkyloxycarbonyl groups in which the aryl ring may be substituted by 1 or 2 lower alkoxy or nitro groups: such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

The term "protecting group", as used herein, means a hydroxy or amino protecting group which is selected from typical hydroxy or amino protecting groups described in Protective Groups in Organic Synthesis edited by T. W. Greene et al. (John Wiley & Sons, 1991);

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

Throughout this application, various publications are referenced by citation or number. The disclosures of these publications in their entireties are hereby incorporated by reference into this application.

In the compounds of formula (I),
$R^1$ represents preferably an alkyl group having from 1 to 6 carbon atoms, an amino group or an aryl group, more preferably an alkyl group having from 1 to 6 carbon atoms, an amino group or an unsubstituted aryl group having from 6 to 10 carbon atoms; more preferably an alkyl group having from 1 to 6 carbon atoms, an amino group or phenyl; more preferably an alkyl group having from 1 to 6 carbon atoms or an amino group.

In the compounds of formula (I), $R^2$ represents a hydrogen atom, a halogen atom, an alkyl group having from 1 to 6 carbon atoms, a cycloalkyl group having from 3 to 8 carbon atoms, an aralkyl group, an aryl group or a heteroaryl group, more preferably, a hydrogen atom, a halogen atom, an alkyl group having from 1 to 6 carbon atoms, a cycloalkyl group having from 3 to 8 carbon atoms, an aralkyl group, an aryl group or a heteroaryl group; said aryl groups and said heteroaryl groups are unsubstituted or are substituted by at least one substituent selected from the group consisting of substituents α, defined below; said substituents α are selected from the group consisting of alkyl groups having from 1 to 6 carbon atoms, hydroxy groups, halogen atoms, alkoxy groups having from 1 to 6 carbon atoms, alkanoylamino groups having from 1 to 6 carbon atoms, di-alkylamino groups, the alkyl group(s) having from 1 to 6 carbon atoms, haloalkyl groups having from 1 to 6 carbon atoms and carbamoyl groups, more preferably, a hydrogen atom, an alkyl group having from 1 to 6 carbon atoms, a cycloalkyl group having from 3 to 8 carbon atoms, an aryl group or a heteroaryl group; said aryl groups and said heteroaryl groups are unsubstituted or are substituted by at least one substituent selected from the group consisting of substituents α, defined below; said substituents α are selected from the group consisting of alkyl groups having from 1 to 6 carbon atoms, hydroxy groups, halogen atoms, alkoxy groups having from 1 to 6 carbon atoms, alkanoylamino groups having from 1 to 6 carbon atoms, di-alkylamino groups, the alkyl group(s) having from 1 to 6 carbon atoms, haloalkyl groups having from 1 to 6 carbon atoms and carbamoyl groups, more preferably, a hydrogen atom, an alkyl group having from 1 to 6 carbon atoms or an aryl group having from 6 to 10 carbon atoms; said aryl groups are unsubstituted or are substituted by at least one substituent selected from the group consisting of substituents α, defined below; said substituents α are selected from the group consisting of alkyl groups having from 1 to 6 carbon atoms, hydroxy groups, halogen atoms, alkoxy groups having from 1 to 6 carbon atoms, haloalkyl groups having from 1 to 6 carbon atoms and carbamoyl groups; more preferably, an alkyl group having from 1 to 6 carbon atoms, e.g. butyl, naphthyl, phenyl or phenyl substituted by at least one substituent selected from the group consisting of substituents α, defined below; said substituents α are selected from the group consisting of alkyl groups having from 1 to 6 carbon atoms, hydroxy groups, halogen atoms, alkoxy groups having from 1 to 6 carbon atoms, haloalkyl groups having from 1 to 6 carbon atoms, e.g. trifuluoromethyl, and carbamoyl groups; more preferably, an alkyl group having from 1 to 6 carbon atoms, e.g. butyl, phenyl or phenyl substituted by at least one substituent selected from the group consisting of substituents α, defined below; said substituents α are selected from the group consisting of alkyl groups having from 1 to 6 carbon atoms, e.g. methyl or ethyl, halogen atoms, e.g. fluoro or chloro, alkoxy groups having from 1 to 6 carbon atoms, e.g. methoxy or ethoxy, and carbamoyl groups.

In the compounds of formula (I), $R^3$ represents an alkyl group having from 1 to 6 carbon atoms, a haloalkyl group having from 1 to 6 carbon atoms, a hydroxyalkyl group having from 1 to 6 carbon atoms or an aryl group having from 6 to 10 carbon atoms; said aryl groups and said heteroaryl groups are unsubstituted or are substituted by at least one substituent selected from the group consisting of substituents α, preferably an alkyl group having from 1 to 6 carbon atoms, a haloalkyl group having from 1 to 6 carbon atoms or an unsubstituted aryl group having from 6 to 10 carbon atoms., more preferably, an alkyl group having from 1 to 6 carbon atoms, a haloalkyl group having from 1 to 6 carbon atoms or phenyl; more preferably, an alkyl group having from 1 to 6 carbon atoms, e.g. methyl or ethyl, or a haloalkyl group having from 1 to 6 carbon atoms, e.g. trifuluoromethyl In the compounds of formula (1), $R^4$ represents a aryl or a heteroaryl group; said aryl groups and said heteroaryl groups are unsubstituted or are substituted by at least one substituent selected from the group consisting of substituents α, defined below; said substituents α are selected from the group consisting of alkyl groups having from 1 to 6 carbon atoms, hydroxy groups, halogen atoms, alkoxy groups having from 1 to 6 carbon atoms, haloalkoxy groups having from 1 to 6 carbon atoms, alkanoyl groups having from 1 to 6 carbon atoms, alkanoylaminoalkyl groups having from 1 to 6 carbon atoms in the alkanoyl and alkyl part, haloalkyl groups having from 1 to 6 carbon atoms, carbamoyl groups, cyano groups and aminosulfonyl groups, more preferably, an aryl group having from 6 to 10 carbon atoms, or a heteroaryl group having from 5 to 7 atoms, wherein 1 to 4 of said atoms are independently selected from the group consisting of sulfur atoms, oxygen atoms and nitrogen atoms; said aryl groups and said heteroaryl groups are unsubstituted or are substituted by at least one substituent selected from the group consisting of substituents α, defined below; and said substituents α are selected from the group consisting of alkyl groups having from 1 to 6 carbon atoms, hydroxy groups, halogen atoms, alkoxy groups having from 1 to 6 carbon atoms, haloalkoxy groups having from 1 to 6 carbon atoms, alkanoyl groups having from 1 to 6 carbon atoms, haloalkyl groups having from 1 to 6 carbon atoms, carbamoyl groups, cyano groups and aminosulfonyl groups, more preferably, an aryl group having from 6 to 10 carbon atoms, or a heteroaryl group; said heteroaryl groups are selected from the group consisting of pyrazolyl, furyl, thienyl, oxazolyl, tetrazolyl, thiazolyl, imidazolyl, thiadiazolyl, pyridyl, pyrimidinyl, pyrrolyl, thiophenyl, pyrazinyl, pyridazinyl, isooxazolyl, isothiazolyl, triazolyl and furazanyl, said aryl groups and said heteroaryl groups are unsubstituted or are substituted by at least one substituent selected from the group consisting of substituents α, defined below; and said substituents α are selected from the group consisting of alkyl groups having from 1 to 6 carbon atoms, hydroxy groups, halogen atoms, alkoxy groups having from 1 to 6 carbon atoms, alkanoyl groups having from 1 to 6 carbon atoms, haloalkyl groups having from 1 to 6 carbon atoms, haloalkoxy groups having from 1 to 6 carbon atoms, carbamoyl groups, cyano groups and aminosulfonyl groups; more preferably, an aryl group having from 6 to 10 carbon atoms, or a heteroaryl group; said heteroaryl groups are selected from the group consisting of pyridyl and thiazolyl; said aryl groups and said heteroaryl groups are unsubstituted or are substituted by at least one substituent selected from the group consisting of substituents α, defined below; and said substituents α are selected from the group consisting of alkyl groups having from 1 to 6 carbon atoms, hydroxy groups, halogen atoms, alkoxy groups having from 1 to 6 carbon atoms, alkanoyl groups having from 1 to 6 carbon atoms, haloalkyl groups having from 1 to 6 carbon atoms, haloalkoxy groups having from 1 to 6 carbon atoms, carbamoyl groups, cyano groups and aminosulfonyl groups; more preferably, phenyl, pyridyl or thiazolyl; said phenyl, pyridyl and thiazolyl are unsubstituted or are substituted by at least one substituent selected from the group consisting of substituents α, defined below; and said substituents α are selected from the group consisting of alkyl groups having from 1 to 6 carbon atoms, e.g. methyl, ethyl, propyl or butyl, hydroxy groups, halogen atoms, e.g. fuluoro or chloro, alkoxy groups having from 1 to 6 carbon atoms, e.g. methoxy or ethoxy, alkanoyl groups having from 1 to 6 carbon atoms, e.g. acetyl, haloalkyl groups having from 1 to 6 carbon atoms, e.g. trifuluoromethyl, haloalkoxy groups having from 1 to 6 carbon atoms, e.g. trifuluoromethoxy, cyano groups and aminosulfonyl groups.

In the compounds of formula (I),
A represents an aryl$^1$ group having from 6 to 10 carbon atoms or an heteroaryl$^1$ group having from 5 to 7 atoms, wherein 1 to 4 of said atoms are independently selected from the group consisting of sulfur atoms, oxygen atoms and nitrogen atoms, more preferably, a phenylene or pyridylene; more preferably, a phenylene.

In the compounds of formula (I), B represents preferably ethylene.

In the compounds of formula (I),
Preferably, X represents NH, oxygen or sulfur.

Preferred individual compounds of this invention are following:

2-[4-(3,5-dimethyl-4-phenyl-1H-pyrazol-1-yl)phenyl]ethyl (4-methylphenyl)sulfonylcarbamate;
2-[4-(4-ethyl-3,5-dimethyl-1H-pyrazol-1-yl)phenyl]ethyl (4-methylphenyl)sulfonylcarbamate;
2-{4-[4-(4-fluorophenyl)-3,5-dimethyl-1H-pyrazol-1-yl]phenyl}ethyl (4-methylphenyl)sulfonylcarbamate;
2-{4-[3,5-dimethyl-4-(4-methylphenyl)-1H-pyrazol-1-yl]phenyl}ethyl (4-methylphenyl)sulfonylcarbamate;
N-[({2-[4-(3,5-dimethyl-4-phenyl-1H-pyrazol-1-yl)phenyl]ethyl}amino)carbonyl]4-methylbenzenesulfonamide;
N-{[(2-{4-[4-(4-ethoxyphenyl)-3,5-dimethyl-1H-pyrazol-1-yl]phenyl}ethyl)amino]carbonyl}-4-methylbenzenesulfonamide;
N-{[(2-{4-[4-(3,5-difluorophenyl)-3,5-dimethyl-1H-pyrazol-1-yl]phenyl}ethyl)amino]carbonyl}-4-methylbenzenesulfonamide;
N-[({2-[4-(3,5-dimethyl-4-phenyl-1H-pyrazol-1-yl)phenyl]ethyl}amino)carbonyl]-4-(methyloxy)benzenesulfonamide;
N-[({2-[4-(3,5-dimethyl-4-phenyl-1H-pyrazol-1-yl)phenyl]ethyl}amino)carbonyl]-4-[(trifluoromethyl)oxy]benzenesulfonamide;
N-[({2-[4-(3,5-dimethyl-4-phenyl-1H-pyrazol-1-yl)phenyl]ethyl}amino)carbonyl]-2-methylbenzenesulfonamide;
N-[({2-[4-(3,5-dimethyl-4-phenyl-1H-pyrazol-1-yl)phenyl]ethyl}amino)carbonyl]-4-chlorobenzenesulfonamide;
N-[({2-[4-(3,5-dimethyl-4-phenyl-1H-pyrazol-1-yl)phenyl]ethyl}amino)carbonyl]-3-methylbenzenesulfonamide;
N-[({2-[4-(3,5-dimethyl-4-phenyl-1H-pyrazol-1-yl)phenyl]ethyl}amino)carbonyl]-2-fluorobenzenesulfonamide;
N-[({2-[4-(3,5-dimethyl-4-phenyl-1H-pyrazol-1-yl)phenyl]ethyl}amino)carbonyl]-3,4-dimethoxybenzenesulfonamide;)
N-[({2-[4-(3,5-dimethyl-4-phenyl-1H-pyrazol-1-yl)phenyl]ethyl}amino)carbonyl]-2,4-difluorobenzenesulfonamide;
N-[({2-[4-(3,5-dimethyl-4-phenyl-1H-pyrazol-1-yl)phenyl]ethyl}amino)carbonyl]-3,4-difluorobenzenesulfonamide;
2,4-difluoro-N-{[(2-{4-[5-methyl-4-phenyl-3-(trifluoromethyl)-1H-pyrazol-1-yl]phenyl}ethyl)amino]carbonyl}benzenesulfonamide;
2-fluoro-N-{[(2-{4-[5-methyl-4-phenyl-3-(trifluoromethyl)-1H-pyrazol-1-yl]phenyl}ethyl)amino]carbonyl}benzenesulfonamide;
2-{4-[3,5-dimethyl-4-(3-methylphenyl)-1H-pyrazol-1-yl]phenyl}ethyl (4-methylphenyl)sulfonylcarbamate;
2-{4-[4-(3-methoxyphenyl)-3,5-dimethyl-1H-pyrazol-1-yl]phenyl}ethyl (4-methylphenyl)sulfonylcarbamate;
2-{4-[4-(3,4-dimethoxyphenyl)-3,5-dimethyl-1H-pyrazol-1-yl]phenyl}ethyl (4-methylphenyl)sulfonylcarbamate;
4-chloro-N-[({2-[4-(3-ethyl-5-methyl-4-phenyl-1H-pyrazol-1-yl)phenyl]ethyl}amino)carbonyl]benzenesulfonaimde; and
2-{4-[4-(4-ethoxyphenyl)-3,5-dimethyl-1H-pyrazol-1-yl]phenyl}ethyl (4-methylphenyl)sulfonylcarbamate;
or an ester of such compound,
and salts thereof.

Most preferred individual compounds of this invention are following:

2-[4-(3,5-dimethyl-4-phenyl-1H-pyrazol-1-yl)phenyl]ethyl (4-methylphenyl)sulfonylcarbamate;
N-[({2-[4-(3,5-dimethyl-4-phenyl-1H-pyrazol-1-yl)phenyl]ethyl}amino)carbonyl]-4-methylbenzenesulfonamide;
N-{[(2-{4-[4-(4-ethoxyphenyl)-3,5-dimethyl-1H-pyrazol-1-yl]phenyl}ethyl)amino]carbonyl}-4-methylbenzenesulfonamide;
N-[({2-[4-(3,5-dimethyl-4-phenyl-1H-pyrazol-1-yl)phenyl]ethyl}amino)carbonyl]-4-(methyloxy)benzenesulfonamide;
N-[({2-[4-(3,5-dimethyl-4-phenyl-1H-pyrazol-1-yl)phenyl]ethyl}amino)carbonyl]-3,4-dimethoxybenzenesulfonamide;
2,4-difluoro-N-{[(2-{4-[5-methyl-4-phenyl-3-(trifluoromethyl)-1H-pyrazol-1-yl]phenyl}ethyl)amino]carbonyl}benzenesulfonamide; and
2-fluoro-N-{[(2-{4-[5-methyl-4-phenyl-3-(trifluoromethyl)-1H-pyrazol-1-yl]phenyl}ethyl)amino]carbonyl}benzenesulfonamide;
or an ester of such compound,
and salts thereof.

General Synthesis

The compounds of the present invention may be prepared by a variety of processes well known for the preparation of compounds of this type, for example as shown in the following reaction Schemes. Unless otherwise indicated R$^1$ through R$^4$ and A, B and X in the reaction Schemes and discussion that follow are defined as above.

The following reaction Schemes illustrate the preparation of compounds of formula (I).

Scheme 1

This illustraates the preparation of compounds of formula (I).

Scheme 1

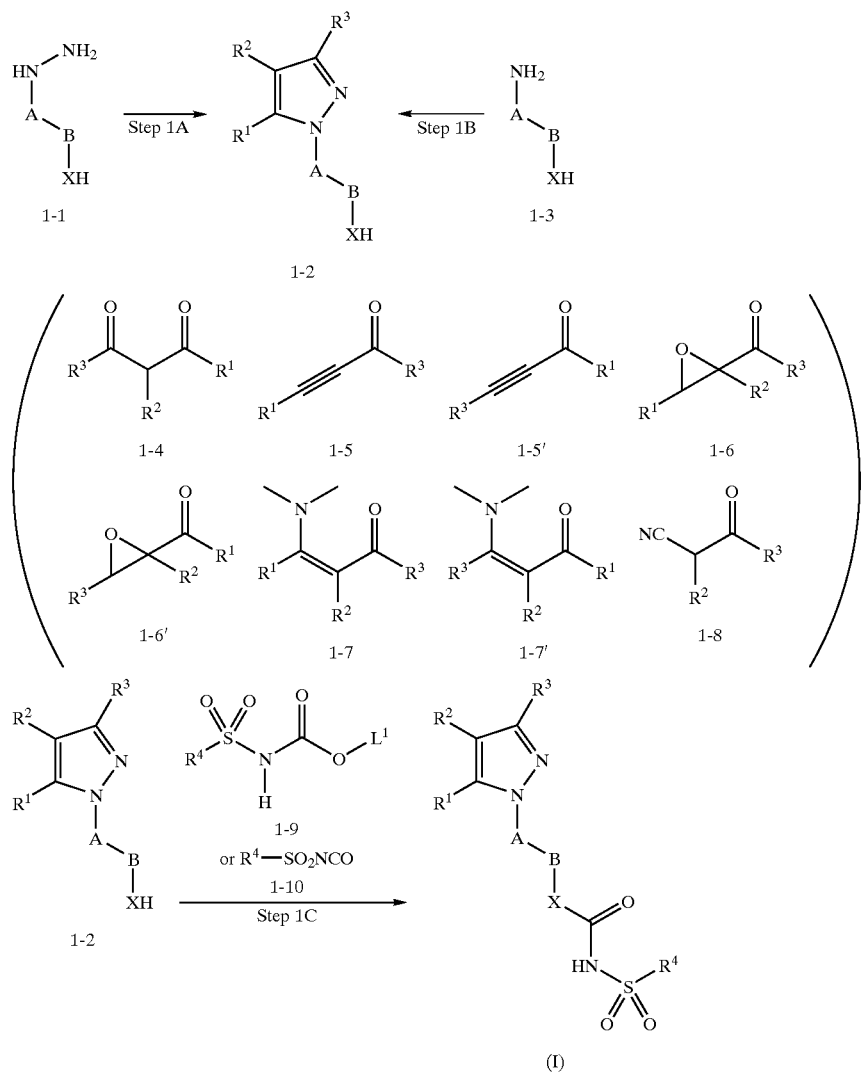

In the above formula, $L^1$ represents an alkyl group having from 1 to 6 carbon atoms, a substituted alkyl group having from 1 to 6 carbon atoms, an aryl group having from 6 to 10 carbon atoms or a substituted aryl group having from 6 to 10 carbon atoms.

Step 1A

In this Step, a pyrazole compound of formula 1-2 may be prepared by the condensation of a hydrazine compound of formula 1-1 with compounds selected from the groups consisting of formula 1-4,1-5, 1-5', 1-6,1-6', 1-7,1-7' or 1-8 in an inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water, aliphatic hydrocarbons, such as hexane, heptane and petroleum ether; aromatic hydrocarbons, such as benzene, toluene and xylene; halogenated hydrocarbons, such as methylene chloride, chloroform, carbon tetrachloride and dichloroethane; ethers, such as diethyl ether, diisopropyl ether, tetrahydrofuran and dioxane; alcohols, such as methanol, ethanol, propanol, isopropanol and butanol; and organic acids, such as acetic acid and propionic acid. Of these solvents, we prefer the alcohols.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 5° C. to 200° C., more preferably from room temperature to 150° C. The time required for the reaction may also vary widely, depending on many factors, notably the reaction temperature and the nature of the reagents and solvent employed. However, provided that the reaction may be effected under the preferred conditions outlined above, a period of from 10 minutes to 60 hours, more preferably from 1 hour to 50 hours, will usually suffice.

This reaction may be carried out in the presence or absence of a acid catalyst. Examples of suitable acids include: hydrochoric acid, acetic acid, sulfuric acid, nitric acid, methanesulfonic acid, benzenesulfonic acid, and p-toluenesulfonic acid.

Step 1B

Alternatively, the pyrazole compound of formula 1-2 may be prepared by diazotizing the amine portion of the compound of formula 1-3 followed by reduction to obtain the corresponding a hydrazine compound, which is then condensed with compounds selected from the groups consisting of formula 1-4,1-5, 1-5', 1-6,1-6' or 1-7 with or without separation in an inert solvent.

The diazotization reaction may be carried out by conventional methods. Examples of suitable diazotizing agents include: sodium nitirite, potassium nitrite, isoamyl nitrite, and potassium metabisulfite.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; alcohols, such as methanol, ethanol, propanol, isopropanol and butanol; and organic acids, such as acetic acid and propionic acid. Of these solvents, we prefer the water.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −50° C. to room temperature more preferably from −20° C. to room temperature. The time required for the reaction may also vary widely, depending on many factors, notably the reaction temperature and the nature of the reagents and solvent employed. However, provided that the reaction may be effected under the preferred conditions outlined above, a period of from 1 minute to 10 hours, more preferably from 10 minutes to 5 hours, will usually suffice.

This reaction may be carried out in the presence or absence of a acid catalyst. Examples of suitable acids include: hydrochoric acid, acetic acid, sulfuric acid, nitric acid, and tetrafluoroboronic acid.

The reduction of the above obtained diazonium ion may be effected using a reducing agent. Examples of suitable reducing agents include: Fe, Sn or Zn, and sodium sulfite. These reactions are well known in the field of synthetic organic chemistry and may be carried out using well known techniques The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; alcohols, such as methanol, ethanol, propanol, isopropanol and butanol; and organic acids, such as acetic acid and propionic acid. Of these solvents, we prefer the water and alcohols.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −50° C. to 100° C. more preferably from −20° C. to 50° C. The time required for the reaction may also vary widely, depending on many factors, notably the reaction temperature and the nature of the reagents and solvent employed. However, provided that the reaction may be effected under the preferred conditions outlined above, a period of from 1 minute to 10 hours, more preferably from 10 minutes to 5 hours, will usually suffice.

This reaction may be carried out in the presence or absence of a acid catalyst. Examples of suitable acids include: hydrochoric acid, acetic acid, sulfuric acid, nitric acid.

The pyrazole compound of formula 1-2 may be prepared by the condensation of the above obtained hydrazine compound with compounds selected from the groups consisting of formula 1-4,1-5, 1-5', 1-6,1-6', 1-7,1-7' or 1-8 in an inert solvent. This reaction is essentially the same as and may be carried out in the same manner as and using the same reagents and reaction conditions as Step 1A in Scheme 1.

Step 1C

In this Step, the desired compound of formula (I), which is a compound of the present invention, may be prepared by the reacting the compound of formula 1-2, prepared as described in Step 1A with compounds selected from the groups consisting of formula 1-9 or 1-10 in an inert solvent.

The reaction may be carried out in the absence or presence of a reaction inert solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene, xylene, o-dichlorobenzene, nitrobenzene and pyridine; halogenated hydrocarbons, such as methylene chloride, chloroform, carbon tetrachloride and dichloroethane; ethers, such as diethyl ether, diisopropyl ether, tetrahydrofuran and dioxane; ethylacetate, aceronitrile, N,N-dimethylformamide, dimethylsulfoxide. Of these solvents, we prefer the halogenated hydrocarbons and pyridine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100° C. to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to 24 hours, more preferably from 20 minutes to 5 hours, will usually suffice.

This reaction may be carried out in the presence or absence of a base. There is likewise no particular restriction on the nature of the bases used, and any base commonly used in reactions of this type may equally be used here. Examples of such bases include: pyridine, picoline, triethylamine, tributylamine, diisopropylethylamine, N-methylmorphorine, N-methylpiperidine, 4-(N,N-dimethylamino)pyridine.

Compounds of formula 1-4, 1-5, 1-5', 1-6,1-6', 1-7, 1-7', 1-8, 1-9 or 1-10 may be a known compound or readily prepared by known methods (e.g., *J. Med. Chem.*, 1999, 42, 2504, *J. Med. Chem.*, 1997, 40, 1347, *Helv. Chim. Acta*, 1992, 1320 and *Chem. Pharm. Bull.*, 1991, 39, 86, *J. Org. Chem.*, 1993, 58, 7606).

Scheme 2

This illustrates the preparation of compounds of formula (Ia) wherein X represents NH or N[$(C_1–C_6)$alkyl].

Scheme 2

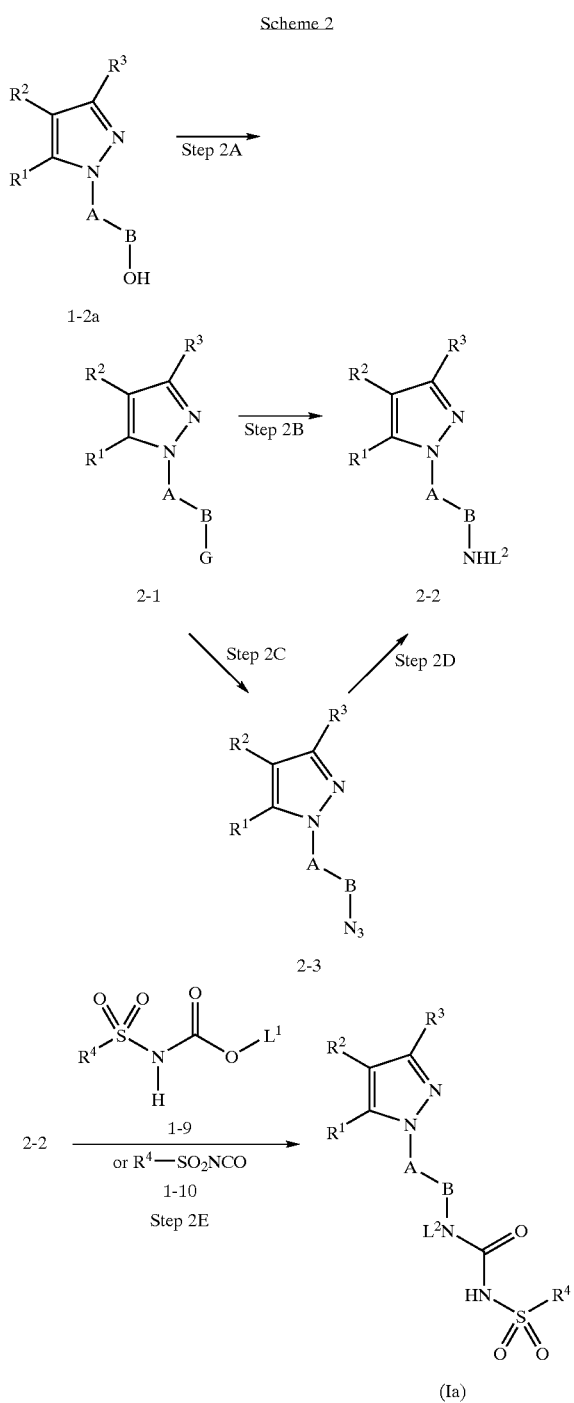

In the above formula, L² represents a hydrogen atom or an alkyl group having from 1 to 6 carbon atoms.
G represents a leaving group. Example of suitable leaving groups include: halogen atoms, such as chlorine, bromine and iodine; sulfonic esters such as TfO (triflates), MsO (mesylates), TsO (tosylates); and the like.

Step 2A

In this Step, a pyrazole compound of formula 1-2a, prepared as described in Step 1A (compounds of formula 1-2 wherein X is oxygen), may be converted to compound with a leaving group G of formula 2-1 under conditions known to those skilled in the art.

For example, the hydroxy group of the compound of formula 1-2a may be converted to the halogen atom using a halogenating agent in the presence or absence of a reaction inert solvent. Preferred halogenating agents include: chlorinating agents, such as thionyl chloride, oxalyl chloride, para-toluenesulfonyl chloride, methanesulfonyl chloride, hydrogen chloride, phosphorus trichloride, phosphorus pentachloride, N-chlorosuccinimide (NCS), phosphorus oxychloride, trimethylsilyl chloride or phosphorus reagents such as triphenylphosphine, tributyl phosphine or triphenylphosphite in the presence of halogen source such as carbon tetrachloride, chlorine, NCS; brominating agents, such as hydrogen bromide, N-bromosuccinimide (NBS), phosphorus tribromide, trimethylsilyl bromide or phosphorus reagents such as triphenylphosphine, tributyl phosphine or triphenylphosphite in the presence of halogen source such as carbon tetrabromide, bromine or NBS; and iodinating agents, such as hydroiodic acid, phosphorus triiodide, or phosphorus reagents such as triphenylphosphine, tributyl phosphine or triphenylphosphite in the presence of halogen source such as iodine.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; aromatic hydrocarbons, such as benzene, toluene, o-dichlorobenzene, nitrobenzene, pyridine, and xylene; halogenated hydrocarbons, such as methylene chloride, chloroform, carbon tetrachloride and 1,2-dichloroethane; and ethers, such as diethyl ether, diisopropyl ether, tetrahydrofuran and dioxane. Of these solvents, we prefer the aromatic hydrocarbons, halogenated hydrocarbons and ethers.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100° C. to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to a day, more preferably from 20 minutes to 5 hours, will usually suffice.

Alternatively, a hydroxy group of the compound of formula 1-2a may be converted to the sulfonate group using a sulfonating agent in the presence of, or absence of a base. Example of such sulfonating agents include: para-toluenesulfonyl chloride, para-toluenesulfonic anhydride, methanesulfonyl chloride, methanesulfonic anhydride, trifluoromethanesulfonic anhydride, or the like in the presence of, or absence of a reaction-inert solvent. Example of such bases include: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, pyridine or dimethylaminopyridine in the presence or absence of a reaction inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; aromatic hydrocarbons, such as benzene, toluene, o-dichlorobenzene, nitrobenzene, pyridine, and xylene; halogenated hydrocarbons, such as methylene chloride, chloroform, carbon tetrachloride and 1,2-dichloroethane; and ethers, such as diethyl ether, diisopropyl ether, tetrahydrofuran and dioxane; N,N-dimethylformamide, and dimethylsulfoxide The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100° C. to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to a day, more preferably from 20 minutes to 5 hours, will usually suffice.

Step 2B

In this Step, a pyrazole compound of formula 2-2 may be prepared by the amination of the above obtained compound of formula 2-1 with $L^2$-$NH_2$ wherein $L^2$ is as defined above in an inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water, aliphatic hydrocarbons, aliphatic hydrocarbons, such as hexane, heptane and petroleum ether; aromatic hydrocarbons, such as benzene, toluene o-dichlorobenzene, nitrobenzene, pyridine, and xylene; halogenated hydrocarbons, such as methylene chloride, chloroform, carbon tetrachloride and 1,2-dichloroethane; ethers, such as tetrahydrofuran and dioxane; and alcohols, such as methanol, ethanol, propanol, isopropanol, butanol and ethyleneglycol. Of these solvents, we prefer the aromatic hydrocarbons, ethers, and alcohols.

The reaction can take place over a wide range of temperatures, and the precise reaction temperature is not critical to the invention. The preferred reaction temperature will depend upon such factors as the nature of the solvent, and the starting material or reagent used. However, in general, it is convenient to carry out the reaction at a temperature of from −100° C. to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to 3 days, more preferably from 20 minutes to 50 hours, will usually suffice.

This reaction may be carried out in the presence or absence of a base. There is likewise no particular restriction on the nature of the bases used, and any base commonly used in reactions of this type may equally be used here. Examples of such bases include: an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine, dimethylaminopyridine, 1,8-diazabicyclo[5.4.0]undec-7-ene.

Step 2C

In this Step, an azide compound of formula 2-3 may be prepared by the nucleophilic displacement of the above obtained compound of formula 2-1 with azide in an inert solvent.

Examples of suitable azide agents include sodium azide or lithium azide.

This reaction may be carried out in the presence of a suitable additive agent. Examples of such additive agents include: sodium iodide, potassium iodide, 1,4,7,10.13-pentaoxacyclopentadecane(15-Crown-5) or 1,4,7,10-tetraoxacyclododecane (12-Crown-4).

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; aromatic hydrocarbons, such as benzene, toluene, o-dichlorobenzene, nitrobenzene, pyridine, and xylene; ethers, such as tetrahydrofuran and dioxane. N,N-dimethylformamide, and dimethoxyethane. Of these solvents, we prefer the water and N,N-dimethylformamide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to 3 days, more preferably from 20 minutes to 50 hours, will usually suffice.

Step 2D

In this Step, which is an alternative to Step 2B, the amine compound of formula 2-2 may be prepared by carrying out reduction of the azide compound of formula 2-3, prepared as described in Step 2C.

The reduction may also be carried out under known hydrogenation conditions in the presence of a metal catalyst such as Lindlar catalysts, Raney nickel catalysts, palladium catalysts or platinum catalysts (preferably Lindlar catalysts, palladium catalysts or platinum catalysts). This reaction may be carried out under hydrogen atmosphere in a reaction inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: acetic acid, alcohols, such as methanol, ethanol; ethyl acetate, tetrahydrofuran, and N,N-dimethylformamide. Of these solvent, the alcohols and N,N-dimethylformamide are preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100° C. to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to 3 days, more preferably from 20 minutes to 50 hours, will usually suffice.

Step 2 E

In this Step, the desired compound of formula (Ia), which is a compound of the present invention, may be prepared by the reacting the compound of formula 2-2, prepared as described in Step 2B and 2D with compounds selected from the groups consisting of formula 1-9 or 1-10 in an inert solvent.

This reaction is essentially the same as and may be carried out in the same manner as and using the same reagents and reaction conditions as Step 1C in Scheme 1.

Scheme 3

This illustrates the alternative preparation of compounds of formula (I).

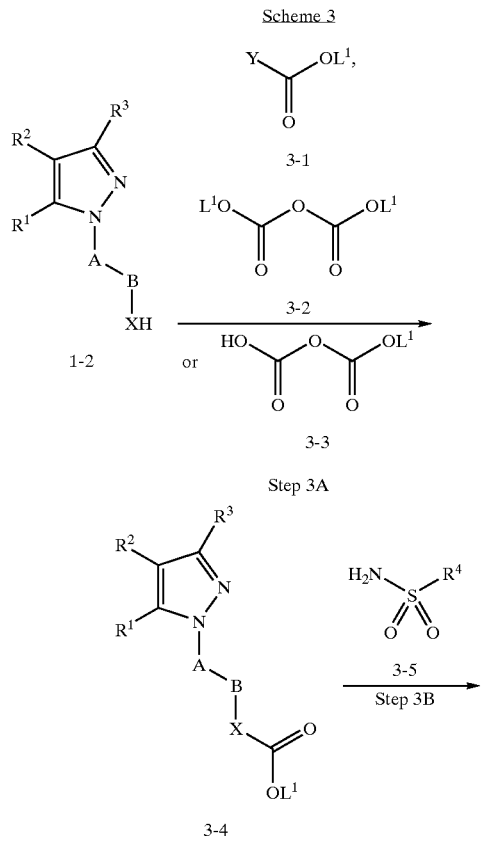

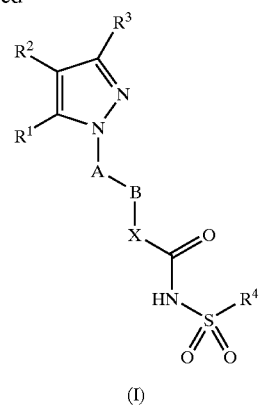

In the above formula, Y represents a halogen atom, for example, chlorine, bromine and iodine;

Step 3A

In this Step, a carbonyl pyrazole compound of formula 3-4 may be prepared by the coupling of a pyrazole compound of formula 1-2, prepared as described in Step 1A in Scheme 1 with compounds selected from the groups consisting of formula 3-1, 3-2 or 3-3 in an inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene, o-dichlorobenzene, nitrobenzene, pyridine and xylene; halogenated hydrocarbons, such as methylene chloride, chloroform, carbon tetrachloride and 1,2-dichloroethane; ethers, such as diethyl ether, diisopropyl ether, tetrahydrofuran and dioxane; N,N-dimethylformamide, dimethylsulfoxide. Of these solvents, the halogenated hydrocarbons and pyridine are preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 250° C., more preferably from 0 to 150° C. The time required for the reaction may also vary widely, depending on many factors, notably the reaction temperature and the nature of the reagents and solvent employed. However, provided that the reaction may be effected under the preferred conditions outlined above, a period of from 10 minutes to 24 hours, more preferably from 20 minutes to 5 hours, will usually suffice.

This reaction may be carried out in the presence or absence of a base. Examples of suitable bases include: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, cesium carbonate, potassium fluoride, sodium hydride or potassium hydride, or an amine such as triethylamine, tributylamine, diisopropylethylamine, pyridine or dimethylaminopyridine.

Step 3B

In this Step, the desired compound of formula (I), which is a compound of the present invention, may be prepared by the reacting the compound of formula 3-4, prepared as described in Step 3A with a sulfonamide compound of formula 3-5 in an inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene, o-dichlorobenzene, nitrobenzene, pyridine and xylene; halogenated hydrocarbons, such as methylene chloride, chloroform, carbon tetrachloride and dichloroethane; ethers, such as diethyl ether, diisopropyl ether, tetrahydrofuran and dioxane; acetonitrile, N,N-dimethylformamide, N,N-dimethylsulfoxide. Of these solvents, N,N-dimethylformamide and acetonitrile are preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100 to 250° C., more preferably from 0° C. to 150° C. The time required for the reaction may also vary widely, depending on many factors, notably the reaction temperature and the nature of the reagents and solvent employed. However, provided that the reaction may be effected under the preferred conditions outlined above, a period of from 1 minute to 3 days, more preferably from 20 minutes to 50 hours, will usually suffice.

This reaction may be carried out in the presence or absence of a base. Examples of suitable bases include: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, cesium carbonate, potassium fluoride, sodium hydride or potassium hydride, or an amine such as triethylamine, tributylamine, diisopropylethylamine, pyridine or dimethylaminopyridine, 1,8-diazabicyclo[5.4.0]undec-7-ene.

Compounds of formula 3-1, 3-2, 3-3 or 3-5 may be a known compound or readily prepared by known methods.

Scheme 4

This illustrates the preparation of compounds of formula (Ib) wherein $R^2$ represents an aryl group or a heteroaryl group.

Scheme 4

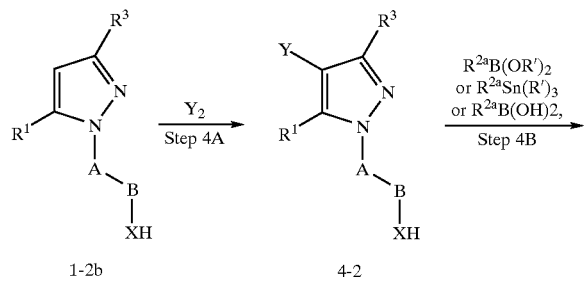

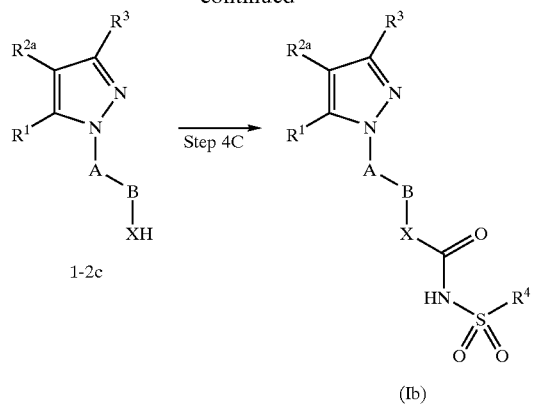

In the above formula, $R^{2a}$ represents an aryl group or a heteroaryl group; R' represents an alkyl group having from 1 to 6 carbon atoms.

Step 4A

In this Step, a pyrazole compound of formula 1-2b, prepared as described in Step 1A (compounds of formula 1-2 wherein $R^2$ is a hydrogen atom), may be converted to a halogenated pyrazole compound of formula 4-2 under conditions known to those skilled in the art.

For example, the hydrogen atom of the compound of formula 1-2b may be converted to the halogen atom using a halogenating agent in the presence or absence of a reaction inert solvent. Preferred halogenating agents include: chlorinating agents, such as sulfunyl chloride, thionyl chloride, hydrogen chloride, phosphorus trichloride, phosphorus pentachloride, N-chlorosuccinimide (NCS), phosphorus oxychloride; brominating agents, such as bromine, hydrogen bromide, N-bromosuccinimide (NBS), phosphorus tribromide, trimethylsilyl bromide or phosphorus reagents such as triphenylphosphine, tributyl phosphine or triphenylphosphite in the presence of halogen source such as carbon tetrabromide, bromine or NBS; and iodinating agents, such as hydroiodic acid, phosphorus triiodide, iodinemonochloride, or phosphorus reagents such as triphenylphosphine, tributyl phosphine or triphenylphosphite in the presence of halogen source such as iodine.

The halogenation may be carried out in the presence of oxidatiing agents, for example, cerium ammonium nitrate (CAN), hydrogen peroxide.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water, acetic acid, aliphatic hydrocarbons, such as hexane, heptane and petroleum ether; aromatic hydrocarbons, such as benzene, toluene o-dichlorobenzene, nitrobenzene, pyridine, and xylene; halogenated hydrocarbons, such as methylene chloride, chloroform, carbon tetrachloride and dichloroethane; and ethers, such as diethyl ether, diisopropyl ether, tetrahydrofuran and dioxane, and alcohols, such as methanol, ethanol, propanol, isopropanol, butanol, N,N-dimethylformamide, dimethylsulfoxide, and acetonitrile. Of these solvents, the acetonitrile and halogenated hydrocarbons are preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100° C. to 250° C., more preferably from 0° C. to 100° C. The time required for the reaction may also vary widely, depending on many factors, notably the reaction temperature and the nature of the reagents and solvent employed. However, provided that the reaction may be effected under the preferred conditions outlined above, a period of from 1 minute to 5 days, more preferably from 20 minutes to 3 days, will usually suffice.

Step 4B

In this Step, a pyrazole compound of formula 1-2c may be prepared by the coupling of the above obtained compound of formula 4-2 with agents selected from the groups consisting of $R^{2a}B(OH)_2$, $R^{2a}B(OR')_2$ and $R^{2a}Sn(R')_3$ wherein $R^{2a}$ and R' are as defined above in an inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; aromatic hydrocarbons, such as benzene, toluene, nitrobenzene, pyridine, and xylene; halogenated hydrocarbons, such as methylene chloride, chloroform, carbon tetrachloride and dichloroethane; and ethers, such as diethyl ether, diisopropyl ether, alcohols, such as methanol, ethanol, propanol, isopropanol, butanol, ethyleneglycol; dimethoxyethane, tetrahydrofuran, dioxane, water, acetone, acetonitrile, N,N-dimethylformamide, and dimethylsulfoxide. Of these solvents, we prefer the alcohols, aromatic hydrocarbons, N,N-dimethylformamide, dimethylsulfoxide, ethers and water.

The reaction can take place over a wide range of temperatures, and the precise reaction temperature is not critical to the invention. The preferred reaction temperature will depend upon such factors as the nature of the solvent, and the starting material or reagent used. However, in general, it is convenient to carry out the reaction at a temperature of from −100° C. to 250° C., more preferably from 0° C. to 150° C. The time required for the reaction may also vary widely, depending on many factors, notably the reaction temperature and the nature of the reagents and solvent employed. However, provided that the reaction may be effected under the preferred conditions outlined above, a period of from 1 minute to 7 days, more preferably from 20 minutes to 2 days, will usually suffice.

This reaction may be carried out in the presence a suitable catalyst. There is likewise no particular restriction on the nature of the catalysts used, and any catalysts commonly used in reactions of this type may equally be used here. Examples of such catalysts include: tetrakis(triphenylphosphine)-palladium, bis(triphenylphosphine)palladium(II) dichloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, copper(II) trifluoromethanesulfonate, palladium(II) acetate, palladium (II) chloride, bisacetonitriledichloropalladium(0), bis(dibenzylideneacetone)palladium(0), tris(dibenzylideneacetone)dipalladium(0), [1,1'-bis(diphenylphosphino)ferrocene]palladium(II) dichloride, or [1,1'-bis(diphenylphosphino)ferrocene]dichloronickel(II), silver(I) oxide.

This reaction may be carried out in the presence of a suitable additive agent. Examples of such additive agents include: triphenylphosphine, tri-tert-butylphosphine, 1,1'-bis(diphenylphosphino)ferrocene, tri-2-furylphosphine, tri-o-tolyephosphine, 2-(dichlorohexylphosphino)biphenyl or triphenylarsine.

This reaction may be carried out in the presence or absence of a base. There is likewise no particular restriction on the nature of the bases used, and any base commonly used in reactions of this type may equally be used here. Examples of such bases include: lithium hydroxide, sodium hydroxide, potassium hydroxide, barium hydroxide, sodium carbonate, potassium carbonate, cesium carbonate, thallium(I) carbonate, sodium ethoxide, potassium tert-butoxide, potassium acetate, cesium fluoride, tetrabutylammonium fluoride, tetrabutylammonium chloride, tetrabutylammonium iodide, pyridine, 1,8-diazabicyclo[5.4.0]undecan, picoline, 4-(N,N-dimethylamino)pyridine, triethylamine, tributylamine, diisopropylethylamine, N-methylmorphorine and N-methylpiperidine.

Step 4C

In this Step, the desired compound of formula (Ib), which is a compound of the present invention, may be prepared by the reacting the compound of formula 1-2c, prepared as described in Step 4B.

This reaction is essentially the same as and may be carried out in the same manner as and using the same reagents and reaction conditions as Step 1C in Scheme 1 and Steps 3A and 3B in Scheme 3.

Compounds of formula $R^{2a}B(OH)_2$, $R^{2a}B(OR')_2$ and $R^{2a}Sn(R')_3$ may be a known compound or readily prepared by known methods Scheme 5

This illustrates the preparation of compounds of formula (Ic) wherein $R^1$ represents an amino group.

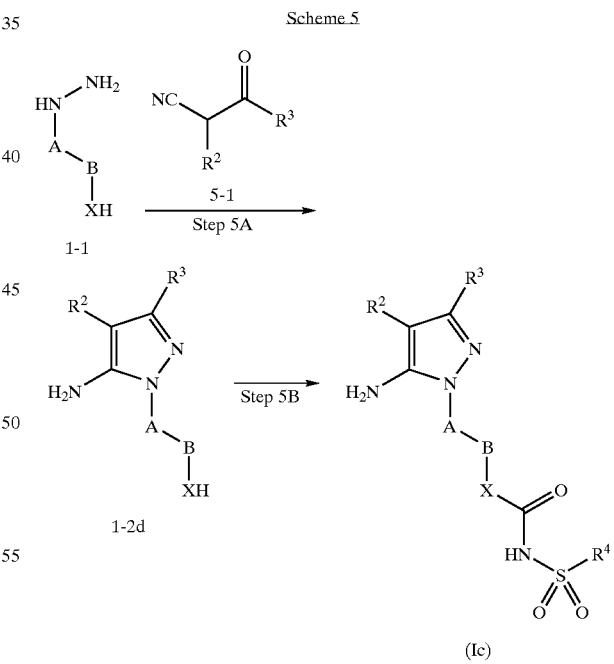

(Ic)

Step 5A

In this Step, a pyrazole compound of formula 1-2d may be prepared by the condensation of a hydrazine compound of formula 1-1 with a nitrile compound of formula 5-1 in an inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water, aliphatic hydrocarbons, such as hexane, heptane and petroleum ether; aromatic hydrocarbons, such as benzene, toluene and xylene; halogenated hydrocarbons, such as methylene chloride, chloroform, carbon tetrachloride and dichloroethane; ethers, such as diethyl ether, diisopropyl ether, tetrahydrofuran and dioxane; alcohols, such as methanol, ethanol, propanol, isopropanol and butanol; and organic acids, such as acetic acid and propionic acid. Of these solvents, the alcohols are preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 5° C. to 200° C., more preferably from room temperature to 150° C. The time required for the reaction may also vary widely, depending on many factors, notably the reaction temperature and the nature of the reagents and solvent employed. However, provided that the reaction may be effected under the preferred conditions outlined above, a period of from 10 minutes to 60 hours, more preferably from 1 hour to 50 hours, will usually suffice.

This reaction may be carried out in the presence or absence of a acid catalyst. Examples of suitable acids include: hydrochoric acid, acetic acid, sulfuric acid, nitric acid, methanesulfonic acid, benzenesulfonic acid, p-toluenesulfonic acid.

Step 5B

In this Step, the desired compound of formula (Ic), which is a compound of the present invention, may be prepared by the reacting the compound of formula 1-2d, prepared as described in Step 5A.

This reaction is essentially the same as and may be carried out in the same manner as and using the same reagents and reaction conditions as Step 1C in Scheme 1 and Steps 3A and 3B in Scheme 3.

Compounds of formula 5-1 may be a known compound or readily prepared by known methods.

Scheme 6

This illustrates the preparation of compounds of formula (Id) wherein A' represents a heteroaryl group, B represents ethylene and X represents NH.

Scheme 6

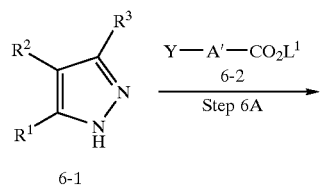

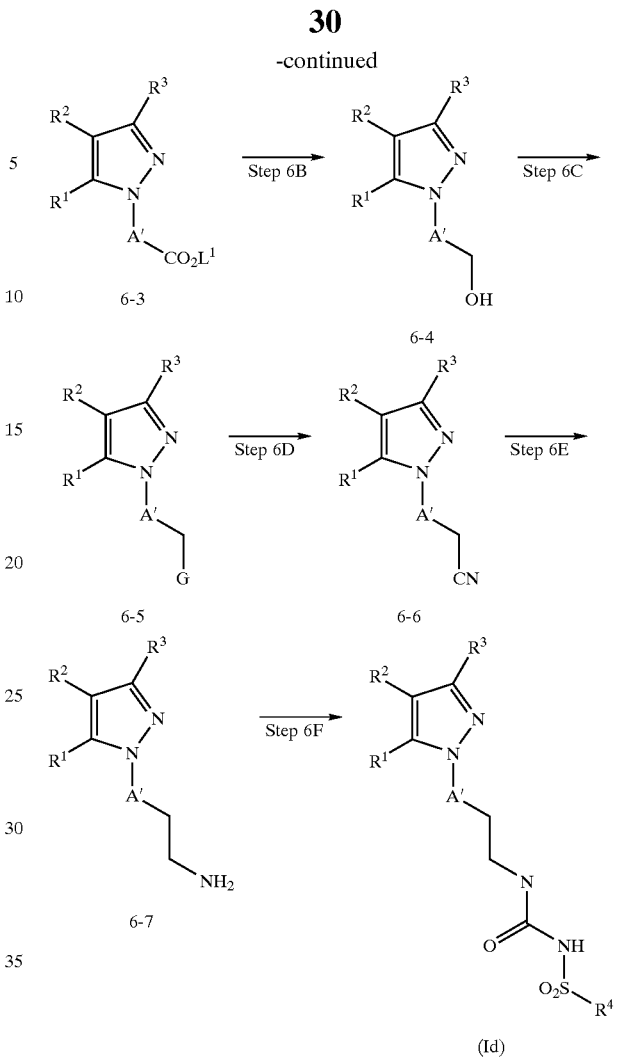

In the above formula, A' represents a heteroaryl group.

Step 6A

In this Step, a pyrazole compound of formula 6-1 may be converted to a carboxylate compound of formula 6-3 under conditions known to those skilled in the art.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; aromatic hydrocarbons, such as benzene, toluene and xylene, o-dichlorobenzene, nitrobenzene, pyridine; ethers, such as diethyl ether, diisopropyl ether, tetrahydrofuran and dioxane; alcohols, such as methanol, ethanol, propanol, isopropanol, butanol and ethyleneglycol; N,N-dimethylformamide, dimethylsulfoxide, water, acetonitrile, 1,3-dimethyl-2-imidazolidinone, 1-methyl-2-pyrrolidinone. Of these solvents, dimethylsulfoxide is preferred.

The reaction can take place over a wide range of temperatures, and the precise reaction temperature is not critical to the invention. The preferred reaction temperature will depend upon such factors as the nature of the solvent, and the starting material or reagent used. However, in general, it is convenient to carry out the reaction at a temperature of from 5° C. to 250° C., more preferably from room temperature to 200° C. The time required for the reaction may also vary widely, depending on many factors, notably the reaction temperature and the nature of the reagents and solvent employed. However, provided that the reaction may be effected under the preferred conditions outlined above, a period of from 10 minutes to 3 days, more preferably from 1 hour to 50 hours, will usually suffice.

The reaction may be carried out in the presence of, or absence of a base. Example of such bases include: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, pyridine or dimethylaminopyridine.

Step 6B

Then the resulting compound of formula 6-3 may be subjected to reduction to give the compound of formula 6-4. The reduction may be carried out in the presence of a suitable reducing agent in a reaction inert solvent or without solvent. A preferred reducing agent is selected from, for example, $LiAlH_4$ or $LiBH_4$.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; aromatic hydrocarbons, such as benzene, toluene, o-dichlorobenzene, and xylene; ethers, such as diethyl ether, diisopropyl ether, tetrahydrofuran, diglyme and dioxane. Of these solvents, the ethers are preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from –100 to 250° C., more preferably from –10° C. to 150° C. The time required for the reaction may also vary widely, depending on many factors, notably the reaction temperature and the nature of the reagents and solvent employed. However, provided that the reaction may be effected under the preferred conditions outlined above, a period of from 1 minute to a day, preferably from 20 minutes to 5 hours, will usually suffice.

Step 6C

In this Step, a pyrazole compound of formula 6-4, prepared as described in Step 6B, may be converted to compound with a leaving group G of formula 6-5 under conditions known to those skilled in the art.

This reaction is essentially the same as and may be carried out in the same manner as and using the same reagents and reaction conditions as Step 2A in Scheme 2.

Step 6D

In this Step, the leaving group in compound of formula 6-5, prepared as described in Step 6C, may be converted to a nitrile compound of formula 6-6 under conditions known to those skilled in the art.

The nucleophilic displacement with nitrile may be carried out by conventional procedures in the absence or presence of a reaction inert solvent.

Example of reaction inert solvents include, water, aromatic hydrocarbons, such as benzene, toluene and xylene; ethers, such as tetrahydrofuran and dioxane; alcohols, N,N-dimethylformamide, and dimethoxyethane. Of these solvents, the water and NAN-dimethylformamide are preferred Examples of nitrile agents are selected from sodium cyanide or potassium cyanide.

Reaction temperatures are generally in the range of –100° C. to 250° C., preferably in the range of 0° C. to 100° C., but if necessary, lower or higher temperature can be employed. Reaction times are, in general, from several minutes to 2 days, preferably from 20 minutes to a day.

Step 6E

In this Step, the nitrile group in compound of formula 6-6, prepared as described in Step 6D, may be subjected to reduction to obtain a amine compound of formula 6-7 under conditions known to those skilled in the art.

The reduction of the compound of formula 6-6 may be carried out in the presence of a suitable reducing agent such as diboran, boran-methyl sulfide complex, or lithium aluminum hydride in a reaction inert solvent selected form, tetrahydrofuran or diethyl ether. Reaction temperatures are generally in the range of –100 to 250° C., preferably in the range of 0° C. to the reflux temperature, but if necessary, lower or higher temperature can be employed. Reaction times are, in general, from 1 minute to a day, preferably from 20 minutes to 5 hours, however shorter or longer reaction times, if necessary, can be employed.

The reduction of the compound of formula 6-6 may also be carried out under known hydrogenation conditions such as in the presence of a metal catalyst such as Raney nickel catalysts in the presence or absence of hydrazine, palladium catalysts or platinum catalysts under hydrogen atmosphere. This reaction may be carried out in a reaction inert solvent such as methanol, ethanol, and tetrahydrofuran in the presence or absence of hydrogen chloride. If necessary, this reduction may be carried out under the adequate pressure in the range from about 0.5 to 10 $kg/cm^2$, preferably in the range from 1 to 6 $kg/cm^2$. Reaction temperatures are generally in the range of –100° C. to 250° C., preferably in the range of 0° C. to the reflux temperature, but if necessary, lower or higher temperature can be employed. Reaction times are, in general, from 1 minute to 2 days, preferably from 20 minutes to 24 hours.

Step 6F

In this Step, the desired compound of formula (Id), which is a compound of the present invention, may be prepared by the reacting the compound of formula 6-7, prepared as described in Step 6E.

This reaction is essentially the same as and may be carried out in the same manner as and using the same reagents and reaction conditions as Step 1C in Scheme 1 and Steps 3A and 3B in Scheme 3.

Compounds of formula 6-1 and 6-2 may be a known compound or readily prepared by known methods.

Scheme 7

This illustrates the alternative preparation of compounds of formula (I).

Scheme 7

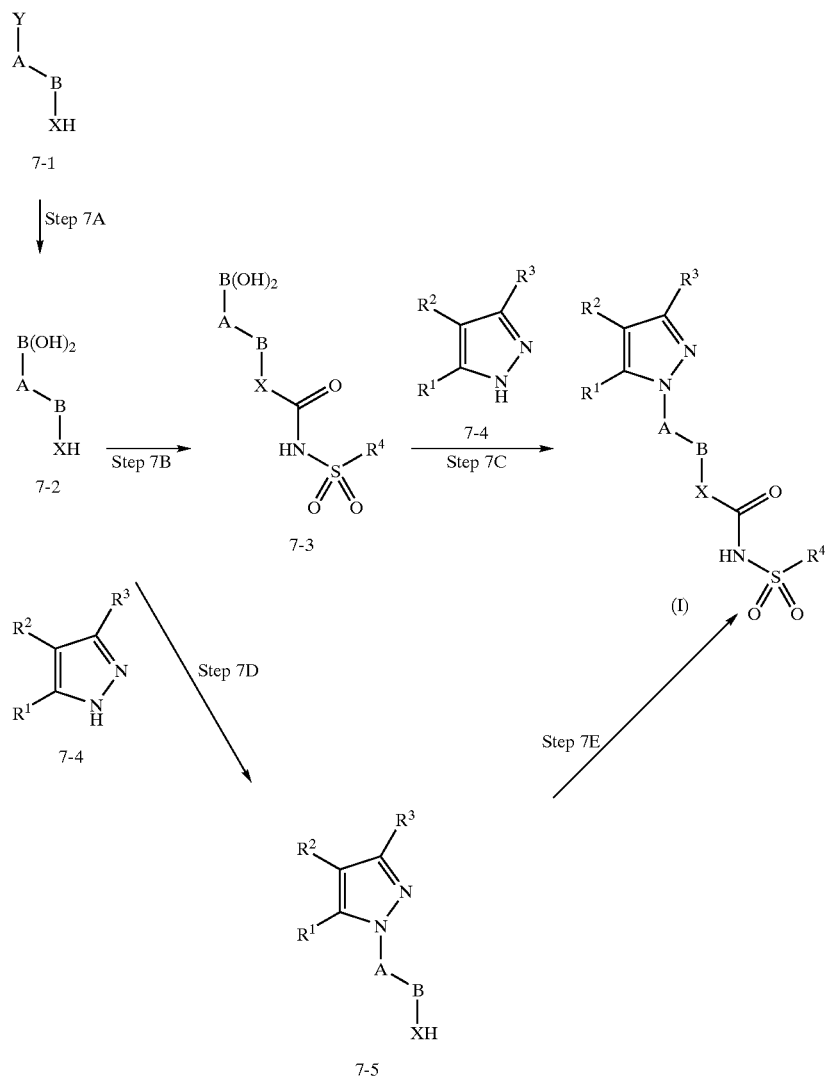

Step 7A

In this Step, a boronic acid compound of formula 7-2 may be prepared from halo compound of formula 7-1 under conditions known to those skilled in the art.

For example, the hydroxy group of the compound of formula 7-1 may be converted to the boronic acid using B(OR') wherein R' represents an alkyl group having from 1 to 6 carbon atoms in the presence or absence of a reaction inert solvent.

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane and petroleum ether; and ethers, such as diethyl ether, diisopropyl ether, tetrahydrofuran and dioxane. Of these solvents, the aliphatic hydrocarbons and ethers are perferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100° C. to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to 2 days, more preferably from 20 minutes to 60 hours, will usually suffice.

This reaction may be carried out in the presence of a base. There is likewise no particular restriction on the nature of the bases used, and any base commonly used in reactions of this type may equally be used here. Examples of such bases include: lithium, alkyl lithium, such as n-butyl lithium, tert-butyl lithium, sec-butyl lithium and aryl lithium such as phenyl lithium.

This reaction may be followed by an acidic hydrolysis in the presence of an acid to obtain the compound of formula 7-2. Examples of suitable acids include: hydrochloric acid, sulfuric acid, hydrobromic acid.

Step 7B

In this Step, a sulfonamide compound of formula 7-3 may be prepared by the sulfonamidecarbonyl formation of the above obtained compound of formula 7-2 with suitable reagents.

This reaction is essentially the same as and may be carried out in the same manner as and using the same reagents and reaction conditions as Step 1C in Scheme 1 and Steps 3A and 3B in Scheme 3.

Step 7C

In this Step, the desired compound of formula (I), which is a compound of the present invention, may be prepared by the reacting the compound of formula 7-3, prepared as described in Step 7B with a pyrazole compound formula 7-4 in an inert solvent under conditions known to those skilled in the art (e.g., *Tetrahedron Lett.*, 1998, 39, 2933 and *Tetrahedron Lett.*, 1998, 39, 2941).

The reaction may be normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene, xylene, nitrobenzene, and pyridine; halogenated hydrocarbons, such as methylene chloride, chloroform, carbon tetrachloride and dichloroethane; ethers, such as diethyl ether, diisopropyl ether, tetrahydrofuran and dioxane; ethylacetate, aceronitrile, N,N-dimethylformamide, dimethylsulfoxide. Of these solvents, the halogenated hydrocarbons and pyridine are preferred.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −100° C. to 250° C., more preferably from 0° C. to the reflux temperature. The time required for the reaction may also vary widely, depending on many factors, notably the reaction temperature and the nature of the reagents and solvent employed. However, provided that the reaction may be effected under the preferred conditions outlined above, a period of from 1 minute to 10 day, more preferably from 20 minutes to 5 days, will usually suffice.

This reaction may be carried out in the presence a suitable catalyst. There is likewise no particular restriction on the nature of the catalysts used, and any catalysts commonly used in reactions of this type may equally be used here. Examples of such catalysts include: tetrakis(triphenylphosphine)-palladium, bis(triphenylphosphine)palladium(II) chloride, copper(0), copper(I) acetate, copper(I) bromide, copper(I) chloride, copper(I) iodide, copper(I) oxide, copper(II) trifluoromethanesulfonate, copper(II) acetate, copper(II) bromide, copper(II) chloride, copper(II) iodide, copper(II) oxide, copper(II) trifluoromethanesulfonate palladium(II) acetate, palladium(II) chloride, bisacetonitriledichloropalladium(0), bis(dibenzylideneacetone)palladium(0), tris(dibenzylideneacetone)dipalladium(0) or [1,1'-bis(diphenylphosphino)ferrocene]palladium(II) dichloride.

This reaction may be carried out in the presence of a suitable additive agent. Examples of such additive agents include: triphenylphosphine, tri-tert-butylphosphine, 1,1'-bis(diphenylphosphino)ferrocene, tri-2-furylphosphine, tri-o-tolyephosphine, 2-(dichlorohexylphosphino)biphenyl or triphenylarsine.

This reaction may be carried out in the presence or absence of a base. There is likewise no particular restriction on the nature of the bases used, and any base commonly used in reactions of this type may equally be used here. Examples of such bases include: lithium hydroxide, sodium hydroxide, potassium hydroxide, barium hydroxide, sodium carbonate, potassium carbonate, cesium carbonate, thallium(I) carbonate, sodium ethoxide, potassium tert-butoxide, potassium acetate, cesium fluoride, tetrabutylammonium fluoride, tetrabutylammonium chloride, tetrabutylammonium iodide, pyridine, 1,8-diazabicyclo[5.4.0]undecan, picoline, 4-(N,N-dimethylamino)pyridine, triethylamine, tributylamine, diisopropylethylamine, N-methylmorphorine and N-methylpiperidine.

This reaction may be carried out in the presence or absence of a dehydrating reagent. There is likewise no particular restriction on the nature of the dehydrating reagents used, and any dehydrating reagents commonly used in reactions of this type may equally be used here. Examples of such dehydrating reagents include: molecular sieves.

Step 7D

In this Step, the desired compound of formula 7-5 may be prepared by the reacting the compound of formula 7-2, prepared as described in Step 7A with a pyrazole compound formula 7-4 in an inert solvent.

This reaction is essentially the same as and may be carried out in the same manner as and using the same reagents and reaction conditions as Step 7C in Scheme 7.

Step 7E

In this Step, the desired compound of formula (1), which is a compound of the present invention, may be prepared from the compound of formula 7-5, prepared as described in Step 7D in an inert solvent.

This reaction is essentially the same as and may be carried out in the same manner as and using the same reagents and reaction conditions as Step 1C in Scheme 1 and Steps 3A and 3B in Scheme 3.

Compounds of formula 7-1 and 7-4 may be a known compound or readily prepared by known methods.

In the above Schemes from 1 to 7, examples of suitable solvents include a mixture of any two or more of those solvent described in each Step.

The optically active compounds of this invention can be prepared by several methods. For example, the optically active compounds of this invention may be obtained by chromatographic separation, enzymatic resolution or fractional crystallization from the final compounds.

Several compounds of this invention possess an asymmetric center. Hence, the compounds can exist in separated (+)- and (−)-optically active forms, as well as in racemic one thereof. The present invention includes all such forms within its scope. Individual isomers can be obtained by known methods, such as optically selective reaction or chromatographic separation in the preparation of the final product or its intermediate.

The subject invention also includes isotopically-labelled compounds, which are identical to those recited in formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, pharmaceutically acceptable esters of said compounds and pharmaceutically acceptable salts of said compounds, of said esters or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assay. Tritiated, i.e., $^3H$, and carbon-14, i.e., $^{14}C$, isotopes are particularly preferred for their ease of presentation and detectability. Further, substitution with heavier isotopes such as deuterium, i.e., $^2H$, can afford therapeutic advantage resulting from greater metabolic stability, for example increased in vivo half-life or reduced dosage requirement and, hence, may be preferred in some circumstances. Isotopically labeled compounds of formula (I) of this invention and prodrugs thereof can generally be prepared by carrying out the procedure disclosed in above-disclosed Schemes and/or Examples and Preparations below, by submitting a readily available isotopically labeled reagent for a non-isotopically labeled reagent.

The present invention includes acid addition and base salt forms of the compounds (I).

Certain compounds of the present invention are capable of forming pharmaceutically acceptable non-toxic cations. Pharmaceutically acceptable non-toxic cations of compounds of formula (I) may be prepared by conventional techniques by, for example, contacting said compound with a stoichiometric amount of an appropriate alkali or alkaline earth metal (sodium, potassium, calcium and magnesium) hydroxide or alkoxide in water or an appropriate organic solvent such as ethanol, isopropanol, mixtures thereof, or the like.

The bases which are used to prepare the pharmaceutically acceptable base addition salts of the acidic compounds of this invention of formula (I) are those which form non-toxic base addition salts, i.e., salts containing pharmaceutically acceptable cations, such as adenine, arginine, cytosine, lysine, benethamine (i.e., N-benzyl-2-phenyletylamine), benzathine(i.e., N,N-dibenzylethylenediamine), choline, diolamine (i.e., diethanolamine), ethylenediamine, glucosamine, glycine, guanidine, guanine, meglumine (i.e., N-methylglucamine), nicotinamide, olamine (i.e., ethanolamine), ornithine, procaine, proline, pyridoxine, serine, tyrosine, valine and tromethamine(i.e., tris or tris (hydroxymethyl)aminomethane). The base addition salts can be prepared by conventional procedures.

Insofar as the certain compounds of this invention are basic compounds, they are capable of forming a wide variety of different salts with various inorganic and organic acids.

The acids which are used to prepare the pharmaceutically acceptable acid addition salts of the basic compounds of this invention of formula (I) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, malate, fumarate, gluconate, saccharate, benzoate, methanesulfonate, ethanesulfonate, benzenesulfonate, p-toluenesulfonate, adipate, aspartate camsylate, (i.e., 1,2-ethanedisulfontate), estolate (i.e., laurylsulfate), gluceptate (i.e., gluscoheptonate), gluconate, 3-hydroxy-2-naphthoate, xionofoate (i.e., 1-hydrroxy-2-naphthoate), isethionate, (i.e., 2-hydroxyethanesulfonate), mucate (i.e., galactarate), 2-naphsylate (i.e., naphthalenesulphonate, stearate, cholate, glucuronate, glutamate, hippurate, lactobionate, lysinate, maleate, mandelate, napadisylate, nicatinate, polygalacturonate, salicylate, sulphosalicylate, tannate, tryptophanate, borate, carbonate, oleate, phthalate and pamoate (i.e., 1.1'-methylene-bis-(2-hydroxy-3-naphthoate). The acid addition salts can be prepared by conventional procedures.

Also included within the scope of this invention are bioprecursors (also called pro-drugs) of the compounds of the formula (I). A bioprecursor of a compound of the formula (I) is a chemical derivative thereof which is readily converted back into the parent compound of the formula (I) in biological systems. In particular, a bioprecursor of a compound of the formula (I) is converted back to the parent compound of the formula (I) after the bioprecursor has been administered to, and absorbed by, a mammalian subject, e.g., a human subject. For example, it is possible to make a bioprecursor of the compounds of formula (I) in which one or both of L and W include hydroxy groups by making an ester of the hydroxy group. When only one of L and W includes hydroxy group, only mono-ester are possible. When both L and W include hydroxy, mono- and di-esters (which can be the same or different) can be made. Typical esters are simple alkanoate esters, such as acetate, propionate, butyrate, etc. In addition, when L or W includes a hydroxy group, bioprecursors can be made by converting the hydroxy group to an acyloxymethyl derivative (e.g., a pivaloyloxymethyl derivative) by reaction with an acyloxymethyl halide (e.g., pivaloyloxymethyl chloride).

When the compounds of the formula (I) of this invention may form solvates such as hydrates, such solvates are included within the scope of this invention.

Also, the compounds of formula (I) may be expected more effective therapeutic effects with being co-administered with a COX-2 selective NSAID.

Further, the present invention also encompasses a combination, including a pharmaceutical composition, for the treatment of inflammation, rheumatoid arthritis, pain, common cold, osteoarthritis, neuropathic pain, brain tumor, diuresis, or the like, which comprises a therapeutically effective amount of a compound of formula (I) or salt or ester thereof and a COX-2 selective NSAID.

The compounds of the invention may advantageously be employed in combination with one or more other therapeutic ingredients selected from, a COX-2 selective, COX-1 selective or non-selective NSAIDs, opioids, anticonvulsants, antidepressants, local anesthetics, disease-modifying anti-rheumatoid drugs, or steroid.

The combination with a COX-2 selective NSAID is particularly favourured for use in the prophylaxis and treatment of pain and arthritis. Examples of a COX-2 selective NSAID are nimesulide, celecoxib, rofecoxib and valdecoxib.

The compounds of Formula (I) have been found to possess an activity as prostaglandin $E_2$ receptor antagonist, preferably as $EP_4$ receptor antagonist. Preferably, these compounds are useful as an analgesic, anti-inflammatory, diuretic, and the like, in mammalian subjects, especially humans in need of such agents. The affinity, antagonist activities and analgesic activity can be demonstrated by the following tests respectively.

Method for Assessing Biological Activities
In Vitro Assays
Rat EP Receptor Cell Membrane Binding Assay:
Stable Expression of Rat EP1, 2, 3 and 4 Receptors in the Human Embryonic Kidney (HEK293) Cell Line The cDNA clones of rat EP1, 2, 3 and 4 receptors are obtained by polymerase chain reaction (PCR) from rat kidney or heart cDNA libraries (Clontech). Human embryonic kidney cells (HEK 293) are stably transfected with expression vectors for rat EP1, 2, 3 and 4 receptors in according to the method described in the article; the journal of biological chemistry vol.271 No.39, pp23642–23645.

Preparation of Membrane Fraction:

The EP1, 2, 3 and 4 transfectant are grown in Dulbecco's modified Eagle's medium containing 10% fetal calf serum, 100 U/ml penicillin, 100 µg/ml streptomycin and 600 µg/ml G418 (selection medium) at 37° C. in a humidified atmosphere of 5% $CO_2$ in air. For the membrane preparation, cells are harvested with phosphate buffered saline (PBS) and centrifuged at 400×g for 5 min. The pellet is suspended with child (4° C.) PBS containing 1 mM Pefabloc (4-(2-aminoethyl)-benzenesulfonyl fluoride (AEBSF)), 10 µM Phosphoramidon, 1 µM Pepstatin A, 10 µM Elastatinal, 100 µM Antipain. Cells are lysed with ultrasonic cell disrupter for 20-sec sonication. Then cell mixtures are centrifuged at 45,000×g for 30 minutes. The pellet is resuspended in assay buffer (10 mM 2-morpholinoeth-anesulfonic acid (MES)-KOH, 1 mM etylenediamine tetra-acetic acid (EDTA), 10 mM $MgCl_2$, pH 6.0), and protein concentration is determined by Bradford method (Bio-Rad assay). This membrane preparation is stored at −80° C. freezer until use for binding assay.

Binding Assay:

Membrane Binding Assay

[$^3$H]-$PGE_2$ membrane binding assays are performed in the reaction mixture of 10 mM MES/KOH (pH 6.0), 10 mM $MgCl_2$, 1 mM EDTA, 1 nM [$^3$H]-$PGE_2$ (Amersham TRK431, 164 Ci/mmol), 2~10 µg of protein from membrane fraction (rat EP1, 2, 3 and 4/HEK293 transfectant) and test compound (total volume is 0.1 ml in 96 well polypropylene plate). Incubation is conducted for 60 min at room temperature prior to separation of the bound and free radioligand by rapid filtration through glass fiber filters (Printed Filtermat B, 1205-404, glass fiber, double thickness, size 102×258 mm, Wallac inc., presoaked in 0.2% polyethylenimine). Filters are washed with assay buffer and the residual [$^3$H]-$PGE_2$ bound to the filter is determined by liquid scintillation counter (1205 Betaplate™). Specific binding is defined as the difference between total binding and nonspecific binding which is determined in the presence of 10 µM $PGE_2$.

cAMP Assay in Rat $EP_4$ Transfectant

HEK293 cells expressing rat $EP_4$ receptors ($rEP_4$ cells) are maintained in DMEM containing 10% FCS and 600 µg/ml geneticin. For harvesting $rEP_4$ cells, culture medium is aspirated and cells in 75 cm² flask are washed with 10 ml of phosphate buffered saline (PBS). Another 10 ml of PBS is added to the cells and incubated for 20 min at room temperature. Rat $EP_4$ cells are harvested by pipetting and centrifuged at 300 g for 4 min. Cells are resuspended in DMEM without neutral red at a density of 5×10⁵ cells/ml. The cells (70 µl) are mixed with 70 µl of DMEM (without neutral red) containing 2 mM IBMX (PDE inhibitor), 1 nM $PGE_2$ and test compounds in PCR-tubes, and incubated at 37° C. for 10 min. The reaction is stopped by heating at 100° C. for 10 min with thermal cycler. Concentration of cAMP in reaction mixtures is determined with SPA cAMP Kit (Amersham) according to the manufacture's instruction.

Reference: Eur. J. Pharmacol. 340 (1997) 227–241

In Vivo Assays

Carrageenan Induced Mechanical Hyperalgesia in Rats:

Male 4-week-old SD rats (Japan SLC) were fasted over night. Hyperalgesia was induced by intraplantar injection of λ-carrageenin (0.1 ml of 1% w/v suspension in saline, Zushikagaku). The test compounds (1 ml of 0.1% methylcellulose/100 g body weight) were given per orally at 5.5 hours after the carrageenin injection. The mechanical pain threshold was measured by analgesy meter (Ugo Basile) at 4, 5, 6.5 and 7.5 hours after the carrageenin injection and the change of pain threshold was calculated.

Reference: Randall L. O. & Selitto I. J., Arch. Int. Pharmacodyn. 111, 409–419, 1957

Prostaglandin $E_2$($PGE_2$)—Induced Thermal Hyperalgesia in Rats:

Male 4-week-old SD rats (Japan SLC) were fasted over night. Hyperalgesia was induced by intraplantar injection of 100 ng of PGE2 in 5% DMSO/saline(100 ul) into the right hindpaw of the rats. Animals were given orally or intravenously either vehicle (po: 0.1% methyl cellulose, iv: 10% DMSO/saline) or a test compound 15 or 5 min. prior to $PGE_2$ injection, respectively. Rats were placed in plastic cages of plantar test apparatus (Ugo Basile) and the mobile radiant heat source was focused on right hind paw of the rats. The thermal paw-withdrawal latency (sec.) was measured at 15 min after $PGE_2$ injection and the change in withdrawal threshold was calculated.

Reference: Hargreaves K. et al., Pain 32, 77–88, 1988.

Most of the compounds prepared in the working examples appearing hereafter demonstrate higher affinity for $EP_4$-receptors than for EP1, 2 and 3-receptors.

Pharmaceutically acceptable salts of the compounds of formula (1) include the acid addition and base salts (including disalts) thereof.

Suitable acid addition salts are formed from acids which form non-toxic salts. Examples include the acetate, aspartate, benzoate, besylate, bicarbonate/carbonate, bisulphate, camsylate, citrate, edisylate, esylate, fumarate, gluceptate, gluconate, glucuronate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, palmoate, phosphate, saccharate, stearate, succinate sulphate, D- and L-tartrate, and tosylate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see Stahl and Wermuth, Handbook of Pharmaceutical Salts: Properties, Selection, and Use, Wiley-VCH, Weinheim, Germany (2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent.

Pharmaceutically acceptable solvates in accordance with the invention include hydrates and solvates wherein the solvent of crystallization may be isotopically substituted, e.g. $D_2O$, $d_6$-acetone, $d_6$-DMSO.

Also within the scope of the invention are clathrates, drug-host inclusion complexes wherein, in contrast to the aforementioned solvates, the drug and host are present in non-stoichiometric amounts. For a review of such complexes, see J Pharm Sci, 64 (8), 1269–1288 by Haleblian (August 1975).

Hereinafter all references to compounds of formula (I) include references to salts thereof and to solvates and clathrates of compounds of formula (I) and salts thereof. The invention includes all polymorphs of the compounds of formula (1) as hereinbefore defined.

Also within the scope of the invention are so-called "prodrugs" of the compounds of formula (I). Thus certain derivatives of compounds of formula (I) which have little or no pharmacological activity themselves can, when metabolised upon administration into or onto the body, give rise to compounds of formula (I) having the desired activity. Such derivatives are referred to as "prodrugs".

Prodrugs in accordance with the invention can, for example, be produced by replacing appropriate functionalities present in the compounds of formula (I) with certain moieties known to those skilled in the art as "pro-moieties" as described, for example, in "Design of Prodrugs" by H Bundgaard (Elsevier, 1985).

Finally, certain compounds of formula (I) may themselves act as prodrugs of other compounds of formula (I).

Compounds of formula (I) containing one or more asymmetric carbon atoms can exist as two or more optical isomers. Where a compound of formula (I) contains an alkenyl or alkenylene group, geometric cis/trans (or Z/E) isomers are possible, and where the compound contains, for example, a keto or oxime group, tautomeric isomerism ('tautomerism') may occur. It follows that a single compound may exhibit more than one type of isomerism.

Included within the scope of the present invention are all optical isomers, geometric isomers and tautomeric forms of the compounds of formula (I), including compounds exhibiting more than one type of isomerism, and mixtures of one or more thereof.

Cis/trans isomers may be separated by conventional techniques well known to those skilled in the art, for example, fractional crystallisation and chromatography.

Conventional techniques for the preparation/isolation of individual stereoisomers include the conversion of a suitable optically pure precursor, resolution of the racemate (or the racemate of a salt or derivative) using, for example, chiral HPLC, or fractional crystallisation of diastereoisomeric salts formed by reaction of the racemate with a suitable optically active acid or base, for example, tartaric acid.

The present invention also includes all pharmaceutically acceptable isotopic variations of a compound of formula (I). An isotopic variation is defined as one in which at least one atom is replaced by an atom having the same atomic number, but an atomic mass different from the atomic mass usually found in nature.

Examples of isotopes suitable for inclusion in the compounds of the invention include isotopes of hydrogen, such as $^2$H and $^3$H, carbon, such as $^{13}$C and $^{14}$C, nitrogen, such as $^{15}$N, oxygen, such as $^{17}$O and $^{18}$O, phosphorus, such as $^{32}$P, sulphur, such as $^{35}$S, fluorine, such as $^{18}$F, and chlorine, such as $^{36}$Cl.

Substitution of the compounds of the invention with isotopes such as deuterium, i.e. $^2$H, may afford certain therapeutic advantages resulting from greater metabolic stability, for example, increased in vivo half-life or reduced dosage requirements, and hence may be preferred in some circumstances.

Certain isotopic variations of the compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Isotopic variations of the compounds of formula (I) can generally be prepared by conventional techniques known to those skilled in the art or by processes analogous to those described in the accompanying Examples and Preparations using appropriate isotopic variations of suitable reagents.

The compounds of formula (I) may be freeze-dried, spray-dried, or evaporatively dried to provide a solid plug, powder, or film of crystalline or amorphous material. Microwave or radio frequency drying may be used for this purpose.

The compounds of the invention may be administered alone or in combination with other drugs and will generally be administered as a formulation in association with one or more pharmaceutically acceptable excipients. The term "excipient" is used herein to describe any ingredient other than the compound of the invention. The choice of excipient will to a large extent depend on the particular mode of administration.

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981–986 by Liang and Chen (2001).

The composition of a typical tablet in accordance with the invention may comprise:

| Ingredient | % w/w |
| --- | --- |
| Compound of formula (I) | 10.00* |
| Microcrystalline cellulose | 64.12 |
| Lactose | 21.38 |
| Croscarmellose sodium | 3.00 |
| Magnesium stearate | 1.50 |

*Quantity adjusted in accordance with drug activity.

A typical tablet may be prepared using standard processes known to a formulation chemist, for example, by direct compression, granulation (dry, wet, or melt), melt congealing, or extrusion. The tablet formulation may comprise one or more layers and may be coated or uncoated.

Examples of excipients suitable for oral administration include carriers, for example, cellulose, calcium carbonate, dibasic calcium phosphate, mannitol and sodium citrate, granulation binders, for example, polyvinylpyrrolidine, hydroxypropylcellulose, hydroxypropylmethylcellulose and gelatin, disintegrants, for example, sodium starch glycolate and silicates, lubricating agents, for example, magnesium stearate and stearic acid, wetting agents, for example, sodium lauryl sulphate, preservatives., anti-oxidants, flavours and colourants.

Solid formulations for oral administration may be formulated to be immediate and/or modified release. Modified release formulations include delayed-, sustained-, pulsed-, controlled dual-, targeted and programmed release. Details of suitable modified release technologies such as high energy dispersions, osmotic and coated particles are to be found in Verma et al, Pharmaceutical Technology On-line, 25(2), 1–14 (2001). Other modified release formulations are described in U.S. Pat. No. 6,106,864.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by suitable processing, for example, the use of high energy spray-dried dispersions (see WO 01/47495) and/or by the use of appropriate formulation techniques, such as the use of solubility-enhancing agents.

Formulations for parenteral administration may be formulated to be immediate and/or modified release. Modified release formulations include delayed-, sustained-, pulsed-, controlled dual-, targeted and programmed release.

Topical Administration

The compounds of the invention may also be administered topically to the skin or mucosa, either dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin and propylene glycol. Penetration enhancers may be incorporated—see, for example, J Pharm Sci, 88 (10), 955–958 by Finnin and Morgan (October 1999).

Other means of topical administration include delivery by iontophoresis, electroporation, phonophoresis, sonophoresis and needle-free or microneedle injection. Formulations for topical administration may be formulated to be immediate and/or modified release. Modified release formulations include delayed-, sustained-, pulsed-, controlled dual-, targeted and programmed release. Thus compounds of the invention may be formulated in a more solid form for administration as an implanted depot providing long-term release of the active compound.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids) from a dry powder inhaler or as an aerosol spray from a pressurised container, pump, spray, atomiser (preferably an atomiser using electrohydrodynamics to produce a fine mist), or nebuliser, with or without the use of a suitable propellant, such as dichlorofluoromethane.

The pressurised container, pump, spray, atomizer, or nebuliser contains a solution or suspension of the active compound comprising, for example, ethanol (optionally, aqueous ethanol) or a suitable alternative agent for dispersing, solubilising, or extending release of the active, the propellant(s) as solvent and an optional surfactant, such as sorbitan trioleate or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

A suitable solution formulation for use in an atomiser using electrohydrodynamics to produce a fine mist may contain from 1 $\mu$g to 10 mg of the compound of the invention per actuation and the actuation volume may vary from 1 $\mu$l to 100 $\mu$l. A typical formulation may comprise a compound of formula (I), propylene glycol, sterile water, ethanol and sodium chloride. Alternative solvents which may be used instead of propylene glycol include glycerol and polyethylene glycol.

Capsules, blisters and cartridges (made, for example, from gelatin or HPMC) for use in an inhaler or insufflator may be formulated to contain a powder mix of the compound of the invention, a suitable powder base such as lactose or starch and a performance modifier such as l-leucine, mannitol, or magnesium stearate.

In the case of dry powder inhalers and aerosols, the dosage unit is determined by means of a valve which delivers a metered amount. Units in accordance with the invention are typically arranged to administer a metered dose or "puff".

Formulations for inhaled/intranasal administration may be formulated to be immediate and/or modified release. Modified release formulations include delayed-, sustained-, pulsed-, controlled dual-, targeted and programmed release.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled dual-, targeted and programmed release.

Ocular/Andial Administration

The compounds of the invention may also be administered directly to the eye or ear, typically in the form of drops of a micronised suspension or solution in isotonic, pH-adjusted, sterile saline. Other formulations suitable for ocular and andial administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/andial administration may be formulated to be immediate and/or modified release. Modified release formulations include delayed-, sustained-, pulsed-, controlled dual-, targeted, or programmed release.
Enabling Technologies The compounds of the invention may be combined with soluble macromolecular entities such as cyclodextrin or polyethylene glycol-containing polymers to improve their solubility, dissolution rate, taste-masking, bioavailability and/or stability. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Dosage

The compounds of the invention can be administered via either the oral, parenteral or topical routes to mammals. In general, these compounds are most desirably administered to humans in doses ranging from 0.1 mg to 3000 mg, preferably from 1 mg to 500 mg, which may be administered in a single dose or in divided doses throughout the day, although variations will necessarily occur depending upon the weight and condition of the subject being treated, the disease state being treated and the particular route of administration chosen.

These dosages are based on an average human subject having a weight of about 65 to 70 kg. The physician will readily be able to determine doses for subjects whose weight falls outside this range, such as infants and the elderly.

For example, a dosage level that is in the range of from 0.01 mg to 10 mg per kg of body weight per day is most desirably employed for treatment of pain associated with inflammation.

EXAMPLES

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath temperature of up to 60° C.; reactions were monitored by thin layer chromatography (TLC) and reaction times are given for illustration only; melting points (mp) given are uncorrected (polymorphism may result in different melting points); the structure and purity of all isolated compounds were assured by at least one of the following techniques: TLC (Merck silica gel 60 $F_{254}$ precoated TLC plates), mass spectrometry, nuclear magnetic resonance (NMR), infrared absorption spectra (IR) or microanalysis. Yields are given for illustrative purposes only. Flash column chromatography was carried out using Merck silica gel 60 (230–400 mesh ASTM). Low-resolution mass spectral data (EI) were obtained on a Automass 120 (JEOL) mass spectrometer. Low-resolution mass spectral data (ESI) were obtained on a Quattro II (Micromass) mass spectrometer or a ZMD (Micromass). NMR data was determined at 270 MHz (JEOL JNM-LA 270 spectrometer) or 300 MHz (JEOL JNM-LA300 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, quint=quintet, m=multiplet, br.=broad, etc. IR spectra were measured by a Shimazu infrared spectrometer (IR-470). Chemical symbols have their usual meanings; bp (boiling point), mp (melting point), L (liter(s)), mL (milliliter(s)), g (gram(s)), mg (milligram(s)), mol (moles), mmol (millimoles), eq. (equivalent(s)), quant. (quantitative yield).

Analytical condition for LC-MS (Waters LC-MS system (LC as 2690, ZMD as MS)): Column YMC CombiScreen basic 4.6 mm×50 mm, Flow rate 1 mL-min.; Mobile phase 20% MeOH/80% 0.1%HCO$_2$H in H$_2$O programmed over 5 min to 90% MeOH/10% 0.1%HCO$_2$H in H$_2$O. Hold for 5 min.; Wave length 220–400 nm. MS detector ApcI Cone 30 Volts.

Example 1

2-{4-[5-Phenyl-3-(trifluoromethyl)-1H-pyrazol-1-yl] phenyl}ethyl (4-Methylphenyl)sulfonylcarbamate Step 1. 2-{4-[5-Phenyl-3-(trifluoromethyl)-1H-pyrazol-1-yl]phenyl}ethanol A mixture of 2-(4-hydrazinophenyl)ethanol hydrochloride (*J. Med. Chem.*, 1999, 42, 2504, 202 mg, 1.07 mmol) and benzoyl-1,1,1-trifluoroacetone (278 mg, 1.28 mmol) in ethanol (13 mL) was heated under reflux overnight. After removal of the solvent, the resulting residue was partitioned between dichloromethane and water. Organic phase was washed with brine and dried (Na$_2$SO$_4$). After removal of the solvent, the crude product was purified by TLC with hexane/ethyl acetate (1:1) to afford 200 mg (56%) of the title compound as yellow solids: MS (ESI) m/z 333 [M+H]$^+$, $^1$H-NMR (CDCl$_3$) δ 7.36–7.20 (9H, m), 6.74 (1H, s), 3.86 (2H, br.s), 2.89 (2H, t, J=6.6 Hz).

Step 2. 2-{4-[5-Phenyl-3-(trifluoromethyl)-1H-pyrazol-1-yl]phenyl}ethyl (4-methylphenyl)sulfonylcarbamate To a solution of 2-{4-[5-phenyl-3-(trifluoromethyl)-1H-pyrazol-1-yl]phenyl}ethanol (step 1, 158 mg, 0.48 mmol) in dichloromethane (10 ml) was added p-toluenesulfonyl isocyanate (114 mg, 0.58 mmol). The resulting mixture was stirred at room temperature for 30 min. The reaction mixture washed with water and the organic phase was dried (Na$_2$SO$_4$). After removal of the solvent, the crude product was purified by TLC with toluene/ethanol (10:1) to afford 184 mg (73%) of the title compound as yellow solids: MS (ESI) m/z 530 [M+H]$^+$, 528 [M–H]$^-$, $^1$H-NMR (CDCl$_3$) δ 7.87–7.80 (3H, m), 7.36–7.09 (10H, m), 6.75 (1H, s), 4.28 (2H, t, J=6.1 Hz), 2.91 (2H, t, J=6.9 Hz), 2.42 (3H, s).

Example 2

2-[4-(3,5-Dimethyl-4-phenyl-1H-pyrazol-1-yl) phenyl]ethyl (4-methylphenyl)sulfonylcarbamate Step 1. 2-[4-(3,5-Dimethyl-4-phenyl-1H-pyrazol-1-yl) phenyl]ethanol The title compound was prepared according to the procedure described in step 1 of Example 1 from 2-(4-hydrazinophenyl)ethanol hydrochloride and 3-phenylpentane-2,4-dione: MS (ESI) m/z 293 [M+H]$^+$, $^1$H-NMR (CDCl$_3$) δ 7.45–7.27 (9H, m), 3.79 (2H, t, J=6.6 Hz), 2.87 (2H, t, J=6.6 Hz), 2.32 (3H, s), 2.26 (3H, s).

Step 2. 2-[4-(3,5-Dimethyl-4-phenyl-1H-pyrazol-1-yl) phenyl]ethyl (4-methylphenyl)sulfonylcarbamate The title compound was prepared according to the procedure described in step 2 of Example 1 from 2-[4-(3,5-dimethyl-4-phenyl-1H-pyrazol-1-yl)phenyl]ethanol (step 1): MS (ESI) m/z 490 [M+H]$^+$, 488 [M–H]$^-$, $^1$H-NMR (CDCl$_3$) δ 7.90 (2H, d, J=7.3 Hz), 7.46–7.17 (11H, m), 4.25 (2H, t, J=6.8 Hz), 2.89 (2H, t, J=6.8 Hz), 2.41 (3H, s), 2.33 (3H, s), 2.26 (3H, s).

Example 3

2-[4-(5-Methyl-3-phenyl-1H-pyrazol-1-yl)phenyl] ethyl (4-methylphenyl)sulfonylcarbamate

Step 1. 2-[4-(5-Methyl-3-phenyl-1H-pyrazol-1-yl)phenyl] ethanol and 2-[4-(3-Methyl-5-phenyl-1H-pyrazol-1-yl)phenyl]ethanol The title compounds were prepared according to the procedure described in step 1 of Example 1 from 2-(4-hydrazinophenyl)ethanol hydrochloride and benzoylacetone: 2-[4-(5-Methyl-3-phenyl-1H-pyrazol-1-yl)phenyl]ethanol; MS (ESI) m/z 279 [M+H]$^+$, $^1$H-NMR (CDCl$_3$) δ 7.86–7.83 (2H, m), 7.47–7.26 (7H, m), 6.52 (1H, s), 3.88 (2H, t. J=6.6 Hz), 2.92 (2H, t, J=6.6 Hz), 2.37 (3H, s): 2-[4-(3-Methyl-5-phenyl-1H-pyrazol-1-yl)phenyl]ethanol; MS (ESI) m/z 279 [M+H]$^+$, $^1$H-NMR (CDCl$_3$) δ 7.86–7.83 (2H, m), 7.47–7.26 (7H, m), 6.52 (1H, s), 3.88 (2H, t, J=6.6 Hz), 2.92 (2H, t, J=6.6 Hz), 2.37 (3H, s).

Step 2. 2-[4-(5-Methyl-3-phenyl-1H-pyrazol-1-yl)phenyl] ethyl (4-methylphenyl)sulfonylcarbamate The title compound was prepared according to the procedure described in step 2 of Example 1 from 2-[4-(5-methyl-3-phenyl-1H-pyrazol-1-yl)phenyl]ethanol (step 1): MS (ESI) m/z 476 [M+H]$^+$, 474 [M–H]$^-$, $^1$H-NMR (CDCl$_3$) δ 7.90–7.82 (4H, m), 7.42–7.16 (9H, m), 6.52 (1H, s), 4.29 (2H, t, J=6.8 Hz), 2.93 (2H, t, J=6.8 Hz), 2.42 (3H, s), 2.36 (3H, s).

Example 4

2-[4-(4-Butyl-3,5-dimethyl-1H-pyrazol-1-yl)phenyl] ethyl(4-methylphenyl)sulfonylcarbamate

Step 1. 2-[4-(4-Butyl-3,5-dimethyl-1H-pyrazol-1-yl)phenyl] ethanol

The title compound was prepared according to the procedure described in step 1 of Example 1 from 2-(4-hydrazinophenyl)ethanol hydrochloride and 3-n-butyl-2,4-pentanedione: MS (ESI) m/z 273 [M+H]$^+$, $^1$H-NMR (CDCl$_3$) δ 7.37–7.26 (4H, m), 3.87 (2H, t, J=6.8 Hz), 2.91 (2H, t, J=6.6 Hz), 2.39 (2H, t, J=7.6 Hz), 2.25 (3H, s), 2.22 (3H, s), 1.53–1.26 (4H, m), 0.94 (3H, t, J=7.1 Hz).

Step 2. 2-[4-(4-Butyl-3,5-dimethyl-1H-pyrazol-1-yl)phenyl] ethyl(4-methylphenyl)sulfonylcarbamate The title compound was prepared according to the procedure described in step 2 of Example 1 from 2-[4-(4-butyl-3,5-dimethyl-1H-pyrazol-1-yl)phenyl]ethanol (step 1): MS (ESI) m/z 470 [M+H]$^+$, 468 [M–H]$^-$, $^1$H-NMR (CDCl$_3$) δ 7.89 (2H, d, J=8.4 Hz), 7.34–7.30 (4H, m), 7.18 (2H, d, J=8.6 Hz), 4.29 (2H, t, J=6.9 Hz), 2.92 (2H, t, J=6.9 Hz), 2.43 (3H, s), 2.42 (2H, t, J=7.7 Hz), 2.25 (3H, s), 2.21 (3H, s), 1.50–1.32 (4H, m), 1.24 (3H, t, J=7.1 Hz).

Example 5

2-[4-(4-Ethyl-3,5-dimethyl-1H-pyrazol-1-yl)phenyl] ethyl(4-methylphenyl)sulfonylcarbamate

Step 1. 2-[4-(4-Ethyl-3,5-dimethyl-1H-pyrazol-1-yl)phenyl] ethanol

The title compound was prepared according to the procedure described in step 1 of Example 1 from 3-ethyl-2,4-pentanedione and 2-(4-hydrazinophenyl)ethanol hydrochloride: MS (ESI) m/z 245 [M+H]$^+$, $^1$H-NMR (CDCl$_3$) δ 7.36–7.26 (4H, m), 3.84 (2H, t, J=6.6 Hz), 2.89 (2H, t, J=6.6 Hz), 2.24 (2H, q, J=7.5 Hz), 2.26 (3H, s), 2.22 (3H, s), 1.12 (3H, t, J=7.5 Hz).

Step 2. 2-[4-(4-Ethyl-3,5-dimethyl-1H-pyrazol-1-yl)phenyl] ethyl (4-methylphenyl)sulfonylcarbamate The title compound was prepared according to the procedure described in step 2 of Example 1 from 2-[4-(4-ethyl-3,5-dimethyl-1H-pyrazol-1-yl)phenyl]ethanol (step 1): MS (ESI) m/z 442 [M+H]$^+$, 440 [M–H]$^-$, $^1$H-NMR (CDCl$_3$) δ 7.87 (2H, d, J=8.3 Hz), 7.32–7.25 (4H, m), 7.14 (2H, d, J=8.3 Hz), 4.25 (2H, t, J=6.8 Hz), 2.88 (2H, t, J=6.8 Hz), 2.42 (2H, q, J=7.5 Hz), 2.42 (3H, s), 2.26 (3H, s), 2.20 (3H, s), 1.12 (3H, t, J=7.5 Hz).

Example 6

2-[3-(3,5-Dimethyl-4-phenyl-1H-pyrazol-1-yl) phenyl]ethyl(4-methylphenyl)sulfonylcarbamate

Step 1. 2-[3-(3,5-Dimethyl-4-phenyl-1H-pyrazol-1-yl) phenyl]ethanol

The title compound was prepared according to the procedure described in step 1 of Example 1 from 3-phenyl-2,4-pentanedione and 2-(3-hydrazinophenyl)ethanol (WO 94/07896) hydrochloride: MS (ESI) m/z 293 [M+H]$^+$, $^1$H-NMR (CDCl$_3$) δ 7.44–7.22 (9H, m), 3.87 (2H, t, J=6.0 Hz), 2.67 (2H, t, J=6.0 Hz), 2.33 (3H, s), 2.15 (3H, s).

Step 2. 2-[3-(3,5-Dimethyl-4-phenyl-1H-pyrazol-1-yl) phenyl]ethyl(4-methylphenyl)sulfonylcarbamate The title compound was prepared according to the procedure described in step 2 of Example 1 from 2-[3-(3,5-dimethyl-4-phenyl-1H-pyrazol-1-yl)phenyl]ethanol (step 1): MS (ESI) m/z 490 [M+H]$^+$, 488 [M–H]$^-$, $^1$H-NMR (CDCl$_3$) δ 7.85 (2H, d, J=8.4 Hz), 7.47–7.26 (10H, m), 7.14 (1H, d, J=8.8 Hz), 4.28 (2H, t, J=6.6 Hz), 2.91 (2H, t, J=6.6 Hz), 2.41 (3H, s), 2.33 (3H, s), 2.27 (3H, s).

Example 7

2-{4-[5-Amino-4-phenyl-3-(trifluoromethyl)-1H-pyrazol-1-yl]phenyl}ethyl(4-methylphenyl) sulfonylcarbamate

Step 1. 2-{4-[5-Amino-4-phenyl-3-(trifluoromethyl)-1H-pyrazol-1-yl]phenyl}ethanol The title compound was prepared according to the procedure described in step 1 of Example 1 from 2-(4-hydrazinophenyl)ethanol hydrochloride and 2-phenyl-2-(trifluoroacetyl)acetonitrile: MS (ESI) m/z 348 [M+H]$^+$, 346 [M–H]$^-$, $^1$H-NMR (CDCl$_3$) δ 7.58 (2H, J=8.4 Hz), 7.46–7.36 (7H, m), 3.94–3.88 (2H, m), 2.94 (2H, t, J=6.4 Hz).

Step 2. 2-{4-[5-Amino-4-phenyl-3-(trifluoromethyl)-1H-pyrazol-1-yl]phenyl}ethyl (4-methylphenyl) sulfonylcarbamate The title compound was prepared according to the procedure described in step 2 of Example 1 from 2-{4-[5-amino-4-phenyl-3-(trifluoromethyl)-1H-pyrazol-1-yl] phenyl}ethanol (step 1): MS (ESI) m/z 545 [M+H]$^+$, 543 [M–H]$^-$, $^1$H-NMR (CDCl$_3$) δ 7.88 (2H, d, J=8.3 Hz), 7.54–7.26 (11H, m), 4.33 (2H, t, J=8.6 Hz), 3.96 (2H, br.s), 2.97 (2H, t, J=8.6 Hz), 2.43 (3H, s).

Example 8

2-[4-(3-Butyl-5-methyl-4-phenyl-1H-pyrazol-1-yl) phenyl]ethyl(4-methylphenyl)sulfonylcarbamate Mono-sodium Salt

Step 1. 3-Phenyl-2,4-heptanedione

To a stirred mixture of 2,4-octanedione (568 mg, 4.0 mmol) and iodobenzene (408 mg, 2.0 mmol) in dimethylsulfoxide (10 mL) were added copper(I) iodide (380 mg, 2.0 mg) and potassium carbonate (1.10 g, 8.0 mmol). The mixture was heated at 120° C. for 4 h. The mixture was filtered through a pad of Celite and the filtrate was partitioned between ether and water. Organic layer was dried (Na$_2$SO$_4$) and the solvent was removed. The crude product was purified by TLC with hexane/ethyl acetate (4:1) to afford 199 mg (46%) of the title compound as colorless oil: $^1$H-NMR (CDCl$_3$) δ 7.42–7.33 (3H, m), 7.18–7.15 (2H, m), 2.11 (2H, t, J=8.3 Hz), 1.87 (3H, s), 1.58–1.44 (3H, m), 1.25–1.16 (2H, m), 0.79 (3H, t, J=7.2 Hz).

Step 2. 2-[4-(3-Butyl-5-methyl-4-phenyl-1H-pyrazol-1-yl)phenyl]ethanol and 2-[4-(5-Butyl-3-methyl-4-phenyl-1H-pyrazol-1-yl)phenyl]ethanol The title compounds were prepared according to the procedure described in step 1 of Example 1 from 2-(4-hydrazinophenyl)ethanol hydrochloride and 3-phenyl-2,4-heptanedione (step 1): 2-[4-(3-Butyl-5-methyl-4-phenyl-1H-pyrazol-1-yl)phenyl]ethanol; $^1$H-NMR (CDCl$_3$) δ 7.46–7.41 (4H, m), 7.35–7.30 (5H, m), 3.89 (2H, t, J=6.6 Hz), 2.93 (2H, t, J=6.6 Hz), 2.71–2.65 (2H, m), 2.27 (3H, s), 1.59–1.53 (2H, m), 1.36–1.28 (2H, m), 0.85 (3H, t, J=7.4 Hz): 2-[4-(5-Butyl-3-methyl-4-phenyl-1H-pyrazol-1-yl)phenyl]ethanol; $^1$H-NMR (CDCl$_3$) δ 7.46–7.29 (9H, m), 3.93–3.86 (2H, m), 2.94 (2H, t, J=6.4 Hz), 2.71–2.65 (2H, m), 2.28 (3H, s), 1.27–1.21 (2H, m), 1.12–1.04 (2H, m), 0.65 (3H, t, J=7.4 Hz).

Step 3. 2-[4-(3-Butyl-5-methyl-4-phenyl-1H-pyrazol-1-yl)phenyl]ethyl(4-methylphenyl)sulfonylcarbamate The title compound was prepared according to the procedure described in step 2 of Example 1 from 2-[4-(3-butyl-5-methyl-4-phenyl-1H-pyrazol-1-yl)phenyl]ethanol (step 2): MS (ESI) m/z 532 [M+H]$^+$, 530 [M−H]$^−$, $^1$H-NMR (CDCl$_3$) δ 7.90 (2H, d, J=8.3 Hz), 7.46–7.21 (11H, m), 4.30 (2H, t, J=6.9 Hz), 2.94 (2H, t, J=6.9 Hz), 2.68 (2H, dd, J=7.9 Hz), 2.43 (3H, s), 2.25 (3H, s), 1.61–1.56 (2H, m), 1.36–1.28 (2H, m), 0.85 (3H, t, J=7.3 Hz).

Step 4. 2-[4-(3-Butyl-5-methyl-4-phenyl-1H-pyrazol-1-yl)phenyl]ethyl(4-methylphenyl)sulfonylcarbamate Mono-sodium Salt To a solution of 2-[4-(3-butyl-5-methyl-4-phenyl-1H-pyrazol-1-yl)phenyl]ethyl(4-methylphenyl)sulfonylcarbamate (step 3, 14 mg, 0.026 mmol) in methanol (10 mL) was added 2 M aqueous NaOH (13 μL, 0.026 mmol). The resulting mixture was stirred at room temperature for 30 min and concentrated to afford the title compound as white solids: MS (ESI) m/z 532 [M+H]$^+$, 530 [M−H]$^−$.

Example 9

2-[4-(5-Butyl-3-methyl-4-phenyl-1H-pyrazol-1-yl)phenyl]ethyl(4-methylphenyl)sulfonylcarbamate The title compound was prepared according to the procedure described in step 2 of Example 1 from 2-[4-(5-butyl-3-methyl-4-phenyl-1H-pyrazol-1-yl)phenyl]ethanol (step 2 of Example 8): MS (ESI) m/z 532 [M+H]$^+$, 530 [M−H]$^−$, $^1$H-NMR (CDCl$_3$) δ 7.90 (2H, d, J=8.2 Hz), 7.45–7.20 (11H, m), 4.26 (2H, t, J=6.8 Hz), 2.92 (2H, t, J=6.8 Hz), 2.68–2.62 (2H, m), 2.41 (3H, s), 2.28 (3H, s), 1.24–1.16 (2H, m), 1.09–1.01 (2H, m), 0.63 (3H, t, J=7.3 Hz).

Example 10

2-[4-(3,5-Dimethyl-4-phenyl-1H-pyrazol-1-yl)phenyl]ethyl (2-chlorophenyl)sulfonylcarbamate Mono-p-toluenesulfonate Salt Step 1. 2-[4-(3,5-Dimethyl-4-phenyl-1H-pyrazol-1-yl)phenyl]ethyl (2-chlorophenyl)sulfonylcarbamate The title compound was prepared according to the procedure described in step 2 of Example 1 from 2-[4-(3,5-dimethyl-4-phenyl-1H-pyrazol-1-yl)phenyl]ethanol (step 1 of Example 2) and 2-chlorobenzenesulfonyl isocyanate: $^1$H-NMR (CDCl$_3$) δ 8.21 (1H, d, J=7.5 Hz), 7.55–7.20 (12H, m), 4.30 (2H, t, J=6.8 Hz), 2.91 (2H, t, J=6.8 Hz), 2.34 (3H, s), 2.28 (3H, s).

Step 2. 2-[4-(3,5-Dimethyl-4-phenyl-1H-pyrazol-1-yl)phenyl]ethyl (2-chlorophenyl)sulfonylcarbamate mono-p-toluenesulfonate salt The title compound was prepared according to the procedure described in step 6 of Example 15 from 2-[4-(3,5-dimethyl-4-phenyl-1H-pyrazol-1-yl)phenyl]ethyl (2-chlorophenyl)sulfonylcarbamate (step 1): MS (ESI) m/z 510 [M+H]$^+$, 508 [M−H]$^−$.

Example 11

2-{4-[4-(4-Fluorophenyl)-3,5-dimethyl-1H-pyrazol-1-yl]phenyl}ethyl (4-methylphenyl)sulfonylcarbamate Step 1. 2-[4-(3,5-Dimethyl-1H-pyrazol-1-yl)phenyl]ethanol To a suspension of 4-aminophenylethylalcohol (7.27 g, 51.5 mmol) in conc. HCl (100 mL) was added dropwise a solution of sodium nitrate (3.9 g, 56 mmol) in water (100 mL) at −10° C. over 0.5 h. After stirring for 0.5 h, tin(II) chloride dihydrate (29 g, 128 mmol) in conc.HCl (100 mL) was added over 0.5 h and the resulting mixture was allowed to warm to room temperature. The mixture was stirred for 1 h and then added acetylacetone. The reaction mixture was warmed at 100° C. for 5 h. It was basified with aqueous NaOH (pH~10). The mixture was extracted with dichloromethane, dried (Na$_2$SO$_4$), and evaporated to give the title compound quantitatively: MS (ESI) m/z 217 [M+H]$^+$, $^1$H-NMR (CDCl$_3$) δ 7.34–7.24 (4H, m), 5.98 (1H, s), 3.73 (2H, m), 2.84 (2H, m), 2.28 (3H, s), 2.27 (s, 3H).

Step 2. 2-[4-(4-Iodo-3,5-dimethyl-1H-pyrazol-1-yl)phenyl]ethanol

A mixture of 2-[4-(3,5-dimethyl-1H-pyrazol-1-yl)phenyl]ethanol (step 1, 1.26 g, 5.8 mmol), iodine (883 mg, 3.5, mmol) and ceric ammonium nitrate (1.59 g, 2.9 mmol) was stirred in acetonitrile (58 mL) at room temperature for 1 h. Then, the solvent was evaporated under reduced pressure and the resulting residue was dissolved dichloromethane. The organic solution was washed with 5% aqueous solution sodium thiosulfate, then with brine, and finally dried (Na$_2$SO$_4$) and evaporated. The crude product was purified by TLC with hexane/ethyl acetate (1:1) to afford 1.54 g (78%) of the title compound as yellow solids: MS (ESI) m/z 343 [M+H]$^+$, $^1$H-NMR (CDCl$_3$) δ 7.32 (4H, s), 3.86 (2H, t, J=6.6 Hz), 2.91 (2H, t, J=6.6 Hz), 2.33 (3H, s), 2.30 (3H, s), 1.67 (1H, br.s).

Step 3. 2-[4-(4-Iodo-3,5-dimethyl-1H-pyrazol-1-yl)phenyl]ethyl (4-methylphenyl)sulfonylcarbamate The title compound was prepared according to the procedure described in step 2 of Example 1 from 2-[4-(4-iodo-3,5-dimethyl-1H-pyrazol-1-yl)phenyl]ethanol (step 2): MS (ESI) m/z 540 [M+H]$^+$, 538 [M−H]$^−$, $^1$H-NMR (CDCl$_3$) δ 7.89 (2H, d, J=8.4 Hz), 7.31–7.21 (6H, m), 4.29 (2H, t, J=6.9 Hz), 2.93 (2H, t, J=6.9 Hz), 2.43 (3H, s), 2.32 (3H, s), 2.30 (3H, s).

Step 4. 2-{4-[4-(4-Fuorophenyl)-3,5-dimethyl-1H-pyrazol-1-yl]phenyl}ethyl (4-methylphenyl)sulfonylcarbamate To a suspension of 2-[4-(4-iodo-3,5-dimethyl-1H-pyrazol-1-yl)phenyl]ethyl (4-methylphenyl)sulfonylcarbamate (step 3, 500 mg, 0.93 mmol) and 4-fluorobenzeneboronic acid (335 mg, 2.4 mmol) in dimethoxyethane (6.6 mL) were added 2 M aqueous K$_2$CO$_3$ (2.3 mL, 4.65 mmol) and bis(triphenylphosphine) palladium (II) chloride (134 mg, 0.19 mmol), and the mixture was refluxed for 16 h. The mixture was filtered through a pad of Celite and the filtrate was concentrated to give brown oil. It was partitioned between dichloromethane and water. The separated organic layer was dried (Na$_2$SO$_4$), evaporated, and purified by TLC with hexane/ethyl acetate (1:1) to afford 50 mg (11%) of the title compound as white solids: MS (ESI) m/z 508 [M+H]$^+$, 506 [M−H]$^−$, $^1$H-NMR (CDCl$_3$) δ 7.89 (2H, d, J=8.4 Hz), 7.37–7.09 (10H, m), 4.27 (2H, t, J=6.8 Hz), 2.92 (2H, t, J=6.8 Hz), 2.42 (3H, s), 2.30 (3H, s), 2.24 (3H, s).

Example 12

2-{4-[3,5-Dimethyl-4-(4-methylphenyl)-1H-pyrazol-1-yl] phenyl}ethyl (4-methylphenyl) sulfonylcarbamate Mono-ammonium Salt Step 1. 2-{4-[3,5-Dimethyl-4-(4-methylphenyl)-1H-pyrazol-1-yl]phenyl}ethanol To a suspension of 2-[4-(4-iodo-3,5-dimethyl-1H-pyrazol-1-yl)phenyl]ethanol (step 2 of Example 11, 300 mg, 0.88 mmol) and p-tolylboronic acid (313 mg, 2.3 mmol) in dimethoxyethane (6.3 mL) were added 2 M aqueous K$_2$CO$_3$ (2.2 mL, 4.4 mmol) and bis(triphenylphosphine)palladium (II) chloride (124 mg, 0.18 mmol), and the mixture were refluxed for 16 h. The mixture was filtered through a pad of Celite and the filtrate was concentrated to give brown oil. It was partitioned between dichloromethane and water. The separated organic layer was dried (Na$_2$SO$_4$), evaporated, and purified by TLC with hexane/ethyl acetate (1:1) to afford 349 mg (quant.) of the title compound as white solids: MS (ESI) m/z 307 [M+H]$^+$, $^1$H-NMR (CDCl$_3$) δ 7.43–7.20 (8H, m), 3.87 (2H, t, J=6.4 Hz), 2.91 (2H, t, J=6.4 Hz), 2.40 (3H, s), 2.31 (3H, s), 2.28 (3H, s).

Step 2. 2-{4-[3,5-Dimethyl-4-(4-methylphenyl)-1H-pyrazol-1-yl]phenyl}ethyl (4-methylphenyl)sulfonylcarbamate mono-ammonium salt To a solution of 2-{4-[3,5-dimethyl-4-(4-methylphenyl)-1H-pyrazol-1-yl]phenyl}ethanol (step 1, 0.88 mmol) in dichloromethane (10 ml) was added p-toluenesulfonyl isocyanate (221 mg, 1.06 mmol). The resulting mixture was stirred at room temperature for 30 min. The reaction mixture washed with water and the organic phase was dried (Na$_2$SO$_4$). After removal of the solvent, the crude product was purified by TLC with toluene/ethanol (10:1) and SCX eluting with 2 M NH$_3$ methanol solution to afford 155 mg (35%) of the title compound as white solids: MS (ESI) m/z 545 [M+H]$^+$, 543 [M−H]$^−$, $^1$H-NMR [DMSO-d$_6$ (dimethyl-d$_6$ sulfoxide)]δ 7.48 (2H, d, J=8.1 Hz), 7.32–7.20 (4H, m), 7.27–7.10 (4H, m), 7.07–7.04 (2H, d, J=8.1 Hz), 3.80 (2H, t, J=6.8 Hz), 2.69 (2H, t, J=6.8 Hz), 2.23 (3H, s), 2.19 (3H, s), 2.14 (3H, s), 2.09 (3H, s).

Example 13

2-{4-[4-(4-Chlorophenyl)-3,5-dimethyl-1H-pyrazol-1-yl]phenyl}ethyl (4-methylphenyl) sulfonylcarbamate Step 1. 2-{4-[4-(4-Chlorophenyl)-3,5-dimethyl-1H-pyrazol-1-yl]phenyl}ethanol The title compound was prepared according to the procedure described in step 1 of Example 12 from 2-[4-(4-iodo-3,5-dimethyl-1H-pyrazol-1-yl)phenyl]ethanol (step 2 of Example 11) and 4-chlorobenzeneboronic acid: MS (ESI) m/z 327 [M+H]$^+$, $^1$H-NMR (CDCl$_3$) δ 7.44–7.24 (8H, m), 3.89 (2H, t, J=6.6 Hz), 2.93 (2H, t, J=6.6 Hz), 2.31 (3H, s), 2.28 (3H, s).

Step 2. 2-{4-[4-(4-Chlorophenyl)-3,5-dimethyl-1H-pyrazol-1-yl]phenyl}ethyl (4-methylphenyl)sulfonylcarbamate The title compound was prepared according to the procedure described in step 2 of Example 1 from 2-{4-[4-(4-chlorophenyl)-3,5-dimethyl-1H-pyrazol-1-yl] phenyl}ethanol (step 1): MS (ESI) m/z 524 [M+H]$^+$, 522 [M−H]$^−$, $^1$H-NMR (CDCl$_3$) δ 7.89 (2H, d, J=8.4 Hz), 7.42–7.19 (10H, m), 4.27 (2H, t, J=6.8 Hz), 2.91 (2H, t, J=6.8 Hz), 2.42 (3H, s), 2.30 (3H, s), 2.25 (3H, s).

Example 14

N-[({2-[4-(3,5-Dimethyl-4-phenyl-1H-pyrazol-1-yl) phenyl]ethyl}amino)carbonyl]-4-methylbenzenesulfonamide Step 1. 1-[4-(2-Chloroethyl)phenyl]-3,5-dimethyl-4-phenyl-1H-pyrazole To a solution of 2-[4-(3,5-dimethyl-4-phenyl-1H-pyrazol-1-yl)phenyl]ethanol (step 1 of Example 2, 100 mg, 0.34 mmol) in toluene (3 mL) and chloroform (1 mL) was added thionyl chloride (50 μL, 0.68 mmol), and the resulting mixture was stirred at 80° C. for 3h. The reaction mixture was quenched by 2 M NaOH aq. and extracted with dichloromethane. Organic layer was dried (Na$_2$SO$_4$) and the solvent was evaporated to give the title compound as brown solids (quant.): MS (ESI) m/z 311 [M+H]$^+$, $^1$H-NMR (CDCl$_3$) δ 7.46–7.31 (9H, m), 3.74 (2H, t, J=7.3 Hz), 3.12 (2H, t, J=7.3 Hz), 2.34 (3H, s), 2.30 (3H, s).

Step 2. 1-[4-(2-Azidoethyl)phenyl]-3,5-dimethyl-4-phenyl-1H-pyrazole

To a stirred solution of 1-[4-(2-chloroethyl)phenyl]-3,5-dimethyl-4-phenyl-1H-pyrazole (step 1, 0.34 mmol) and KI (56 mg, 0.34 mmol) in N,N-dimethylformamide (2.7 mL) was added sodium azide (44 mg, 0.68 mmol), and then the resulting mixture was stirred for 6 h at 100° C. The reaction mixture was poured into water (100 mL), and extracted with ethyl acetate/toluene (4:1). The organic layer was washed with water (50 mL) and brine (50 mL), then dried (Na$_2$SO$_4$). After removal of the solvent, the crude product was purified by TLC with hexane/ethyl acetate (1:1) to afford 87 mg (81%) of the title compound as yellow oil: $^1$H-NMR (CDCl$_3$) δ 7.46–7.29 (9H, m), 3.55 (2H, t, J=7.3 Hz), 2.96 (2H, t, J=7.1 Hz), 2.34 (3H, s), 2.30 (3H, s).

Step 3. 2-[4-(3,5-Dimethyl-4-phenyl-1H-pyrazol-1-yl) phenyl]ethylamine

To a solution of 1-[4-(2-azidoethyl)phenyl]-3,5-dimethyl-4-phenyl-1H-pyrazole (step 2, 196 mg, 0.62 mmol) in methanol (10 mL) was added Lindlar catalyst (100 mg). The resulting mixture was stirred for 5 h under hydrogen atmosphere. The mixture was filtered through a pad of Celite and the filtrate was concentrated to give 166 mg (92%) of the title compound as colorless oil: MS (ESI) m/z 292 [M+H]$^+$, $^1$H-NMR (CDCl$_3$) δ 7.47–7.39 (4H, m), 7.34–7.29 (5H, m), 3.01 (2H, t, J=6.8 Hz), 2.81 (2H, t, J=6.8 Hz), 2.34 (3H, s), 2.30 (3H, s).

Step 4. N-[({2-[4-(3,5-Dimethyl-4-phenyl-1H-pyrazol-1-yl) phenyl]ethyl}amino) carbonyl]-4-methylbenzenesulfonamide To a solution of 2-[4-(3,5-dimethyl-4-phenyl-1H-pyrazol-1-yl)phenyl]ethylamine (step 3, 166 mg, 0.57 mmol) in dichloromethane (10 ml) was added p-toluenesulfonyl isocyanate (135 mg, 0.68 mmol). The resulting mixture was stirred at room temperature for 30 min. The reaction mixture washed with water and the organic phase was dried (Na$_2$SO$_4$). After removal of the solvent, the crude product was purified by TLC with dichloromethane/methanol (10:1) to afford 110 mg (39%) of the title compound as yellow solids: MS (ESI) m/z 489 [M+H]$^+$, 487 [M−H]$^−$, $^1$H-NMR (CDCl$_3$) δ 7.77 (2H, d, J=8.0 Hz), 7.45–7.16 (11H, m), 6.54 (1H, br.s), 3.36 (2H, br.s), 2.73 (2H, br.s), 2.31 (3H, s), 2.28 (3H, s), 2.20 (3H, s).

Example 15

N-{[(2-{4-[4-(4-Fluorophenyl)-3,5-dimethyl-1H-pyrazol-1-yl]phenyl}ethyl)amino]carbonyl}-4-methylbenzenesulfonamide Mono-p-toluenesulfonate Salt Step 1. 2-{4-[4-(4-Fluorophenyl)-3,5-dimethyl-1H-pyrazol-1-yl]phenyl}ethanol The title compound was prepared according to the procedure described in step 1 of Example 12 from 2-[4-(4-iodo- 3,5-dimethyl-1H-pyrazol-1-yl)phenyl]ethanol (step 2 of Example 11) and 4-fluorobenzeneboronic acid: MS (ESI) m/z 306 [M+H]+, $^1$H-NMR (CDCl$_3$) δ 7.44–7.02 (8H, m), 3.89 (2H, t, J=6.6 Hz), 2.93 (2H, t, J=6.6 Hz), 2.30(3H, s), 2.27 (3H, s).

Step 2. 1-[4-(2-Chloroethyl)phenyl]-4-(4-fluorophenyl)-3,5-dimethyl-1H-pyrazole

The title compound was prepared according to the procedure described in step 1 of Example 14 from 2-{4-[4-(4-fluorophenyl)-3,5-dimethyl-1H-pyrazol-1-yl]phenyl}ethanol (step1): MS (ESI) m/z 329 [M+H]+, $^1$H-NMR (CDCl$_3$) δ 7.44 (2H, d, J=6.4 Hz), 7.34–7.10 (6H, m), 3.74 (2H, t, J=7.3 Hz), 3.12 (2H, t, J=7.3 Hz), 2.30 (3H, s), 2.27 (3H, s).

Step 3. 1-[4-(2-Azidoethyl)phenyl]-4-(4-fluorophenyl)-3,5-dimethyl-1H-pyrazole

The title compound was prepared according to the procedure described in step 2 of Example 14 from 1-[4-(2-chloroethyl)phenyl]-4-(4-fluorophenyl)-3,5-dimethyl-1H-pyrazole (step 2): MS (ESI) m/z 336 [M+H]+, $^1$H-NMR (CDCl$_3$) δ 7.44 (2H, d, J=8.4 Hz), 7.34–7.25 (4H, m), 7.16–7.10 (2H, m), 3.55 (2H, t, J=7.2 Hz), 2.95 (2H, t, J=7.2 Hz), 2.30 (3H, s), 2.27 (3H, s).

Step 4. 2-{4-[4-(4-Fluorophenyl)-3,5-dimethyl-1H-pyrazol-1-yl]phenyl}ethylamine

The title compound was prepared according to the procedure described in step 3 of Example 14 from 1-[4-(2-azidoethyl)phenyl]-4-(4-fluorophenyl)-3,5-dimethyl-1H-pyrazole (step 3): MS (ESI) m/z 310 [M+H]+, $^1$H-NMR (CDCl$_3$) δ 7.41–7.08 (8H, m), 2.99 (2H, t, J=6.6 Hz), 2.79 (2H, t, J=6.6 Hz), 2.28 (3H, s), 2.25 (3H, s).

Step 5. N-{[(2-{4-[4-(4-Fluorophenyl)-3,5-dimethyl-1H-pyrazol-1-yl]phenyl}ethyl)amino]carbonyl}-4-methylbenzenesulfonamide The title compound was prepared according to the procedure described in step 4 of Example 14 from 2-{4-[4-(4-fluorophenyl)-3,5-dimethyl-1H-pyrazol-1-yl]phenyl}ethylamine (step 4): MS (ESI) m/z 507 [M+H]+, 505 [M−H]−, $^1$H-NMR (CDCl$_3$) δ 7.75 (2H, d, J=8.4 Hz), 7.43–7.31 (6H, m), 7.29–7.26 (4H, m), 6.49 (1H, br.s), 3.26–3.24 (2H, m), 2.72 (2H, t, J=7.2 Hz), 2.37 (3H, s), 2.37 (3H, s), 2.25 (3H, s), 2.22 (3H, s).

Step 6. N-{[(2-{4-[4-(4-Fluorophenyl)-3,5-dimethyl-1H-pyrazol-1-yl]phenyl}ethyl)amino]carbonyl}-4-methylbenzenesulfonamide mono-p-toluenesulfonate salt A mixture of N-{[(2-{4-[4-(4-fluorophenyl)-3,5-dimethyl-1H-pyrazol-1-yl]phenyl}ethyl)amino]carbonyl}-4-methylbenzenesulfonamide (step 5, 146 mg, 0.289 mmol), p-toluenesulfonic acid (55 mg, 0.289 mmol) in acetone (10 ml) and methanol (10 mL) was stirred at room temperature for 1 h. The reaction mixture was evaporated to afford 195 mg of the title compound as white solids: MS (ESI) m/z 507 [M+H]+, 505 [M−H]−.

Example 16

N-{[(2-{4-[3,5-Dimethyl-4-(4-methylphenyl)-1H-pyrazol-1-yl]phenyl}ethyl)amino]carbonyl}-4-methylbenzenesulfonamide Mono-p-toluenesulfonyl Salt Step 1. 1-[4-(2-Chloroethyl)phenyl]-3,5-dimethyl-4-(4-methylphenyl)-1H-pyrazole The title compound was prepared according to the procedure described in step 1 of Example 14 from 2-{4-[3,5-dimethyl-4-(4-methylphenyl)-1H-pyrazol-1-yl]phenyl}ethanol (step 1 of Example 12): MS (ESI) m/z 325 [M+H]+, $^1$H-NMR (CDCl$_3$) δ 7.45–7.22 (8H, m), 3.74 (2H, t, J=7.3 Hz), 3.12 (2H, t, J=7.3 Hz), 2.40 (3H, s), 2.32 (3H, s), 2.29 (3H, s).

Step 2. 1-[4-(2-Azidoethyl)phenyl]-3,5-dimethyl-4-(4-methylphenyl)-1H-pyrazole

The title compound was prepared according to the procedure described in step 2 of Example 14 from 1-[4-(2-chloroethyl)phenyl]-3,5-dimethyl-4-(4-methylphenyl)-1H-pyrazole (step 1): MS (ESI) m/z 332 [M+H]+.

Step 3. 2-{4-[3,5-Dimethyl-4-(4-methylphenyl)-1H-pyrazol-1-yl]phenyl}ethanamine

The title compound was prepared according to the procedure described in step 3 of Example 14 from 1-[4-(2-azidoethyl)phenyl]-3,5-dimethyl-4-(4-methylphenyl)-1H-pyrazole (step 2): MS (ESI) m/z 306 [M+H]+, $^1$H-NMR (CDCl$_3$) δ 7.42 (2H, d, J=8.6 Hz), 7.31–7.20 (6H, m), 3.00 (2H, t, J=6.8 Hz), 2.81 (2H, t, J=6, 8 Hz), 2.40 (3H, s), 2.32 (3H, s), 2.29 (3H, s).

Step 4. N-{[(2-{4-[3,5-Dimethyl-4-(4-methylphenyl)-1H-pyrazol-1-yl]phenyl}ethyl)amino]carbonyl}-4-methylbenzenesulfonamide The title compound was prepared according to the procedure described in step 4 of Example 14 from 2-{4-[3,5-dimethyl-4-(4-methylphenyl)-1H-pyrazol-1-yl]phenyl}ethanamine (step 3): MS (ESI) m/z 503 [M+H]+, 501 [M−H]−, $^1$H-NMR (CDCl$_3$) δ 7.75 (2H, d, J=8.3 Hz), 7.43–7.38 (4H, m), 7.28–7.25 (6H, m), 6.49 (1H, br.s), 3.28–3.24 (2H, m), 2.71 (2H, t, J=7.0 Hz), 2.37 (3H, s), 2.25 (3H, s), 2.25 (3H, s), 2.21 (3H, s).

Step 5. N-{[(2-{4-[3,5-Dimethyl-4-(4-methylphenyl)-1H-pyrazol-1-yl]phenyl}ethyl)amino]carbonyl}-4-methylbenzenesulfonamide mono-p-toluenesulfonate salt The title compound was prepared according to the procedure described in step 6 of Example 15 from N-{[(2-{4-[3,5-dimethyl-4-(4-methylphenyl)-1H-pyrazol-1-yl]phenyl}ethyl)amino]carbonyl}-4-methylbenzenesulfonamide (step 4): MS (ESI) m/z 503 [M+H]+, 501 [M−H]−.

Example 17

N-{[(2-{4-[4-(4-Chlorophenyl)-3,5-dimethyl-1H-pyrazol-1-yl]phenyl}ethyl)amino]carbonyl}-4-methylbenzenesulfonamide Mono-sodium Salt Step 1. 1-[4-(2-Chloroethyl)phenyl]-4-(4-chlorophenyl)-3,5-dimethyl-1H-pyrazole The title compound was prepared according to the procedure described in step 1 of Example 14 from 2-{4-[4-(4-chlorophenyl)-3,5-dimethyl-1H-pyrazol-1-yl]phenyl}ethanol (step 1 of Example 13): MS (ESI) m/z 344 [M+H]+, $^1$H-NMR (CDCl$_3$) δ 7.53–7.16 (8H, m), 3.75 (2H, t, J=7.3 Hz), 3.13 (2H, t, J=7.3 Hz), 2.31 (3H, s), 2.28 (3H, s).

Step 2. 1-[4-(2-Azidoethyl)phenyl]-4-(4-chlorophenyl)-3,5-dimethyl-1H-pyrazole

The title compound was prepared according to the procedure described in step 2 of Example 14 from 1-[4-(2-chloroethyl)phenyl]-4-(4-chlorophenyl)-3,5-dimethyl-1H-pyrazole (step 1): MS (ESI) m/z 352 [M+H]+, $^1$H-NMR (CDCl$_3$) δ 7.45–7.32 (8H, m), 3.55 (2H, t, J=7.1 Hz), 2.95 (2H, t, J=7.1 Hz), 2.31 (3H, s), 2.28 (3H, s).

Step 3. 2-{4-[4-(4-Chlorophenyl)-3,5-dimethyl-1H-pyrazol-1-yl]phenyl}ethylamine

The title compound was prepared according to the procedure described in step 3 of Example 14 from 1-[4-(2-azidoethyl)phenyl]-4-(4-chlorophenyl)-3,5-dimethyl-1H-pyrazole (step 2): MS (ESI) m/z 326 [M+H]+, $^1$H-NMR (CDCl$_3$) δ 7.42–7.24 (8H, m), 3.04–2.98 (2H, m), 2.82 (2H, t, J=6.7 Hz), 2.31 (3H, s), 2.27 (3H, s).

Step 4. N-{[(2-{4-[4-(4-Chlorophenyl)-3,5-dimethyl-1H-pyrazol-1-yl]phenyl}ethyl)amino]carbonyl}-4-methylbenzenesulfonamide The title compound was prepared according to the procedure described in step 4 of Example 14 from 2-{4-[4-(4-chlorophenyl)-3,5-dimethyl-1H-pyrazol-1-yl]phenyl}ethylamine (step 3): $^1$H-NMR (CDCl$_3$) δ 7.69 (2H, d, J=8.4 Hz), 7.43–7.23 (10H, m), 6.50 (1H, br.s), 3.54–3.48 (2H, m), 2.87 (2H, t, J=6.9 Hz), 2.42 (3H, s), 2.31 (3H, s), 2.26 (3H, s).

Step 5. N-{[(2-{4-[4-(4-Chlorophenyl)-3,5-dimethyl-1H-pyrazol-1-yl]phenyl}ethyl)amino]carbonyl}-4-methylbenzenesulfonamide mono-sodium salt The title compound was prepared according to the procedure described in step 4 of Example 8 from N-{[(2-{4-[4-(4-chlorophenyl)-3,5-dimethyl-1H-pyrazol-1-yl]phenyl}ethyl)amino]carbonyl}-4-methylbenzenesulfonamide (step 4): MS (ESI) m/z 523 [M+H]$^+$, 521 [M−H]$^−$.

Example 18

N-{[(2-{4-[4-(4-Ethoxyphenyl)-3,5-dimethyl-1H-pyrazol-1-yl]phenyl}ethyl)amino]carbonyl}-4-methylbenzenesulfonamide Mono-sodium Salt Step 1. 2-{4-[4-(4-Ethoxyphenyl)-3,5-dimethyl-1H-pyrazol-1-yl]phenyl}ethanol The title compound was prepared according to the procedure described in step 1 of Example 12 from 2-[4-(4-iodo-3,5-dimethyl-1H-pyrazol-1-yl)phenyl]ethanol (step 2 of Example 11) and 4-ethoxybenzene boronic acid: MS (ESI) m/z 337 [M+H]$^+$, 1H-NMR (CDCl$_3$) δ 7.43 (2H, d, J=8.6 Hz), 7.33 (2H, d, J=8.6 Hz), 7.24 (2H, d, J=8.7 Hz), 6.98 (2H, d, J=8.7 Hz), 4.08 (2H, q, J=6.9 Hz), 3.91–3.89 (2H, m), 2.93 (2H, t, J=6.6 Hz), 2.31 (3H, s), 2.28 (3H, s), 1.45 (3H, t, J=6.9 Hz).

Step 2. 1-[4-(2-Chloroethyl)phenyl]-4-(4-ethoxyphenyl)-3,5-dimethyl-1H-pyrazole

The title compound was prepared according to the procedure described in step 1 of Example 14 from 2-{4-[4-(4-ethoxyphenyl)-3,5-dimethyl-1H-pyrazol-1-yl]phenyl}ethanol (step 1): MS (ESI) m/z 355 [M+H]$^+$, $^1$H-NMR (CDCl$_3$) δ 7.44 (2H, d, J=8.3 Hz), 7.34–7.21 (4H, m), 6.97 (2H, d, J=8.5 Hz), 4.08 (2H, q, J=7.9 Hz), 3.74 (2H, t, J=7.3 Hz), 3.12 (2H, t, J=7.3 Hz), 2.31 (3H, s), 2.28 (3H, s), 1.45 (3H, t, J=7.9 Hz).

Step 3. 1-[4-(2-Azidoethyl)phenyl]-4-(4-ethoxyphenyl)-3,5-dimethyl-1H-pyrazole

The title compound was prepared according to the procedure described in step 2 of Example 14 from 1-[4-(2-chloroethyl)phenyl]-4-(4-ethoxyphenyl)-3,5-dimethyl-1H-pyrazole (step 2): MS (ESI) m/z 362 [M+H]$^+$, $^1$H-NMR (CDCl$_3$) δ 7.44 (2H, d, J=8.4 Hz), 7.32 (2H, d, J=8.4 Hz), 7.24–7.21 (2H, m), 6.97 (2H, d, J=6.6 Hz), 4.08 (2H, q, J=7.0 Hz), 3.54 (2H, t, J=7.1 Hz), 2.95 (2H, t, J=7.1 Hz), 2.31 (3H, s), 2.28 (3H, s), 1.45 (3H, t, J=7.0 Hz).

Step 4. 2-{4-[4-(4-Ethoxyphenyl)-3,5-dimethyl-1H-pyrazol-1-yl]phenyl}ethylamine

The title compound was prepared according to the procedure described in step 3 of Example 14 from 1-[4-(2-azidoethyl)phenyl]-4-(4-ethoxyphenyl)-3,5-dimethyl-1H-pyrazole (step 3): MS (ESI) m/z 336 [M+H]$^+$, $^1$H-NMR (CDCl$_3$) δ 7.41 (2H, d, J=8.4 Hz), 7.31–7.22 (4H, m), 6.97 (2H, t, J=8.8 Hz), 4.08 (2H, q, J=7.0 Hz), 3.01 (2H, t, J=7.0 Hz), 2.81 (2H, t, J=7.0 Hz), 2.31 (3H, s), 2.28 (3H, s), 1.45 (3H, s).

Step 5. N-{[(2-{4-[4-(4-Ethoxyphenyl)-3,5-dimethyl-1H-pyrazol-1-yl]phenyl}ethyl)amino]carbonyl}-4-methylbenzenesulfonamide The title compound was prepared according to the procedure described in step 4 of Example 14 from 2-{4-[4-(4-ethoxyphenyl)-3,5-dimethyl-1H-pyrazol-1-yl]phenyl}ethylamine (step 4): MS (ESI) m/z 533 [M+H]$^+$, 531 [M−H]$^−$, $^1$H-NMR (CDCl$_3$) δ 7.66 (2H, d, J=8.2 Hz), 7.41 (2H, d, J=8.2 Hz), 7.33–7.21 (6H, m), 6.97 (2H, d, J=8.4 Hz), 6.54 (1H, br.s), 4.08 (2H, q, J=7.1 Hz), 3.51 (2H, t, J=6.6 Hz), 2.87 (2H, t, J=6.6 Hz), 2.42 (3H, s), 2.32 (3H, s), 2.27 (3H, s), 1.45 (3H, t, J=7.1 Hz).

Step 6. N-{[(2-{4-[4-(4-Ethoxyphenyl)-3,5-dimethyl-1H-pyrazol-1-yl]phenyl}ethyl)amino]carbonyl}-4-methylbenzenesulfonamide mono-sodium salt The title compound was prepared according to the procedure described in step 4 of Example 8 from N-{[(2-{4-[4-(4-ethoxyphenyl)-3,5-dimethyl-1H-pyrazol-1-yl]phenyl}ethyl)amino]carbonyl}-4-methylbenzenesulfonamide (step 5): MS (ESI) m/z 533 [M+H]$^+$, 531 [M−H]$^−$.

Example 19

N-{[(2-{4-[4-(3,4-Dimethylphenyl)-3,5-dimethyl-1H-pyrazol-1-yl]phenyl}ethyl)amino]carbonyl}-4-methylbenzenesulfonamide Mono-sodium Salt Step 1. 1-[4-(2-Chloroethyl)phenyl]-3,5-dimethyl-1H-pyrazole The title compound was prepared according to the procedure described in step 1 of Example 14 from 2-[4-(3,5-dimethyl-1H-pyrazol-1-yl)phenyl]ethanol (step 1 of Example 11): MS (ESI) m/z 234 [M+H]$^+$.

Step 2. 1-[4-(2-Azidoethyl)phenyl]-3,5-dimethyl-1H-pyrazole

The title compound was prepared according to the procedure described in step 2 of Example 14 from 1-[4-(2-chloroethyl)phenyl]-3,5-dimethyl-1H-pyrazole (step 1): MS (EI) m/z 241 [M]$^+$.

Step 3. 2-[4-(3,5-Dimethyl-1H-pyrazol-1-yl)phenyl]ethanamine

The title compound was prepared according to the procedure described in step 3 of Example 14 from 1-[4-(2-azidoethyl)phenyl]-3,5-dimethyl-1H-pyrazole (step 2): H-NMR (CDCl$_3$) δ 7.37–7.27 (4H, m), 5.98 (1H, s), 2.99 (2H, t, J=6, 8 Hz), 2.79 (2H, t, J=6.8 Hz), 2.29 (3H, s).

Step 4. 2-[4-(4-Iodo-3,5-dimethyl-1H-pyrazol-1-yl)phenyl]ethanamine

The title compound was prepared according to the procedure described in step 2 of Example 11 from 2-[4-(3,5-dimethyl-1H-pyrazol-1-yl)phenyl]ethanamine (step 3): MS (ESI) m/z 341 [M+H]$^+$, $^1$H-NMR (CDCl$_3$) δ: 7.43–7.28 (4H, m), 3.06 (2H, br.s), 2.91 (2H, br.s), 2.30 (3H, s), 2.18 (3H, s).

Step 5. 2-{4-[4-(3,4-Dimethylphenyl)-3,5-dimethyl-1H-pyrazol-1-yl]phenyl}ethylamine The title compound was prepared according to the procedure described in step 1 of Example 12 from 2-[4-(4-iodo-3,5-dimethyl-1H-pyrazol-1-yl)phenyl]ethanamine (step 4) and 3,4-dimethylbenzeneboronic acid: MS (ESI) m/z 320 [M+H]$^+$.

Step 6. N-{[(2-{4-[4-(3,4-Dimethylphenyl)-3,5-dimethyl-1H-pyrazol-1-yl]phenyl}ethyl)amino]carbonyl}-4-methylbenzenesulfonamide The title compound was prepared according to the procedure described in step 4 of Example 14 from 2-{4-[4-(3,4-dimethylphenyl)-3,5-dimethyl-1H-pyrazol-1-yl]phenyl}ethylamine (step 5): MS (ESI) m/z 517 [M+H]$^+$, 515 [M−H]$^−$, $^1$H-NMR (CDCl$_3$) δ 7.73 (2H, d, J=8.3 Hz), 7.35–7.19 (7H, m), 7.09–7.03 (2H, m), 6.44 (1H, br.s), 3.50–3.44 (2., m), 2.86 (2H, t, J=6.8 Hz), 2.40 (3H, s), 2.31 (6H, s), 2.25 (3H, s).

Step 7. N-{[(2-{4-[4-(4-Ethoxyphenyl)-3,5-dimethyl-1H-pyrazol-1-yl]phenyl}ethyl)amino]carbonyl}-4-methylbenzenesulfonamide mono-sodium salt The title compound was prepared according to the procedure described in step 4 of Example 8 from N-{[(2-{4-[4-(3,4-dimethylphenyl)-3,5-dimethyl-1H-pyrazol-1-yl]phenyl}ethyl)amino]carbonyl}-4-methylbenzenesulfonamide (step 6): MS (ESI) m/z 517 [M+H]$^+$, 515 [M−H]$^−$.

Example 20

N-{[(2-{4-[4-(3,5-Difluorophenyl)-3,5-dimethyl-1H-pyrazol-1-yl]phenyl}ethyl)amino]carbonyl}-4-methylbenzenesulfonamide Sodium Salt Step 1. 2-{4-[4-(3,5-Difluorophenyl)-3,5-dimethyl-1H-pyrazol-1-yl]phenyl}ethanol The title compound was prepared according to the procedure described in step 1 of Example 12 from 2-[4-(4-iodo-3,5-dimethyl-1H-pyrazol-1-yl)phenyl]ethanol (step 2 of Example 11) and 3,5-difluorobenzeneboronic acid: MS (ESI) m/z 329 [M+H]$^+$, $^1$H-NMR (CDCl$_3$) δ 7.70–7.63 (1H, m), 7.55–7.33 (4H, m), 6.87–6.73 (2H, m), 3.89 (2H, t, J=6.2 Hz), 2.93 (2H, t, J=6.6 Hz), 2.33 (3H, s), 2.30 (3H, s).

Step 2. 1-[4-(2-Chloroethyl)phenyl]-4-(3,5-difluorophenyl)-3,5-dimethyl-1H-pyrazole The title compound was prepared according to the procedure described in step 1 of Example 14 from 2-{4-[4-(3,5-difluorophenyl)-3,5-dimethyl-1H-pyrazol-1-yl]phenyl}ethanol (step 1): MS (ESI) m/z 347 [M+H]$^+$, $^1$H-NMR (CDCl$_3$) δ 7.44–7.16 (4H, m), 6.85–6.73 (3H, m), 3.75 (2H, t, J=7.4 Hz), 3.13 (2H, t, J=7.4 Hz), 2.33 (3H, s), 2.31 (3H, s).

Step 3. 1-[4-(2-Azidoethyl)phenyl]-4-(3,5-difluorophenyl)-3,5-dimethyl-1H-pyrazole The title compound was prepared according to the procedure described in step 2 of Example 14 from 1-[4-(2-chloroethyl)phenyl]-4-(3,5-difluorophenyl)-3,5-dimethyl-1H-pyrazole (step 2): MS (ESI) m/z 354 [M+H]$^+$, $^1$H-NMR (CDCl$_3$) δ 7.44–7.26 (4H, m) 6.88–6.73 (3H, m), 3.55 (2H, t. J=6.1 Hz), 2.96 (2H, t, J=6.1 Hz), 2.33 (3H, s), 2.30 (3H, s).

Step 4. 2-{4-[4-(3,5-Difluorophenyl)-3,5-dimethyl-1H-pyrazol-1-yl]phenyl}ethylamine The title compound was prepared according to the procedure described in step 3 of Example 14 from 1-[4-(2-azidoethyl)phenyl]-4-(3,5-difluorophenyl)-3,5-dimethyl-1H-pyrazole (step 3): MS (ESI) m/z 328 [M+H]$^+$, $^1$H-NMR (CDCl$_3$) δ 7.41–7.30 (4H, m), 6.85–6.76 (3H, m), 3.01 (2H, t, J=6.6 Hz), 2.81 (2H, t, J=6.6 Hz), 2.33 (3H, s), 2.30 (3H, s).

Step 5. N-{[(2-[4-[4-(3,5-Difluorophenyl)-3,5-dimethyl-1H-pyrazol-1-yl]phenyl}ethyl)amino]carbonyl}-4-methylbenzenesulfonamide The title compound was prepared according to the procedure described in step 4 of Example 14 from 2-{4-[4-(3,5-difluorophenyl)-3,5-dimethyl-1H-pyrazol-1-yl]phenyl}ethylamine (step 4): MS (ESI) m/z 525 [M+H]$^+$, 523 [M−H]$^−$, $^1$H-NMR (CDCl$_3$) δ 7.67 (2H, d, J=8.4 Hz), 7.40–7.27 (7H, m), 6.86–6.77 (2H, m), 6.54 (1H, br.s), 3.54–3.49 (2H, m), 2.88 (2H, t, J=5.6 Hz), 2.43 (3H, s), 2.34 (3H, s), 2.29 (3H, s).

Step 6. N-{[(2-{4-[4-(3,5-Difluorophenyl)-3,5-dimethyl-1H-pyrazol-1-yl]phenyl}ethyl)amino]carbonyl}-4-methylbenzenesulfonamide mono-sodium salt The title compound was prepared according to the procedure described in step 4 of Example 8 from N-{[(2-{4-[4-(3,5-difluorophenyl)-3,5-dimethyl-1H-pyrazol-1-yl]phenyl}ethyl)amino]carbonyl}-4-methylbenzenesulfonamide (step 5). MS (ESI) m/z 525 [M+H]$^+$, 523 [M−H]$^−$.

Example 21

2-Chloro-N-[({2-[4-(3,5-dimethyl-4-phenyl-1H-pyrazol-1-yl)phenyl]ethyl}amino)carbonyl]benzenesulfonamide Mono-p-toluenesulfonate Salt Step 1. 2-Chloro-N-[({2-[4-(3,5-dimethyl-4-phenyl-1H-pyrazol-1-yl)phenyl]ethyl}amino)carbonyl]benzenesulfonamide The title compound was prepared according to the procedure described in step 4 of Example 14 from 2-[4-(3,5-dimethyl-4-phenyl-1H-pyrazol-1-yl)phenyl]ethylamine (step 3 of Example 14) and 2-chlorobenzene isocyanate: $^1$H-NMR (CDCl$_3$) δ 8.11 (1H, d, J=7.3 Hz), 7.47–7.20 (12H, m), 6.38 (1H, br.s), 3.44–3.38 (2H, m), 2.78 (2H, t, J=6.6 Hz), 2.30 (3H, s), 2.21 (3H, s).

Step 2. 2-Chloro-N-[({2-[4-(3,5-dimethyl-4-phenyl-1H-pyrazol-1-yl)phenyl]ethyl}amino)carbonyl]benzenesulfonamide mono-p-toluenesulfonate salt The title compound was prepared according to the procedure described in step 6 of Example 15 from 2-chloro-N-[({2-[4-(3,5-dimethyl-4-phenyl-1H-pyrazol-1-yl)phenyl]ethyl}amino)carbonyl]benzenesulfonamide (step 1): MS (ESI) m/z 509 [M+H]$^+$, 507 [M−H]$^−$.

Example 22

N-[({2-[4-(3,5-Dimethyl-4-phenyl-1H-pyrazol-1-yl)phenyl]ethyl}amino)carbonyl]benzenesulfonamide Mono-p-toluenesulfonate Salt Step 1. Phenyl 2-[4-(3,5-dimethyl-4-phenyl-1H-pyrazol-1-yl)phenyl]ethylcarbamate To a stirred solution of 2-[4-(3,5-dimethyl-4-phenyl-1H-pyrazol-1-yl)phenyl]ethylamine (step 3 of Example 14, 1.36 g, 4.66 mmol), dichloromethane (30 m]L) and triethylamine (0.78 mL, 5.60 mmol) was added phenyl chlorocarbonate (0.64 mL, 5.13 mmol) slowly at room temperature. After 1 h, the mixture was poured into water and extracted with dichloromethane. The organic fraction was dried over MgSO$_4$ and concentrated under reduced pressure. The residue was purified by silica-gel column chromatography eluting with hexane/ethyl acetate (2:1) to afford 1.57 g (82%) of the title compound as white solids: MS (ESI) m/z 412 [M+H]$^+$, $^1$H-NMR (CDCl$_3$) δ 7.48–7.10 (14H, m), 5.06 (1H, br.s), 3.60–3.53 (2H, m), 2.96 (2H, t, J=6.8 Hz), 2.34 (3H, s), 2.31 (3H, s).

Step 2. N-[({2-[4-(3,5-Dimethyl-4-phenyl-1H-pyrazol-1-yl)phenyl]ethyl}amino)carbonyl]benzenesulfonamide To a stirred solution of benzenesulfonamide (40 mg, 0.26 mmol), sodium hydride (11 mg, 0.49 mmol) and N,N-dimethylformamide (2 mL) was added dropwise a solution of phenyl 2-[4-(3,5-dimethyl-4-phenyl-1H-pyrazol-1-yl)phenyl]ethylcarbamate (step 1, 100 mg, 0.24 mmol) in N,N-dimethylformamide (2 mL) at room temperature. After 2 h, the mixture was poured into ice-water and extracted with dichloromethane. The organic layer was dried over MgSO$_4$ and evaporated in vacuo. The residue was purified by TLC with dichloromethane/methanol (10:1) to give 84 mg (73%) of the title compound as white solids: $^1$H-NMR (CDCl$_3$) δ 7.89 (2H, d, J=8.2 Hz), 7.64–7.21 (12H, m), 6.33 (1H, br.s), 3.51–3.44 (2H, m), 2.84 (2H, t, J=6.8 Hz), 2.33 (3H, s), 2.24 (3H, s).

Step 3. N-[({2-[4-(3,5-Dimethyl-4-phenyl-1H-pyrazol-1-yl)phenyl]ethyl}amino)carbonyl]benzenesulfonamide mono-p-toluenesulfonate salt The title compound was prepared according to the procedure described in step 6 of Example 15 from N-[({2-[4-(3,5-dimethyl-4-phenyl-1H-pyrazol-1-yl)phenyl]ethyl}amino)carbonyl]benzenesulfonamide (step 2): MS (ESI) m/z 475 [M+H]$^+$, 473 [M−H]$^-$.

Example 23

N-[({2-[4-(3,5-Dimethyl-4-phenyl-1H-pyrazol-1-yl)phenyl]ethyl}amino)carbonyl]-4-ethylbenzenesulfonamide Mono-p-toluenesulfonate Salt Step 1. N-[({2-[4-(3,5-Dimethyl-4-phenyl-1H-pyrazol-1-yl)phenyl]ethyl}amino)carbonyl]-4-ethylbenzenesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 4-ethylbenzenesulfonamide: $^1$H-NMR (CDCl$_3$) δ 7.77 (2H, d, J=8.4 Hz), 7.47–7.23 (11H, m), 6.39 (1H, br.s), 3.52–3.45 (2H, m), 2.86 (2H, t, J=6.7 Hz), 2.71 (2H, q, J=7.7 Hz), 2.33 (3H, s), 2.25 (3H, s), 1.25 (3H, t, J=7.7 Hz).

Step 2. N-[({2-[4-(3,5-Dimethyl-4-phenyl-1H-pyrazol-1-yl)phenyl]ethyl}amino) carbonyl]-4-ethylbenzenesulfonamide mono-p-toluenesulfonate salt The title compound was prepared according to the procedure described in step 6 of Example 15 from N-[({2-[4-(3,5-dimethyl-4-phenyl-1H-pyrazol-1-yl)phenyl]ethyl}amino)carbonyl]-4-ethylbenzenesulfonamide (step 1): MS (ESI) m/z 503 [M+H]$^+$, 501 [M−H]$^-$.

Example 24

N-[({2-[4-(3,5-Dimethyl-4-phenyl-1H-pyrazol-1-yl)phenyl]ethyl}amino)carbonyl]-4-(1-methylethyl) Benzenesulfonamide Mono-p-toluenesulfonate Salt Step 1. N-[({2-[4-(3,5-Dimethyl-4-phenyl-1H-pyrazol-1-yl)phenyl]ethyl}amino)carbonyl]-4-(1-methylethyl)benzenesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 4-(1-methylethyl)benzenesulfonamide: $^1$H-NMR (CDCl$_3$) δ 7.75 (2H, d, J=8.4 Hz), 7.47–7.24 (11H, m), 6.44 (1H, br.s), 3.54–3.47 (2H, m), 3.02–2.84 (3H, m), 2.33 (3H, s), 2.26 (3H, s), 1.25 (6H, d, J=6.9 Hz).

Step 2. N-[({2-[4-(3,5-Dimethyl-4-phenyl-1H-pyrazol-1-yl)phenyl]ethyl}amino)carbonyl]-4-(1-methylethyl)benzenesulfonamide Mono-p-toluenesulfonate Salt The title compound was prepared according to the procedure described in step 6 of Example 15 from N-[({2-[4-(3,5-dimethyl-4-phenyl-1H-pyrazol-1-yl)phenyl]ethyl}amino)carbonyl]-4-(1-methylethyl)benzenesulfonamide (step 1): MS (ESI) m/z 517 [M+H]$^+$, 515 [M−H]$^-$.

Example 25

N-[({2-[4-(3,5-Dimethyl-4-phenyl-1H-pyrazol-1-yl)phenyl]ethyl}amino)carbonyl]-4-(methyloxy) Benzenesulfonamide Mono-p-toluenesulfonate Salt Step 1. N-[({2-[4-(3,5-Dimethyl-4-phenyl-1H-pyrazol-1-yl)phenyl]ethyl}amino)carbonyl]-4-(methyloxy)benzenesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 4-(methyloxy)benzenesulfonamide: $^1$H-NMR (CDCl$_3$) δ 7.77–7.73 (2H, m), 7.47–7.25 (9H, m), 6.96 (2H, d, J=9.1 Hz), 6.41 (1H, br.s), 3.85 (3H, s), 3.54–3.47 (2H, m), 2.87 (2H, t, J=6.7 Hz), 2.33 (3H, s), 2.27 (3H, s).

Step 2. N-[({2-[4-(3,5-Dimethyl-4-phenyl-1H-pyrazol-1-yl)phenyl]ethyl}amino)carbonyl]-4-(methyloxy)benzenesulfonamide Mono-p-toluenesulfonate Salt The title compound was prepared according to the procedure described in step 6 of Example 15 from N-[({2-[4-(3,5-dimethyl-4-phenyl-1H-pyrazol-1-yl)phenyl]ethyl}amino)carbonyl]-4-(methyloxy)benzenesulfonamide (step 1): MS (ESI) m/z 505 [M+H]$^+$, 503 [M−H]$^-$.

Example 26

4-Tert-butyl-N-[({2-[4-(3,5-dimethyl-4-phenyl-1H-pyrazol-1-yl)phenyl]ethyl}amino)carbonyl]benzenesulfonamide Mono-p-toluenesulfonate Salt Step 1. 4-tert-Butyl-N-[({2-[4-(3,5-dimethyl-4-phenyl-1H-pyrazol-1-yl)phenyl]ethyl}amino)carbonyl]benzenesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 4-tert-butylbenzenesulfonamide: $^1$H-NMR (CDCl$_3$) δ 7.76 (2H, d, J=8.7 Hz), 7.53–7.24 (11H, m), 6.43 (1H, br.s), 3.54–3.47 (2H, m), 2.87 (2H, t, J=6.6 Hz), 2.33 (3H, s), 2.26 (3H, s), 1.32 (9H, s).

Step 2. 4-tert-Butyl-N-[({2-[4-(3,5-dimethyl-4-phenyl-1H-pyrazol-1-yl)phenyl]ethyl}amino)carbonyl]benzenesulfonamide Mono-p-toluenesulfonate Salt The title compound was prepared according to the procedure described in step 6 of Example 15 from 4-tert-butyl-N-[({2-[4-(3,5-dimethyl-4-phenyl-1H-pyrazol-1-yl)phenyl]ethyl}amino)carbonyl]benzenesulfonamide (step 1): MS (ESI) m/z 531 [M+H]$^+$, 529 [M−H]$^-$.

Example 27

N-[({2-[4-(3,5-Dimethyl-4-phenyl-1H-pyrazol-1-yl)phenyl]ethyl}amino)carbonyl]-4-(trifluoromethyl) Benzenesulfonamide Mono-p-toluenesulfonate Salt Step 1. N-[({2-[4-(3,5-Dimethyl-4-phenyl-1H-pyrazol-1-yl)phenyl]ethyl}amino)carbonyl]-4-(trifluoromethyl)benzenesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 4-(trifluoromethyl)benzenesulfonamide: $^1$H-NMR (CDCl$_3$) δ 8.06 (2H, d, J=7.7 Hz), 7.80 (2H, d, J=8.2 Hz), 7.47–7.21 (9H, m), 6.10 (1H, br.s), 3.50–3.43 (2H, m), 2.86 (2H, t, J=6.3 Hz), 2.32 (3H, s), 2.23 (3H, s).

Step 2. N-[({2-[4-(3,5-Dimethyl-4-phenyl-1H-pyrazol-1-yl)phenyl]ethyl}amino)carbonyl]-4-(trifluoromethyl)benzenesulfonamide Mono-p-toluenesulfonate Salt The title compound was prepared according to the procedure described in step 6 of Example 15 from N-[({2-[4-(3,5-dimethyl-4-phenyl-1H-pyrazol-1-yl)phenyl]ethyl}amino)carbonyl]-4-(trifluoromethyl)benzenesulfonamide (step 1): MS (ESI) m/z 543 [M+H]$^+$, 541 [M−H]$^-$.

Example 28

N-[({2-[4-(3,5-Dimethyl-4-phenyl-1H-pyrazol-1-yl)phenyl]ethyl}amino)carbonyl]-4-[(trifluoromethyl)oxy]benzenesulfonamide Mono-p-toluenesulfonate Salt Step 1. N-[({2-[4-(3,5-Dimethyl-4-phenyl-1H-pyrazol-1-yl)phenyl]ethyl}amino)carbonyl]-4-[(trifluoromethyl)oxy]benzenesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 4-[(trifluoromethyl)oxy]benzenesulfonamide: $^1$H-NMR (CDCl$_3$) δ 7.98 (2H, d, J=9.1 Hz), 7.47–7.21 (11H, m), δ 12 (1H, br.s), 3.50–3.43 (2H, m), 2.85 (2H, t, J=6:5 Hz). 2.32 (3H, s), 2.23 (3H, s).

Step 2. N-[({2-[4-(3,5-Dimethyl-4-phenyl-1H-pyrazol-1-yl)phenyl]ethyl}amino)carbonyl]-4-[(trifluoromethyl)oxy]benzenesulfonamide mono-p-toluenesulfonate salt The title compound was prepared according to the procedure described in step 6 of Example 15 from N-[({2-[4-(3,5-dimethyl-4-phenyl-1H-pyrazol-1-yl)phenyl]ethyl}amino)carbonyl]-4-[(trifluoromethyl)oxy]benzenesulfonamide (step 1): MS (ESI) m/z 559 [M+H]$^+$, 557 [M−H]$^−$.

Example 29

N-[({2-[4-(3,5-Dimethyl-4-phenyl-1H-pyrazol-1-yl)phenyl]ethyl}amino)carbonyl]-5-methyl-2-pyridinesulfonamide Mono-p-toluenesulfonate Salt Step 1. N-[({2-[4-(3,5-Dimethyl-4-phenyl-1H-pyrazol-1-yl)phenyl]ethyl}amino)carbonyl]-5-methyl-2-pyridinesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 5-methyl-2-pyridinesulfonamide: $^1$H-NMR (CDCl$_3$) δ 8.47 (1H, s), 7.90 (1H, d, J=7.9 Hz), 7.73 (1H, d, J=7.9 Hz), 7.47–7.24 (9H, m), 6.68 (1H, br.s), 3.54–3.44 (2H, m), 2.88–2.83 (2H, m), 2.43 (3H, s), 2.33 (3H, s), 2.27 (3H, s).

Step 2. N-[({2-[4-(3,5-Dimethyl-4-phenyl-1H-pyrazol-1-yl)phenyl]ethyl}amino)carbonyl]-5-methyl-2-pyridinesulfonamide mono-p-toluenesulfonate salt The title compound was prepared according to the procedure described in step 6 of Example 15 from N-[({2-[4-(3,5-dimethyl-4-phenyl-1H-pyrazol-1-yl)phenyl]ethyl}amino)carbonyl]-5-methyl-2-pyridinesulfonamide (step 1): MS (ESI) m/z 490 [M+H]$^+$, 488 [M−H]$^−$.

Example 30

N-[({2-[4-(3,5-Dimethyl-4-phenyl-1H-pyrazol-1-yl)phenyl]ethyl}amino)carbonyl]-2-methylbenzenesulfonamide Mono-sodium Salt Step 1. N-[({2-[4-(3,5-Dimethyl-4-phenyl-1H-pyrazol-1-yl)phenyl]ethyl}amino)carbonyl]-2-methylbenzenesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 2-methylbenzenesulfonamide: $^1$H-NMR (CDCl$_3$) δ 7.93 (1H, d, J=8.3 Hz), 7.50–7.21 (12H, m), 6.29 (1H, br.s), 3.49–3.43 (2H, m), 2.81 (2H, t, J=6.5 Hz), 2.62 (3H, s), 2.33 (3H, s), 2.24 (3H, s).

Step 2. N-[({2-[4-(3,5-Dimethyl-4-phenyl-1H-pyrazol-1-yl)phenyl]ethyl}amino)carbonyl]-2-methylbenzenesulfonamide mono-sodium salt The title compound was prepared according to the procedure described in step 4 of Example 8 from N-[({2-[4-(3,5-dimethyl-4-phenyl-1H-pyrazol-1-yl)phenyl]ethyl}amino)carbonyl]-2-methylbenzenesulfonamide (step 1): MS (ESI) m/z 489 [M+H]$^+$, 487 [M−H]$^−$.

Example 31

N-[({2-[4-(3,5-Dimethyl-4-phenyl-1H-pyrazol-1-yl)phenyl]ethyl}amino)carbonyl]-4-chlorobenzenesulfonamide Mono-sodium Salt Step 1. N-[({2-[4-(3,5-Dimethyl-4-phenyl-1H-pyrazol-1-yl)phenyl]ethyl}amino)carbonyl]-4-chlorobenzenesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 4-chlorobenzenesulfonamide: $^1$H-NMR (CDCl$_3$) δ 7.84–7.79 (2H, m), 7.48–7.21 (11H, m), 6.24 (1H, br.s), 3.48–3.42 (2H, m), 2.83 (2H, t, J=7.1 Hz), 2.32 (3H, s), 2.24 (3H, s).

Step 2. N-[({2-[4-(3,5-Dimethyl-4-phenyl-1H-pyrazol-1-yl)phenyl]ethyl}amino)carbonyl]-4-chlorobenzenesulfonamide mono-sodium salt The title compound was prepared according to the procedure described in step 4 of Example 8 from N-[({2-[4-(3,5-dimethyl-4-phenyl-1H-pyrazol-1-yl)phenyl]ethyl}amino)carbonyl]-4-chlorobenzenesulfonamide (step 1): MS (ESI) m/z 509 [M+H]$^+$, 507 [M−H]$^−$.

Example 32

N-[({2-[4-(3,5-Dimethyl-4-phenyl-1H-pyrazol-1-yl)phenyl]ethyl}amino)carbonyl]-4-fluorobenzenesulfonamide Mono-sodium Salt Step 1. N-[({2-[4-(3,5-Dimethyl-4-phenyl-1H-pyrazol-1-yl)phenyl]ethyl}amino)carbonyl]-4-fluorobenzenesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 4-fluorobenzenesulfonamide: $^1$H-NMR (CDCl$_3$) δ 7.94–7.88 (2H, m), 7.47–7.15 (11H, m), 6.24 (1H, br.s), 3.48–3.42 (2H, m), 2.84 (2H, t, J=7.0 Hz), 2.32 (3H, s), 2.23 (3H, s).

Step 2. N-[({2-[4-(3,5-Dimethyl-4-phenyl-1H-pyrazol-1-yl)phenyl]ethyl}amino)carbonyl]-4-fluorobenzenesulfonamide mono-sodium salt The title compound was prepared according to the procedure described in step 4 of Example 8 from N-[({2-[4-(3,5-dimethyl-4-phenyl-1H-pyrazol-1-yl)phenyl]ethyl}amino)carbonyl]-4-fluorobenzenesulfonamide (step 1): MS (ESI) m/z 493 [M+H]$^+$, 491 [M−H]$^−$.

Example 33

N-[({2-[4-(3,5-Dimethyl-4-phenyl-1H-pyrazol-1-yl)phenyl]ethyl}amino)carbonyl]-3-chlorobenzenesulfonamide Mono-sodium Salt Step 1. N-[({2-[4-(3,5-Dimethyl-4-phenyl-1H-pyrazol-1-yl)phenyl]ethyl}amino)carbonyl]-3-chlorobenzenesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 3-chlorobenzenesulfonamide: $^1$H-NMR (CDCl$_3$) δ 7.91–7.90 (1H, m), 7.83–7.79 (1H, m), 7.53–7.20 (11H, m), 6.32 (1H, br.s), 3.47–3.40 (2H, m), 2.81 (2H, t, J=6.6 Hz), 2.30 (3H, s), 2.22 (3H, s).

Step 2. N-[({2-[4-(3,5-Dimethyl-4-phenyl-1H-pyrazol-1-yl)phenyl]ethyl}amino)carbonyl]-3-chlorobenzenesulfonamide mono-sodium salt The title compound was prepared according to the procedure described in step 4 of Example 8 from N-[({2-[4-(3,5-dimethyl-4-phenyl-1H-pyrazol-1-yl)phenyl]ethyl}amino)carbonyl]-3-chlorobenzenesulfonamide: MS (ESI) m/z 509 [M+H]$^+$, 507 [M−H]$^−$.

Example 34

N-[({2-[4-(3,5-Dimethyl-4-phenyl-1H-pyrazol-1-yl)phenyl]ethyl}amino)carbonyl]-3-methylbenzenesulfonamide Mono-sodium Salt Step 1. N-[({2-[4-(3,5-Dimethyl-4-phenyl-1H-pyrazol-1-yl)phenyl]ethyl}amino)carbonyl]-3-methylbenzenesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 3-methylbenzenesulfonamide: $^1$H-NMR (CDCl$_3$) δ 7.72–7.66 (2H, m), 7.46–7.22 (11H, m), 6.45 (1H, br.s), 3.48–3.45 (2H, m), 2.86–2.81 (2H, m), 2.39 (3H, s), 2.32 (3H, s), 2.25 (3H, s).

Step 2. N-[({2-[4-(3,5-Dimethyl-4-phenyl-1H-pyrazol-1-yl)phenyl]ethyl}amino)carbonyl]-3-methylbenzenesulfonamidemono-sodium salt The title compound was prepared according to the procedure described in step 4 of Example 8 from N-[({2-[4-(3,5-dimethyl-4-phenyl-1H-pyrazol-1-yl)phenyl]ethyl}amino)carbonyl]-3-methylbenzenesulfonamide (step 1): MS (ESI) m/z 489 [M+H]$^+$, 487 [M–H]$^-$.

Example 35

N-[({2-[4-(3,5-Dimethyl-4-phenyl-1H-pyrazol-1-yl)phenyl]ethyl}amino)carbonyl]-2-fluorobenzenesulfonamide Mono-sodium Salt Step 1. N-[({2-[4-(3,5-Dimethyl-4-phenyl-1H-pyrazol-1-yl)phenyl]ethyl}amino)carbonyl]-2-fluorobenzenesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 2-fluorobenzenesulfonamide: $^1$H-NMR (CDCl$_3$) δ 7.89 (1H, t, J=6.9 Hz), 7.45–7.06 (12H, m), 6.48 (1H, br.s), 3.46–3.36 (2H, m), 2.77–2.71 (2H, m), 2.28 (3H, s), 2.21 (3H, s).

Step 2. N-[({2-[4-(3,5-Dimethyl-4-phenyl-1H-pyrazol-1-yl)phenyl]ethyl}amino)carbonyl]-2-fluorobenzenesulfonamide mono-sodium salt The title compound was prepared according to the procedure described in step 4 of Example 8 from N-[({2-[4-(3,5-dimethyl-4-phenyl-1H-pyrazol-1-yl)phenyl]ethyl}amino)carbonyl]-2-fluorobenzenesulfonamide (step 1): MS (ESI) m/z 493 [M+H]$^+$, 491 [M–H]$^-$.

Example 36

N-[({2-[4-(3,5-Dimethyl-4-phenyl-1H-pyrazol-1-yl)phenyl]ethyl}amino)carbonyl]-3-fluorobenzenesulfonamide Mono-sodium Salt Step 1. N-[({2-[4-(3,5-Dimethyl-4-phenyl-1H-pyrazol-1-yl)phenyl]ethyl}amino)carbonyl]-3-fluorobenzenesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 3-fluorobenzenesulfonamide: $^1$H-NMR (CDCl$_3$) δ 7.70–7.59 (2H, m), 7.45–7.17 (11H, m), 6.41 (1H, br.s), 3.47–3.37 (2H, m), 2.77–2.73 (2H, m), 2.27 (3H, s), 2.21 (3H, s).

Step 2. N-[({2-[4-(3,5-Dimethyl-4-phenyl-1H-pyrazol-1-yl)phenyl]ethyl}amino)carbonyl]-3-fluorobenzenesulfonamide mono-sodium salt The title compound was prepared according to the procedure described in step 4 of Example 8 from N-[({2-[4-(3,5-dimethyl-4-phenyl-1H-pyrazol-1-yl)phenyl]ethyl}amino)carbonyl]-3-fluorobenzenesulfonamide (step 1): MS (ESI) m/z 493 [M+H]$^+$, 491 [M–H]$^-$.

Example 37

4-Cyano-N-[({2-[4-(3,5-dimethyl-4-phenyl-1H-pyrazol-1-yl)phenyl]ethyl}amino)carbonyl]benzenesulfonamide Mono-sodium Salt Step 1. 4-Cyano-N-[({2-[4-(3,5-dimethyl-4-phenyl-1H-pyrazol-1-yl)phenyl]ethyl}amino)carbonyl]benzenesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 4-cyanobenzenesulfonamide: $^1$H-NMR (CDCl$_3$) δ 7.99 (2H, d, J=8.4 Hz), 7.72 (2H, d, J=8.4 Hz), 7.45–7.15 (9H, m), 6.16 (1H, br.s), 3.36–3.34 (2H, m), 2.77–2.73 (2H, m), 2.29 (3H, s), 2.21 (3H, s).

Step 2. 4-Cyano-N-[({2-[4-(3,5-dimethyl-4-phenyl-1H-pyrazol-1-yl)phenyl]ethyl]amino)carbonyl]benzenesulfonamide mono-sodium salt The title compound was prepared according to the procedure described in step 4 of Example 8 from 4-cyano-N-[({2-[4-(3,5-dimethyl-4-phenyl-1H-pyrazol-1-yl)phenyl]ethyl}amino)carbonyl]benzenesulfonamide (step 1): MS (ESI) m/z 500 [M+H]$^+$, 498 [M–H]$^-$.

Example 38

N-[({2-[4-(3,5-Dimethyl-4-phenyl-1H-pyrazol-1-yl)phenyl]ethyl}amino)carbonyl]-2,4-dimethyl-1,3-thiazole-5-sulfonamide Mono-sodium Salt Step 1. N-[({2-[4-(3,5-Dimethyl-4-phenyl-1H-pyrazol-1-yl)phenyl]ethyl}amino)carbonyl]-2,4-dimethyl-1,3-thiazole-5-sulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 2,4-dimethyl-1,3-thiazole-5-sulfonamide: $^1$H-NMR [CDCl$_3$/CD$_3$OD(10:1)] δ 7.46–7.22 (9H, m), 6.20 (1H, br.s), 3.48–3.45 (2H, m), 2.88–2.82 (2H, m), 2.64 (3H, s), 2.59 (3H, s), 2.30 (3H, s), 2.20 (3H, s).

Step 2. N-[({2-[4-(3,5-Dimethyl-4-phenyl-1H-pyrazol-1-yl)phenyl]ethyl}amino)carbonyl-2,4-dimethyl-1,3-thiazole-5-sulfonamide mono-sodium salt The title compound was prepared according to the procedure described in step 4 of Example 8 from N-[({2-[4-(3,5-dimethyl-4-phenyl-1H-pyrazol-1-yl)phenyl]ethyl}amino)carbonyl]-2,4-dimethyl-1,3-thiazole-5-sulfonamide (step 1): MS (ESI) m/z 510 [M+H]$^+$, 508 [M–H]$^-$.

Example 39

N-[({2-[4-(3,5-Dimethyl-4-phenyl-1H-pyrazol-1-yl)phenyl]ethyl}amino)carbonyl]-3,4-dimethoxybenzenesulfonamide Mono-sodium Salt Step 1. N-[(2-[4-(3,5-Dimethyl-4-phenyl-1H-pyrazol-1-yl)phenyl]ethyl]amino)carbonyl]-3,4-dimethoxybenzenesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 3,4-dimethoxybenzenesulfonamide: $^1$H-NMR (CDCl$_3$) a 7.46–7.23 (11H, m), 6.92 (1H, d, J=8.4 Hz), 6.37 (1H, br.s), 3.92 (3H, s), 3.89 (3H, s), 3.49–3.45 (2H, m), 2.86 (2H, t, J=6.7 Hz), 2.32 (3H, s), 2.26 (3H, s).
Step 2. N-[({2-[4-(3,5-Dimethyl-4-phenyl-1H-pyrazol-1-yl)phenyl]ethyl}amino)carbonyl]-3,4-dimethoxybenzenesulfonamide mono-sodium salt The title compound was prepared according to the procedure described in step 4 of Example 8 from N-[({2-[4-(3,5-dimethyl-4-phenyl-1H-pyrazol-1-yl)phenyl]ethyl}amino)carbonyl]-3,4-dimethoxybenzenesulfonamide (step 1): MS (ESI) m/z 535 [M+H]$^+$, 533 [M–H]$^-$.

Example 40

N-[({2-[4-(3,5-Diethyl-4-phenyl-1H-pyrazol-1-yl)phenyl]ethyl}amino)carbonyl]-4-pyridinesulfonamide Mono-sodium Salt Step 1. N-[({2-[4-(3,5-Dimethyl-4-phenyl-1H-pyrazol-1-yl)phenyl]ethyl}amino)carbonyl]-4-pyridinesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 4-pyridinesulfonamide (*J. Chem. Soc.*, 1958, 3514: $^1$H-NMR (CDCl$_3$) δ 8.81 (2H, d, J=5.4 Hz), 7.77 (2H, d, J=5.9 Hz), 7.46–7.18 (9H, m), 6.11 (1H, br.s), 3.44–3.41 (2H, m), 2.84–2.79 (2H, m), 2.31 (3H, s), 2.21 (3H, s).

Step 2. N-[({2-[4-(3,5-Dimethyl-4-phenyl-1H-pyrazol-1-yl)phenyl]ethyl}amino) carbonyl]-4-pyridinesulfonamide Mono-sodium Salt The title compound was prepared according to the procedure described in step 4 of Example 8 from N-[({2-[4-(3,5-dimethyl-4-phenyl-1H-pyrazol-1-yl)phenyl]ethyl}amino)carbonyl]-4-pyridinesulfonamide (step 1): MS (ESI) m/z 476 [M+H]$^+$, 474 [M–H]$^-$.

Example 41

N-[({2-[4-(3,5-Dimethyl-4-phenyl-1H-pyrazol-1-yl)phenyl]ethyl}amino)carbonyl]-3-methoxybenzenesulfonamide Mono-sodium Salt Step 1. N-[({2-[4-(3,5-Dimethyl-4-phenyl-1H-pyrazol-1-yl)phenyl]ethyl}amino)carbonyl]-3-methoxybenzenesulfonamide The title compound was prepared according to the procedure described in step 2 of Example 22 from phenyl 2-[4-(3,5-dimethyl-4-phenyl-1H-pyrazol-1-yl)phenyl]ethylcarbamate (step 1 of Example 22) and 3-methoxybenzenesulfonamide: $^1$H-NMR (CDCl$_3$) δ 7.47–7.09 (13H, m), 6.36 (1H, br.s), 3.81 (3H, s), 3.49–3.43 (2H, m), 2.83 (2H, t, J=6.6 Hz), 2.32 (3H, s), 2.24 (3H, s).

Step 2. N-[({2-[4-(3,5-Dimethyl-4-phenyl-1H-pyrazol-1-yl)phenyl]ethyl}amino)carbonyl]-3-methoxybenzenesulfonamide Mono-sodium Salt The title compound was prepared according to the procedure described in step 4 of Example 8 from N-[({2-[4-(3,5-dimethyl-4-phenyl-1H-pyrazol-1-yl)phenyl]ethyl}amino)carbonyl]-3-methoxybenzenesulfonamide (step 1): MS (ESI) m/z 505 [M+H]$^+$, 503 [M–H]$^-$.

Example 42

N-[({2-[4-(3,5-Dimethyl-4-phenyl-1H-pyrazol-1-yl)phenyl]ethyl}amino)carbonyl]-4-hydroxybenzenesulfonamide Di-sodium Salt Step 1. N-[({2-[4-(3,5-Dimethyl-4-phenyl-1H-pyrazol-1-yl)phenyl]ethyl}amino)carbonyl]-4-hydroxybenzenesulfonamide A mixture of phenyl 2-[4-(3,5-dimethyl-4-phenyl-1H-pyrazol-1-yl)phenyl]ethylcarbamate (step 1 of Example 22, 100 mg, 0.24 mmol), 4-hydroxybenzenesulfonamide (42 mg, 0.24 mmol), acetonitrile (3 mL) and 1,8-[5.4.0]-7-undecene (36 μL, 0.24 mmol) was stirred at room temperature for 16 h. The mixture was diluted with dichloromethane, and washed with 1 M hydrochloric acid and sat. NaHCO$_3$ aq. The organic fraction was dried over MgSO$_4$ and concentrated under reduced pressure. The residue was purified by TLC with dichloromethane/methanol (10:1) to afford 89 mg (74%) of the title compound as white solids: $^1$H-NMR [CDCl$_3$/CD$_3$OD(4:1)] δ 7.73–7.68 (2H, m), 7.48–7.23 (9H, m), 6.88–6.83 (2H, m), 3.47 (2H, t, J=6.7 Hz), 2.84 (2H, t, J=6.7 Hz), 2.33 (3H, s), 2.26 (3H, s).

Step 2. N-[({2-[4-(3,5-Dimethyl-4-phenyl-1H-pyrazol-1-yl)phenyl]ethyl}amino)carbonyl]-4-hydroxybenzenesulfonamide Di-sodium Salt The title compound was prepared according to the procedure described in step 4 of Example 8 from N-[({2-[4-(3,5-dimethyl-4-phenyl-1H-pyrazol-1-yl)phenyl]ethyl}amino)carbonyl]-4-hydroxybenzenesulfonamide (step 1): MS (ESI) m/z 491 [M+H]$^+$, 489 [M–H]$^-$.

Example 43

N-[({2-[4-(3,5-Dimethyl-4-phenyl-1H-pyrazol-1-yl)phenyl]ethyl}amino)carbonyl]-3-hydroxybenzenesulfonamide di-sodium salt Step 1. N-[({2-[4-(3,5-Dimethyl-4-phenyl-1H-pyrazol-1-yl)phenyl]ethyl}amino)carbonyl]-3-hydroxybenzenesulfonamide The title compound was prepared according to the procedure described in step 1 of Example 42 from phenyl 2-[4-(3,5-dimethyl-4-phenyl-1H-pyrazol-1-yl)phenyl]ethylcarbamate (step 1 of Example 22) and 3-hydroxybenzenesulfonamide [*Tetrahedron Lett.*, 1993, 34, 2043]: $^1$H-NMR (CDCl$_3$) δ 7.49–7.20 (11H, m), 7.05–7.00 (1H, m), 6.56 (1H, br.s), 6.17 (1H, br.s), 3.59–3.52 (2H, m), 2.92 (2H, t, J=6.1 Hz), 2.36 (3H, s), 2.30 (3H, s).

Step 2. N-[({2-[4-(3,5-Dimethyl-4-phenyl-1H-pyrazol-1-yl)phenyl]ethyl}amino)carbonyl]-3-hydroxybenzenesulfonamide Di-sodium Salt The title compound was prepared according to the procedure described in step 4 of Example 8 from N-[({2-[4-(3,5-dimethyl-4-phenyl-1H-pyrazol-1-yl)phenyl]ethyl}amino)carbonyl]-3-hydroxybenzenesulfonamide (step 1): MS (ESI) m/z 491 [M+H]$^+$, 489 [M–H]$^-$.

Example 44

N-[({2-[4-(3,5-Dimethyl-4-phenyl-1H-pyrazol-1-yl)phenyl]ethyl}amino)carbonyl]-2-hydroxybenzenesulfonamide Di-sodium Salt Step 1. N-[({2-[4-(3,5-Dimethyl-4-phenyl-1H-pyrazol-1-yl)phenyl]ethyl}amino)carbonyl]-2-hydroxybenzenesulfonamide The title compound was prepared according to the procedure described in step 1 of Example 42 from phenyl 2-[4-(3,5-dimethyl-4-phenyl-1H-pyrazol-1-yl)phenyl]ethylcarbamate (step 1 of Example 22) and 2-hydroxybenzenesulfonamide [*Synth. Commun.*, 1994, 24, 671]: $^1$H-NMR (CDCl$_3$) δ 7.74–7.70 (1H, m), 7.48–7.24 (9H, m), 7.15 (2H, d, J=8.2 Hz), 7.02 (1H, d, J=7.7 Hz), 6.93 (1H, t, J=7.6 Hz), 6.16 (1H, br.s), 3.47–3.40 (2H, m), 2.81 (2H, t, J=6.5 Hz), 2.32 (3H, s), 2.23 (3H, s).

Step 2. N-[({2-[4-(3,5-Dimethyl-4-phenyl-1H-pyrazol-1-yl)phenyl]ethyl}amino)carbonyl]-2-hydroxybenzenesulfonamide di-sodium salt The title compound was prepared according to the procedure described in step 4 of Example 8 from N-[({2-[4-(3, 5-dimethyl-4-phenyl-1H-pyrazol-1-yl)phenyl]ethyl}amino) carbonyl]-2-hydroxybenzenesulfonamide (step 1): MS (ESI) m/z 491 [M+H]$^+$, 489 [M−H]$^−$.

Example 45

N-[({2-[4-(3,5-Dimethyl-4-phenyl-1H-pyrazol-1-yl) phenyl]ethyl}amino)carbonyl]-2,4-difluorobenzenesulfonamide Mono-sodium Salt Step 1. N-[({2-[4-(3,5-Dimethyl-4-phenyl-1H-pyrazol-1-yl) phenyl]ethyl}amino)carbonyl]-2,4-difluorobenzenesulfonamide The title compound was prepared according to the procedure described in step 1 of Example 42 from phenyl 2-[4-(3,5-dimethyl-4-phenyl-1H-pyrazol-1-yl)phenyl] ethylcarbamate (step 1 of Example 22) and 2,4-difluorobenzenesulfonamide: $^1$H-NMR (CDCl$_3$) δ 7.98–7.90 (1H, m), 7.47–7.41 (2H, m), 7.35–7.22 (7H, m), 7.07–6.92 (2H, m), 6.16 (1H, br.s), 3.50–3.43 (2H, m), 2.84 (2H, t, J=6.6 Hz), 2.33 (3H, s), 2.23 (3H, s).

Step 2. N-[({2-[4-(3,5-Dimethyl-4-phenyl-1H-pyrazol-1-yl) phenyl]ethyl}amino)carbonyl]-2,4-difluorobenzenesulfonamide Mono-sodium Salt The title compound was prepared according to the procedure described in step 4 of Example 8 from N-[({2-[4-(3, 5-dimethyl-4-phenyl-1H-pyrazol-1-yl)phenyl]ethyl}amino) carbonyl]-2,4-difluorobenzenesulfonamide (step 1): MS (ESI) m/z 511 [M+H]$^+$, 509 [M−H]$^−$.

Example 46

N-[({2-[4-(3,5-Dimethyl-4-phenyl-1H-pyrazol-1-yl) phenyl]ethyl}amino)carbonyl]-4-ethoxybenzenesulfonamide Mono-sodium Salt Step 1. N-[({2-[4-(3,5-Dimethyl-4-phenyl-1H-pyrazol-1-yl) phenyl]ethyl}amino)carbonyl]-4-ethoxybenzenesulfonamide The title compound was prepared according to the procedure described in step 1 of Example 42 from phenyl 2-[4-(3,5-dimethyl-4-phenyl-1H-pyrazol-1-yl)phenyl] ethylcarbamate (step 1 of Example 22) and 4-ethoxybenzenesulfonamide [Chem. Ber., 1982, 25, 1838]: $^1$H-NMR (CDCl$_3$) δ 7.74 (2H, d, J=8.9 Hz), 7.47–7.24 (9H, m), 6.95–6.92 (21H, in), 6.40 (1H, br.s), 4.07 (2H, q, J=7.1 Hz), 3.53–3.46 (2H, m), 2.86 (2H, t, J=6.8 Hz), 2.33 (3H, s), 2.26 (3H, s), 1.42 (3H, t, J=7.1 Hz).

Step 2. N-[({2-[4-(3,5-Dimethyl-4-phenyl-1H-pyrazol-1-yl) phenyl]ethyl}amino) carbonyl]-4-ethoxybenzenesulfonamide mono-sodium salt The title compound was prepared according to the procedure described in step 4 of Example 8 from N-[({2-[4-(3, 5-dimethyl-4-phenyl-1H-pyrazol-1-yl)phenyl]ethyl}amino) carbonyl]-4-ethoxybenzenesulfonamide (step 1): MS (ESI) m/z 519 [M+H]$^+$, 517 [M−H]$^−$.

Example 47

N-[({2-[4-(3,5-Dimethyl-4-phenyl-1H-pyrazol-1-yl) phenyl]ethyl}amino)carbonyl]-3,4-difluorobenzenesulfonamide Mono-sodium Salt Step 1. N-[({2-[4-(3,5-Dimethyl-4-phenyl-1H-pyrazol-1-yl) phenyl]ethyl}amino)carbonyl]-3,4-difluorobenzenesulfonamide The title compound was prepared according to the procedure described in step 1 of Example 42 from phenyl 2-[4-(3,5-dimethyl-4-phenyl-1H-pyrazol-1-yl)phenyl] ethylcarbamate (step 1 of Example 22) and 3,4-difluorobenzenesulfonamide: $^1$H-NMR (CDCl$_3$) δ 7.84–7.70 (2H, m), 7.47–7.21 (10H, m), 6.07 (1H, br.s), 3.50–3.43 (2H, m), 2.85 (2H, t, J=6.3 Hz), 2.32 (3H, s), 2.22 (3H, s).

Step 2. N-[({2-[4-(3,5-Dimethyl-4-phenyl-1H-pyrazol-1-yl) phenyl]ethyl}amino)carbonyl]-3,4-difluorobenzenesulfonamide Mono-sodium Salt The title compound was prepared according to the procedure described in step 4 of Example 8 from N-[({2-[4-(3, 5-dimethyl-4-phenyl-1H-pyrazol-1-yl)phenyl]ethyl}amino) carbonyl]-3,4-difluorobenzenesulfonamide (step 1): MS (ESI) m/z 511 [M+H]$^+$, 509 [M−H]$^−$.

Example 48

3-Cyano-N-[({2-[4-(3,5-dimethyl-4-phenyl-1H-pyrazol-1-yl)phenyl]ethyl}amino)carbonyl] benzenesulfonamide Mono-sodium Salt Step 1. 3-Cyano-N-[({2-[4-(3,5-dimethyl-4-phenyl-1H-pyrazol-1-yl)phenyl]ethyl}amino)carbonyl] benzenesulfonamide The title compound was prepared according to the procedure described in step 1 of Example 42 from phenyl 2-[4-(3,5-dimethyl-4-phenyl-1H-pyrazol-1-yl)phenyl] ethylcarbamate (step 1 of Example 22) and 3-cyanobenzenesulfonamide: $^1$H-NMR (CDCl$_3$) δ 8.26–8.21 (2H, m), 7.86 (1H, d, J=7.9 Hz), 7.68 (1H, t, J=7.9 Hz), 7.46–7.20 (9H, m), 6.01 (1H, br.s), 3.48–3.42 (2H, m), 2.84 (2H, t, J=6.3 Hz), 2.32 (3H, s), 2.21 (3H, s).

Step 2. 3-Cyano-N-[({2-[4-(3,5-dimethyl-4-phenyl-1H-pyrazol-1-yl)phenyl]ethyl}amino)carbonyl] benzenesulfonamide mono-sodium salt The title compound was prepared according to the procedure described in step 4 of Example 8 from 3-cyano-N-[({2-[4-(3,5-dimethyl-4-phenyl-1H-pyrazol-1-yl)phenyl] ethyl}amino)carbonyl]benzenesulfonamide (step 1): MS (ESI) m/z 500 [M+H]$^+$, 498 [M−H]$^−$.

Example 49

3-Chloro-N-[({2-[4-(3,5-dimethyl-4-phenyl-1H-pyrazol-1-yl)phenyl]ethyl}amino)carbonyl]-4-fluorobenzenesulfonamide mono-sodium salt Step 1. 3-Chloro-N-[({2-[4-(3,5-dimethyl-4-phenyl-1H-pyrazol-1-yl)phenyl]ethyl}amino)carbonyl]-4-fluorobenzenesulfonamide The title compound was prepared according to the procedure described in step 1 of Example 42 from phenyl 2-[4-(3,5-dimethyl-4-phenyl-1H-pyrazol-1-yl)phenyl] ethylcarbamate (step 1 of Example 22) and 3-chloro-4-fluorobenzenesulfonamide: $^1$H-NMR (CDCl$_3$) δ 8.03–8.01 (1H, m), 8.00–7.79 (1H, m), 7.46–7.21 (10H, m), 6.14 (1H, br.s), 3.49–3.42 (2H, m), 2.84 (2H, t, J=6.7 Hz), 2.31 (3H, s), 2.23 (3H, s).

Step 2. 3-Chloro-N-[({2-[4-(3,5-dimethyl-4-phenyl-1H-pyrazol-1-yl)phenyl]ethyl}amino)carbonyl]-4-fluorobenzenesulfonamide Mono-sodium Salt The title compound was prepared according to the procedure described in step 4 of Example 8 from 3-chloro-N-[({2-[4-(3,5-dimethyl-4-phenyl-1H-pyrazol-1-yl)phenyl] ethyl}amino)carbonyl]-4-fluorobenzenesulfonamide (step 1): MS (ESI) m/z 527 [M+H]$^+$, 525 [M−H]$^−$.

Example 50

N-[({2-[4-(3,5-Dimethyl-4-phenyl-1H-pyrazol-1-yl)phenyl]ethyl}amino)carbonyl]-2,6-difluorobenzenesulfonamide mono-sodium salt Step 1. N-[({2-[4-(3,5-Dimethyl-4-phenyl-1H-pyrazol-1-yl)phenyl]ethyl}amino)carbonyl]-2,6-difluorobenzenesulfonamide The title compound was prepared according to the procedure described in step 1 of Example 42 from phenyl 2-[4-(3,5-dimethyl-4-phenyl-1H-pyrazol-1-yl)phenyl]ethylcarbamate (step 1 of Example 22) and 2,6-difluorobenzenesulfonamide: $^1$H-NMR (CDCl$_3$) δ 7.44–7.19 (10H, m), 6.93 (2H, t, J=9.0 Hz), 6.52 (1H, br.s), 3.39–3.37 (2H, m), 2.79–2.74 (2H, m), 2.29 (3H, s), 2.20 (3H, s).

Step 2. N-[({2-[4-(3,5-Dimethyl-4-phenyl-1H-pyrazol-1-yl)phenyl]ethyl}amino)carbonyl]-2,6-difluorobenzenesulfonamide mono-sodium salt The title compound was prepared according to the procedure described in step 4 of Example 8 from N-[({2-[4-(3,5-dimethyl-4-phenyl-1H-pyrazol-1-yl)phenyl]ethyl}amino)carbonyl]-2,6-difluorobenzenesulfonamide (step 1): MS (ESI) m/z 511 [M+H]$^+$, 509 [M–H]$^-$.

Example 51

2-Chloro-N-[({2-[4-(3,5-dimethyl-4-phenyl-1H-pyrazol-1-yl)phenyl]ethyl}amino)carbonyl]-4-fluorobenzenesulfonamide Mono-sodium Salt Step 1. 2-Chloro-N-[({2-[4-(3,5-dimethyl-4-phenyl-1H-pyrazol-1-yl)phenyl]ethyl}amino)carbonyl]-4-fluorobenzenesulfonamide The title compound was prepared according to the procedure described in step 1 of Example 42 from phenyl 2-[4-(3,5-dimethyl-4-phenyl-1H-pyrazol-1-yl)phenyl]ethylcarbamate (step 1 of Example 22) and 2-chloro-4-fluorobenzenesulfonamide: $^1$H-NMR (CDCl$_3$) δ 8.12–8.07 (1H, m), 7.46–7.04 (11H, m), 6.29 (1H, br.s), 3.42–3.36 (2H, m), 2.79–2.75 (2H, m), 2.29 (3H, s), 2.21 (3H, s).

Step 2. 2-Chloro-N-[({2-[4-(3,5-dimethyl-4-phenyl-1H-pyrazol-1-yl)phenyl]ethyl}amino)carbonyl]-4-fluorobenzenesulfonamide mono-sodium salt The title compound was prepared according to the procedure described in step 4 of Example 8 from 2-chloro-N-[({2-[4-(3,5-dimethyl-4-phenyl-1H-pyrazol-1-yl)phenyl]ethyl}amino)carbonyl]-4-fluorobenzenesulfonamide (step 1): MS (ESI) m/z 527 [M+H]$^+$, 525 [M–H]$^-$.

Example 52

2,4-Difluoro-N-{[(2-{4-[5-methyl-4-phenyl-3-(trifluoromethyl)-1H-pyrazol-1-yl]phenyl}ethyl)amino]carbonyl}benzenesulfonamide Mono-sodium Salt Step 1. 2-{4-[5-Methyl-3-(trifluoromethyl)-1H-pyrazol-1-yl]phenyl}ethanol The title compound was prepared according to the procedure described in step 1 of Example 1 from 2-(4-hydrazinophenyl)ethanol hydrochloride and 1,1,1-trifluoro-2,4-pentanedione: MS (ESI) m/z 270 [M+H]$^+$, $^1$H-NMR (CDCl$_3$) δ 7.41–7.34 (4H, m), 6.45 (1H, s), 3.93–3.86 (211, m), 2.94 (2H, t, J=6.6 Hz), 2.34 (3H, s).

Step 2. 2-{4-[4-Bromo-5-methyl-3-(trifluoromethyl)-1H-pyrazol-1-yl]phenyl}ethanol A mixture of 2-{4-[5-methyl-3-(trifluoromethyl)-1H-pyrazol-1-yl]phenyl} ethanol (step 450 mg, 1.67 mmol) and bromine (293 mg, 1.83 mmol) in chloroform (10 mL) was stirred at room temperature overnight. The organic solution was washed with 5% aqueous solution sodium thiosulfate, then with brine, and finally dried (Na$_2$SO$_4$) and evaporated. The crude product was purified by TLC with hexane/ethyl acetate (1:1) to afford 451 mg (77%) of the title compound as yellow solids: MS (EI) m/z 348 [M]$^+$, $^1$H-NMR (CDCl$_3$) δ 7.37 (4H, s), 3.89 (2H, br.s), 2.94 (2H, t, J=6.4 Hz), 2.33 (3H, s).

Step 3. 2-{4-[5-Methyl-4-phenyl-3-(trifluoromethyl)-1H-pyrazol-1-yl]phenyl}ethanol The title compound was prepared according to the procedure described in step 1 of Example 12 from 2-{4-[4-bromo-5-methyl-3-(trifluoromethyl)-1H-pyrazol-1-yl]phenyl}ethanol (step 2) and phenylboronic acid: MS (ESI) m/z 346 [M+H]$^+$, $^1$H-NMR (CDCl$_3$) δ 7.44–7.32 (9H, m), 3.89–3.83 (2H, m), 2.94–2.89 (2H, m), 2.33 (3H, s), 2:32 (3H, s)

Step 4. 2-{4-[5-Methyl-4-phenyl-3-(trifluoromethyl)-1H-pyrazol-1-yl]phenyl}ethyl methanesulfonate The title compound was prepared according to the procedure described in step 2 of Example 59 from 2-{4-[5-methyl-4-phenyl-3-(trifluoromethyl)-1H-pyrazol-1-yl]phenyl}ethanol: MS (ESI) m/z 425 [M+H]$^+$.

Step 5. 1-[4-(2-Azidoethyl)phenyl]-5-methyl-4-phenyl-3-(trifluoromethyl)-1H-pyrazole The title compound was prepared according to the procedure described in step 3 of Example 59 from 2-{4-[5-methyl-4-phenyl-3-(trifluoromethyl)-1H-pyrazol-1-yl]phenyl}ethyl methanesulfonate (step 4): MS (ESI) m/z 372 [M+H$^+$, $^1$H-NMR (CDCl$_3$) δ 7.48–7.34 (4H, m), 3.56 (2H, t, J=7.1 Hz), 2.97 (2H, t, J=7.1 Hz), 2.25 (3H, s).

Step 6. 2-{4-[5-Methyl-4-phenyl-3-(trifluoromethyl)-1H-pyrazol-1-yl]phenyl}ethanamine The title compound was prepared according to the procedure described in step 3 of Example 14 from 1-[4-(2-azidoethyl)phenyl]-5-methyl-4-phenyl-3-(trifluoromethyl)-1H-pyrazole (step 5): MS (ESI) m/z 346 [M+H]$^+$.

Step 7. Phenyl 2-{4-[5-methyl-4-phenyl-3-(trifluoromethyl)-1H-pyrazol-1-yl]phenyl}ethylcarbamate The title compound was prepared according to the procedure described in step 1 of Example 22 from 2-{4-[5-methyl-4-phenyl-3-(trifluoromethyl)-1H-pyrazol-1-yl]phenyl}ethanamine (step 6): MS (ESI) m/z 466 [M+H]$^+$.

Step 8. 2,4-Difluoro-N-{[(2-{4-[5-methyl-4-phenyl-3-(trifluoromethyl)-1H-pyrazol-1-yl]phenyl ethyl)amino]carbonyl}benzenesulfonamide The title compound was prepared according to the procedure described in step 1 of Example 42 from phenyl 2-{4-[5-methyl-4-phenyl-3-(trifluoromethyl)-1H-pyrazol-1-yl]phenyl}ethylcarbamate (step 7) and 2,4-difluorobenzenesulfonamide: MS (ESI) m/Z 565 [M+H]$^+$, 563 [M–H]$^-$, $^1$H-NMR (CDCl$_3$) δ 7.90–7.85 (1H, m), 7.48–7.27 (9H, m), 7.10–6.92 (2H, m), 6.29 (]1H, br.s), 3.53–3.47 (211, m), 2.88 (2H, t, J=6.8 Hz), 2.23 (3H, s).

Step 9. 4-Difluoro-N-{[(2–4-[5-methyl-4-phenyl-3-(trifluoromethyl)-1H-pyrazol-1-yl]phenyl}ethyl)amino]carbonyl}benzenesulfonamide mono-sodium salt The title compound was prepared according to the procedure described in step 4 of Example 8 from 2,4-difluoro-N-{[(2-{4-[5-methyl-4-phenyl-3-(trifluoromethyl)-1H-pyrazol-1-yl]phenyl}ethyl)amino]carbonyl}benzenesulfonamide (step 8): MS (ESI) m/z: 565 [M+H]$^+$, 563 [M–H]$^-$.

Example 53

2-Fluoro-N-{[(2-[4-[5-methyl-4-phenyl-3-(trifluoromethyl)-1H-pyrazol-1-yl]phenyl}ethyl)amino]carbonyl)Benzenesulfonamide Mono-sodium Salt Step 1. 2-Fluoro-N-{[(2-{4-[5-methyl-4-phenyl-3-(trifluoromethyl)-1H-pyrazol-1-yl]phenyl}ethyl)amino]carbonyl}benzenesulfonamide The title compound was prepared according to the procedure described in step 1 of Example 42 from phenyl 2-{4-[5-methyl-4-phenyl-3-(trifluoromethyl)-1H-pyrazol-1-yl]phenyl}ethylcarbamate (step 7 of Example 52) and 2-fluoro-benzenesulfonamide: MS (ESI) m/z 547 [M+H]$^+$, 545 [M−H]$^−$, $^1$H-NMR (CDCl$_3$) δ 7.86–7.81 (1H, m), 7.74–7.58 (1H, m), 7.48–7.24 (1H, m), 6.45 (1H, br.s) 3.54–3.49 (2H, m), 2.87 (2H, t, J=6.7 Hz), 2.23 (3H, s).

Step 2. 2-Fluoro-N-{[(2-{4-[5-methyl-4-phenyl-3-(trifluoromethyl)-1H-pyrazol-1-yl]phenyl}ethyl)amino]carbonyl}benzenesulfonamide, mono-sodium salt The title compound was prepared according to the procedure described in step 4 of Example 8 from 2-fluoro-N-{[(2-{4-[5-methyl-4-phenyl-3-(trifluoromethyl)-1H-pyrazol-1-yl]phenyl}ethyl)amino]carbonyl}benzenesulfonamide (step 1): MS (ESI) m/z 547 [M+H]$^+$, 545 [M−H]$^−$.

Example 54

3-Chloro-N-[({2-[4-(3,5-dimethyl-4-phenyl-1H-pyrazol-1--yl)phenyl]ethyl}amino)carbonyl]-2-pyridinesulfonamide Mono-sodium Salt Step 1. 3-Chloro-N-[({2-[4-(3,5-dimethyl-4-phenyl-1H-pyrazol-1-yl)phenyl]ethyl}amino)carbonyl]-2-pyridinesulfonamide The title compound was prepared according to the procedure described in step 1 of Example 42 from phenyl 2-[4-(3,5-dimethyl-4-phenyl-1H-pyrazol-1-yl)phenyl]ethylcarbamate (step 1 of Example 22) and 3-chloro-2-pyridinesulfonamide (U.S. Pat. No. 4,490,380): $^1$H-NMR (DMSO-d$_6$) δ 8.62 (1H, d, J=4.3 Hz), 8.20 (1H, d, J=7.9 Hz), 7.71–7.67 (1H, m), 7.49–7.31 (9H, m), 6.57 (1H, br.s), 3.37–3.28 (2H, m), 2.79–2.74 (2H, m), 2.27 (3H, s), 2.23 (3H, s).

Step 2. 3-Chloro-N-[({2-[4-(3,5-dimethyl-4-phenyl-1H-pyrazol-1-yl)phenyl]ethyl}amino)carbonyl]-2-pyridinesulfonamide mono-sodium salt The title compound was prepared according to the procedure described in step 4 of Example 8 from 3-chloro-N-[({2-[4-(3,5-dimethyl-4-phenyl-1H-pyrazol-1-yl)phenyl]ethyl}amino)carbonyl]-2-pyridinesulfonamide (step 1): MS (ESI) m/z 510 [M+H]$^+$, 508 [M−H]$^−$.

Example 55

5-Chloro-N-[({2-[4-(3,5-dimethyl-4-phenyl-1H-pyrazol-1-yl)phenyl]ethyl}amino)carbonyl]-2-pyridinesulfonamide Mono-sodium Salt Step 1. 5-Chloro-N-[({2-[4-(3,5-dimethyl-4-phenyl-1H-pyrazol-1-yl)phenyl]ethyl}amino)carbonyl]-2-pyridinesulfonamide The title compound was prepared according to the procedure described in step 1 of Example 42 from phenyl 2-[4-(3,5-dimethyl-4-phenyl-1H-pyrazol-1-yl)phenyl]ethylcarbamate (step 1 of Example 22) and 5-chloro-2-pyridinesulfonamide (DK Patent 107422): $^1$H-NMR (CDCl$_3$) δ 8.59 (1H, d, J=1.8 Hz), 8.00–7.90 (2H, m), 7.46–7.22 (9H, m), 6.52 (1H, br.s), 3.48–3.41 (2H, m), 2.85–2.80 (2H, m), 2.33 (3H, s), 2.24 (3H, s).

Step 2. 5-Chloro-N-[({2-[4-(3,5-dimethyl-4-phenyl-1H-pyrazol-1-yl)phenyl]ethyl}amino)carbonyl]-2-pyridinesulfonamide mono-sodium salt The title compound was prepared according to the procedure described in step 4 of Example 8 from 5-chloro-N-[({2-[4-(3,5-dimethyl-4-phenyl-1H-pyrazol-1-yl)phenyl]ethyl}amino)carbonyl]-2-pyridinesulfonamide (step 1): MS (ESI) m/z 510 [M+H]$^+$, 508 [M−H]$^−$.

Example 56

4-Acetyl-N-[({2-[4-(3,5-dimethyl-4-phenyl-1H-pyrazol-1-yl)phenyl]ethyl}amino)carbonyl]benzenesulfonamide Mono-sodium Salt Step 1. 4-Acetyl-N-[(2-[4-(3,5-dimethyl-4-phenyl-1H-pyrazol-1-yl)phenyl]ethyl]amino)carbonyl]benzenesulfonamide The title compound was prepared according to the procedure described in step 1 of Example 42 from phenyl 2-[4-(3,5-dimethyl-4-phenyl-1H-pyrazol-1-yl)phenyl]ethylcarbamate (step 1 of Example 22) and 4-acetylbenzenesulfonamide: $^1$H-NMR (DMSO-d$_6$) δ 8.13 (2H, d, J=8.6 Hz), 7.99 (2H, d, J=8.6 Hz), 7.49–7.26 (9H, m), 6.62–6.58 (1H, m), 3.29–3.22 (2H, m), 2.75–2.70 (2H, m), 2.62 (3H, s), 2.26 (3H, s), 2.23 (3H, s).

Step 2. 4-Acetyl-N-[({2-[4-(3,5-dimethyl-4-phenyl-1H-pyrazol-1-yl)phenyl]ethyl}amino)carbonyl]benzenesulfonamide mono-sodium salt The title compound was prepared according to the procedure described in step 4 of Example 8 from 4-acetyl-N-[({2-[4-(3,5-dimethyl-4-phenyl-1H-pyrazol-1-yl)phenyl]ethyl}amino)carbonyl]benzenesulfonamide (step 1): MS (ESI) m/z 517 [M+H]$^+$, 515 [M−H]$^−$.

Example 57

3-({[({2-[4-(3,5-Dimethyl-4-phenyl-1H-pyrazol-1-yl)phenyl]ethyl}amino)carbonyl]amino} Sulfonyl)benzamide Mono-sodium Salt Step 1. 3-({[({2-[4-(3,5-Dimethyl-4-phenyl-1H-pyrazol-1-yl)phenyl]ethyl}amino) carbonyl]amino}sulfonyl)benzamide The title compound was prepared according to the procedure described in step 1 of Example 42 from phenyl 2-[4-(3,5-dimethyl-4-phenyl-1H-pyrazol-1-yl)phenyl]ethylcarbamate (step 1 of Example 22) and 3-(aminosulfonyl)benzamide: $^1$H-NMR (CDCl$_3$) δ 8.47 (1H, s), 8.01 (2H, d, J=8.9 Hz), 7.60–7.11 (10H, m), 6.70 (1H, br.s), 6.30 (1H, br.s), 3.38–3.35 (2H, m), 2.77–2.71 (2H, m), 2.29 (3H, s), 2.17 (3H, s).

Step 2. 3-({[({2-[4-(3,5-Dimethyl-4-phenyl-1H-pyrazol-1-yl)phenyl]ethyl}amino) carbonyl]amino} sulfonyl)benzamide mono-sodium salt The title compound was prepared according to the procedure described in step 4 of Example 8 from 3-({[({2-[4-(3,5-dimethyl-4-phenyl-1H-pyrazol-1-yl)phenyl]ethyl}amino)carbonyl]amino}sulfonyl)benzamide (step 1): MS (ESI) m/z 518 [M+H]$^+$, 516 [M−H]$^−$.

Example 58

N-[({2-[4-(3,5-Dimethyl-4-phenyl-1H-pyrazol-1-yl)phenyl]ethyl}amino)carbonyl]-1,3-benzenedisulfonamide Mono-sodium Salt Step 1. N-[({2-[4-(3,5-Dimethyl-4-phenyl-1H-pyrazol-1-yl)phenyl]ethyl}amino) carbonyl]-1,3-benzenedisulfonamide The title compound was prepared according to the procedure described in step 1 of Example 42 from phenyl 2-[4-(3,5-dimethyl-4-phenyl-1H-pyrazol-1-yl)phenyl] ethylcarbamate (step 1 of Example 22) and 1,3-benzenedisulfonamide: $^1$H-NMR (CDCl$_3$) δ 8.47 (1H, s), 8.05–7.95 (2H, m), 7.52–7.09 (10H, m), 6.27 (1H, br.s), 3.37–3.28 (2H, m), 2.75–2.64 (2H, m), 2.17 (3H, s), 2.13 (3H, s).

Step 2. N-[({2-[4-(3,5-Dimethyl-4-phenyl-1H-pyrazol-1-yl) phenyl]ethyl) amino)carbonyl]-1,3-benzenedisulfonamide mono-sodium salt The title compound was prepared according to the procedure described in step 4 of Example 8 from N-[({2-[4-(3,5-dimethyl-4-phenyl-1H-pyrazol-1-yl)phenyl]ethyl}amino) carbonyl]-1,3-benzenedisulfonamide (step 1): MS (ESI) m/z 554 [M+H]$^+$, 552 [M–H]$^-$.

Example 59

3-[3,5-Dimethyl-1-(4-{2-[({[(4-methylphenyl) sulfonyl]amino}carbonyl)amino]ethyl} phenyl)-1H-pyrazol-4-yl]benzamide Mono-sodium Salt Step 1. Methyl 3–11-[4-(2-hydroxyethyl)phenyl]-3,5-dimethyl-1H-pyrazol-4-yl}benzoate The title compound was prepared according to the procedure described in step 1 of Example 12 from 2-[4-(4-iodo-3,5-dimethyl-1H-pyrazol-1-yl)phenyl]ethanol (step 2 of Example 11) and (3-methoxycarbonylphenyl)boronic acid: MS (EI) m/z 350 [M]+, $^1$H-NMR (CDCl$_3$) δ 8.02 (2H, br.s), 7.71–7.53 (10H, m), 3.91 (2H, t, J=6.4 Hz), 2.94 (2H, t, J=6.4 Hz), 2.33 (3H, s), 2.30 (3H, s).

Step 2. Methyl 3-[3,5-dimethyl-1-(4-{2-[(methylsulfonyl) oxy]ethyl}phenyl)-1H-pyrazol-4-yl]benzoate To a solution of methyl 3-{1-[4-(2-hydroxyethyl)phenyl]-3,5-dimethyl-1H-pyrazol-4-yl}benzoate (step 1, 700 mg, 2.0 mmol) in dichloromethane (10 mL) was added methanesulfonylchloride (0.23 mL, 3.0 mmol) and triethylamine (0.73 mL, 10 mmol) and the resulting mixture was stirred at room temperature for 1.5 h. The reaction mixture was quenched by water and extracted with dichloromethane. Organic layer was dried (Na$_2$SO$_4$) and the solvent was evaporated to give the title compound as brown oil (quant.): MS (ESI) m/z 429 [M+H]$^+$, $^1$H-NMR (CDCl$_3$) δ 8.01 (2H, s), 7.53–7.36 (6H, m), 4.46 (2H, t, J=6.8 Hz), 3.94 (3H, s), 3.13 (2H, t, J=6.8 Hz), 2.92 (3H, s), 2.33 (3H, s), 2.30 (3H, s).

Step 3. Methyl 3-{1-[4-(2-azidoethyl)phenyl]-3,5-dimethyl-1H-pyrazol-4-yl}benzoate To a stirred solution of methyl 3-[3,5-dimethyl-1-(4-{2-[(methylsulfonyl)oxy]ethyl}phenyl)-1H-pyrazol-4-yl] benzoate (step 2, 2.0 mmol) and KI (330 mg, 2.0 mmol) in N,N-dimethylformamide (10 mL) was added sodium azide (260 mg, 4.0 mmol), and then the resulting mixture was stirred for 1.5 h at 100° C. The reaction mixture was poured into water (100 mL), and extracted with ethyl acetate/toluene (4:1). The organic layer was washed with water (50 mL) and brine (50 mL), then dried (Na$_2$SO$_4$). After removal of the solvent, the crude product was purified by TLC with hexane/ethyl acetate (1:1) to give the title compound as yellow oil (quant.): $^1$H-NMR (CDCl$_3$) δ 8.01 (2H, s), 7.53–7.34 (6H, m), 3.95 (3H, s), 3.55 (2H, t, J=7.1 Hz), 2.96 (2H, t, J=7.1 Hz), 2.33 (3H, s), 2.30 (3H, s).

Step 4. Methyl 3-{1-[4-(2-aminoethyl)phenyl]-3,5-dimethyl-1H-pyrazol-4-yl}benzoate The title compound was prepared according to the procedure described in step 3 of Example 14 from methyl 3-{1-[4-(2-azidoethyl)phenyl]-3,5-dimethyl-1H-pyrazol-4-yl}benzoate (step 3): MS (ESI) m/z 350 [M+H]$^+$.

Step 5. Methyl 3-[3,5-dimethyl-1-(4-{2-[({[(4-methylphenyl)sulfonyl]amino}carbonyl)amino] ethyl}phenyl)-1H-pyrazol-4-yl]benzoate The title compound was prepared according to the procedure described in step 4 of Example 14 from methyl 3-{1-[4-(2-aminoethyl)phenyl]-3,5-dimethyl-1H-pyrazol-4-yl}benzoate (step 4): MS (ESI) m/z 547 [M+H]$^+$, 545 [M–H]$^-$, $^1$H-NMR (CDCl$_3$) δ 7.99 (2H, s), 7.78 (2H, m), 7.49 (2H, m), 7.32–7.21 (6H, m), 6.39 (1H, br.s), 3.91 (3H, s), 3.43 (2H, t, J=6.6 Hz), 2.81 (2H, t, J=6.6 Hz), 2.38 (3H, s), 2.29 (3H, s), 2.23 (3H, s).

Step 6. 3-[3,5-Dimethyl-1-(4-{2-[({[(4-methylphenyl) sulfonyl]amino}carbonyl) amino]ethyl}phenyl)-1H-pyrazol-4-yl]benzoic Acid To a stirred solution of methyl 3-[3,5-dimethyl-1-(4-{2-[({[(4-methylphenyl)sulfonyl]amino}carbonyl)amino] ethyl}phenyl)-1H-pyrazol-4-yl]benzoate (step 5, 1.1 mmol) in tetrahydrofuran (20 mL) and methanol (20 mL) was added 2 M NaOH aq. (10 mL), and then the resulting mixture was refluxed for 3 h. After removal of the solvent, the crude product was partitioned between saturated citric acid aq. (40 mL) and dichloromethane (50 mL). The organic layer was dried (Na$_2$SO$_4$). After removal of the solvent, the crude product was purified by TLC with dichloromethane/methanol (10:1) to afford 500 mg (87%) of the title compound as white solids: MS (ESI) m/z 533 [M+H]$^+$, 531 [M–H]$^-$, $^1$H-NMR (CDCl$_3$) δ 8.05 (2H, s), 7.71–7.29 (6H, m), 3.55 (2H, t, J=6.1 Hz), 2.88 (2H, t, J=6.1 Hz), 2.42 (3H, s), 2.34 (3H, s), 2.27 (3H, s).

Step 7. 3-[3,5-Dimethyl-1-(4-{2-[({[(4-methylphenyl) sulfonyl]amino}carbonyl) amino]ethyl}phenyl)-1H-pyrazol-4-yl]benzamide To a solution of 3-[3,5-dimethyl-1-(4-{2-[({[(4-methylphenyl)sulfonyl]amino}carbonyl)amino] ethyl}phenyl)-1H-pyrazol-4-yl]benzoic acid (step 6, 270 mg, 0.52 mmol) in N,N-dimethylformamide (1 mL) was added ammonium bicarbonate (45 mg, 0.57 mmol), pyridine (0.35 mL) and a solution of di-t-butyldicarbonate (120 mg, 0.57 mmol) in N,N-dimethylformamide (1 mL). The mixture was stirred at room temperature for 1 day. After dilution with water (10 mL), extraction with ethyl acetate (30 mL×3) was followed. The organic layer was dried (Na$_2$SO$_4$) and the solvent was removed under reduced pressure. The crude products was purified by TLC with dichloromethane/methanol (10:1) to afford 46 mg (10%) of the title compound as white solids: MS (ESI) m/z 532 [M+H]$^+$, 530 [M–H]$^-$.

Step 8. 3-[3,5-Dimethyl-1-(4-{2-[({[(4-methylphenyl) sulfonyl]amino}carbonyl)amino]ethyl}phenyl)-1H-pyrazol-4-yl]benzamide mono-sodium salt The title compound was prepared according to the procedure described in step 4 of Example 8 from 3-[3,5-dimethyl-1-(4-{2-[({[(4-methylphenyl)sulfonyl] amino}carbonyl)amino]ethyl}phenyl)-1H-pyrazol-4-yl] benzamide (step 7). MS (ESI) m/z 532 [M+H]$^+$, 530 [M–H]$^-$, $^1$H-NMR (CDCl$_3$) δ 8.04 (1H, s), 7.64 (1H, s), 7.47–7.41 (6H, m), 7.21–0.03 (5H, m), 5.70 (1H, br.s), 3.07 (2H, br.s), 2.55 (2H, br.s), 2.13 (3H, s), 2.08 (3H, s), 2.07 (3H, s).

Example 60

3-[1-(4-{2-[({[(2-Fluorophenyl)sulfonyl] amino}carbonyl) amino]ethyl}phenyl)-3,5-dimethyl-1H-pyrazol-4-yl]benzamide Step 1. 3-{1-[4-(2-Hydroxyethyl)phenyl]-3,5-dimethyl-1H-pyrazol-4-yl}benzonitrile The title compound was prepared according to the procedure described in step 1 of Example 12 from 2-[4-(4-iodo- 3,5-dimethyl-1H-pyrazol-1-yl)phenyl]ethanol (step 2 of Example 11) and 3-cyanobenzeneboronic acid: MS (EI) m/z 317 [M]+, $^1$H-NMR (CDCl$_3$) δ 7.63–7.34 (8H, m), 3.92 (2H, t, J=6.6 Hz), 2.94 (2H, t, J=6.6 Hz), 2.32 (3H, s), 2.29 (3H, s).

Step 2. 3-{1-[4-(2-Chloroethyl)phenyl]-3,5-dimethyl-1H-pyrazol-4-yl}benzonitrile The title compound was prepared according to the procedure described in step 1 of Example 14 from 3-{1-[4-(2-hydroxyethyl)phenyl]-3,5-dimethyl-1H-pyrazol-4-yl}benzonitrile (step 1): MS (ESI) m/z 336 [M+H]$^+$, $^1$H-NMR (CDCl$_3$) δ 7.62–7.16 (8H, m), 3.75 (2H, t, J=7.4 Hz), 3.13 (2H, t, J=7.4 Hz), 2.35 (3H, s), 2.29 (3H, s).

Step 3. 3-{1-[4-(2-Chloroethyl)phenyl]-3,5-dimethyl-1H-pyrazol-4-yl}benzamide

A solution of 3-{1-[4-(2-chloroethyl)phenyl]-3,5-dimethyl-1H-pyrazol-4-yl}benzonitrile (step 2, 2.62 mmol) in conc. H$_2$SO$_4$ was heated at 80° C. for 5 h. It was neutralized by 5 M NaOH aq. and extracted with dichloromethane. Organic phase was dried over Na$_2$SO$_4$ and the solvent was removed under reduced pressure to afford 780 mg (84%) of the title compound as yellow solids: MS (ESI) m/z 354 [M+H]$^+$, $^1$H-NMR (CDCl$_3$) δ 7.80–7.36 (8H, m), 3.75 (2H, t, J=7.2 Hz), 3.14 (2H, t, J=7.2 Hz), 2.33 (3H, s), 2.31 (3H, s).

Step 4. 3-{1-[4-(2-Azidoethyl)phenyl]-3,5-dimethyl-1H-pyrazol-4-yl}benzamide

The title compound was prepared according to the procedure described in step 2 of Example 14 from 3-{1-[4-(2-chloroethyl)phenyl]-3,5-dimethyl-1H-pyrazol-4-yl}benzamide (step 3): MS (ESI) m/z 361 [M+H]$^+$.

Step 5. 3-{1-[4-(2-Aminoethyl)phenyl]-3,5-dimethyl-1H-pyrazol-4-yl}benzamide

The title compound was prepared according to the procedure described in step 3 of Example 14 from 3-{1-[4-(2-azidoethyl)phenyl]-3,5-dimethyl-1H-pyrazol-4-yl}benzamide (step 4): MS (ESI) m/z 335 [M+H]$^+$, $^1$H-NMR (CDCl$_3$) δ 8.02–7.17 (8H, m), 3.01 (2H, t, J=6.7 Hz), 2.82 (2H, t, J=6.7 Hz), 2.33 (3H, s), 2.30 (3H, s).

Step 6. Phenyl 2-(4-{4-[3-(aminocarbonyl)phenyl]-3,5-dimethyl-1H-pyrazol-1-yl}phenyl)ethylcarbamate The title compound was prepared according to the procedure described in step 1 of Example 22 from 3-{1-[4-(2-aminoethyl)phenyl]-3,5-dimethyl-1H-pyrazol-4-yl}benzamide (step 5): MS (ESI) m/z 455 [M+H]$^+$, $^1$H-NMR (CDCl$_3$) δ 7.80–7.11 (13H, m), 3.59 (2H, t, J=6.6 Hz), 2.96 (2H, t, J=6.6 Hz), 2.33 (3H, s), 2.31 (3H, s).

Step 7. 3-[3,5-Dimethyl-1-(4-{2-[({[(4-methylphenyl)sulfonyl]amino}carbonyl)amino]ethyl}phenyl)-1H-pyrazol-4-yl]benzamide The title compound was prepared according to the procedure described in step 1 of Example 42 from phenyl 2-(4-{4-[3-(aminocarbonyl)phenyl]-3,5-dimethyl-1H-pyrazol-1-yl}phenyl)ethylcarbamate (step 6) and 2-fluorobenzensulfonamide: MS (ESI) m/z 536 [M+H]$^+$, 534 [M–H]$^-$, $^1$H-NMR (CDCl$_3$) δ 8.03–7.25 (12H, m), 6.51 (1H, br.s) 3.22 (2H, t, J=7.1 Hz), 2.70 (2H, t, J=7.1 Hz), 2.24 (3H, s), 2.22 (3H, s).

Example 61

3-[1-(4-{2-[({[(2,4-Difluorophenyl)sulfonyl]amino}carbonyl)amino]ethyl}phenyl)-3,5-dimethyl-1H-pyrazol-4-yl]benzamide The title compound was prepared according to the procedure described in step 1 of Example 42 from phenyl 2-(4-{4-[3-(aminocarbonyl)phenyl]-3,5-dimethyl-1H-pyrazol-1-yl}phenyl)ethylcarbamate (step 6 of example 72) and 2,4-difluorobenzensulfonamide: MS (ESI) m/z 554 [M+H]$^+$, 552 [M–H]$^-$, $^1$H-NMR (CDCl$_3$) δ 8.00–7.98 (1H, m), 7.83–7.73 (3H, m), 7.56–7.44 (2H, m), 7.22 (4H, s), 7.05–6.94 (1H, m), 6.20 (1H, br.s), 5.66 (1H, br.s), 3.47 (2H, t, J=6.2 Hz), 2.85 (2H, t, J=6.2 Hz), 2.21 (3H, s), 2.20 (3H, s).

Example 62

3-[1-(4-{2-[({[(4-Chlorophenyl)sulfonyl]amino}carbonyl) amino]ethyl}phenyl)-3,5-dimethyl-1H-pyrazol-4-yl]benzamide The title compound was prepared according to the procedure described in step 1 of Example 42 from phenyl 2-(4-{4-[3-(aminocarbonyl)phenyl]-3,5-dimethyl-1H-pyrazol-1-yl}phenyl)ethylcarbamate (step 6 of example 72) and 4-chlorobenzensulfonamide: MS (ESI) m/z 552 [M+H]$^+$, 550 [M–H]$^-$, $^1$H-NMR (CDCl$_3$) δ 7.92–7.80 (4H, m), 7.58–7.47 (4H, m), 7.29–7.18 (4H, m), 6.33 (1H, br.s), 3.47 (2H, t, J=6.1 Hz), 2.86 (2H, t, J=6.1 Hz), 2.23 (6H, s).

Example 63

4-Chloro-N-[({2-[4-(3-ethyl-5-methyl-4-phenyl-1H-pyrazol-1-yl)phenyl]ethyl}amino)carbonyl]benzenesulfonamide Step 1. 2-[4-(3-Ethyl-5-methyl-1H-pyrazol-1-yl)phenyl]ethanol To a stirred solution of propionyl chloride (0.87 mL, 10 mmol) in ether (10 mL) was added a propynylmagnesium bromide 0.5 M solution in tetrahydrofuran (22 mL, 11 mmol) at 0° C. The resulting mixture was stirred at 0° C. for 1 h and then potassium bicarbonate was added. After filtered, ethanol (30 mL) and 2-(4-hydrazinophenyl)ethanol hydrochloride (490 mg, 2.5 mmol) were added. The mixture was heated under reflux overnight. After removal of the solvent, the resulting residue was partitioned between dichloromethane and water. Organic phase was washed with brine and dried (Na$_2$SO$_4$). After removal of the solvent, the crude product was purified by TLC with hexane/ethyl acetate (1:1) to afford 155 mg (27%) of the title compound as yellow oil: MS (EI) m/z 230 [M]+, $^1$H-NMR (CDCl$_3$) δ 7.37–7.30 (4H, m), 6.02 (1H, s), 3.87 (2H, br.s), 2.91 (2H, br.s), 2.67 (2H, q, 6.5 Hz), 2.30 (3H, s), 1.27 (3H, t, 6.5 Hz).

Step 2. 2-[4-(3-Ethyl-4-iodo-5-methyl-1H-pyrazol-1-yl)phenyl]ethanol

The title compound was prepared according to the procedure described in step 2 of Example 11 from 2-[4-(3-ethyl-5-methyl-1H-pyrazol-1-yl)phenyl]ethanol (step 1): MS (EI) m/z 356 [M]$^+$.

Step 3. 2-[4-(3-Ethyl-5-methyl-4-phenyl-1H-pyrazol-1-yl)phenyl]ethanol

The title compound was prepared according to the procedure described in step 1 of Example 12 from 2-[4-(3-ethyl-4-iodo-5-methyl-1H-pyrazol-1-yl)phenyl]ethanol (step 2) and benzeneboronic acid: MS (EI) m/z 306 [M]$^+$.

Step 4. 2-[4-(3-Ethyl-5-methyl-4-phenyl-1H-pyrazol-1-yl)phenyl]ethylmethanesulfonate The title compound was prepared according to the procedure described in step 2 of Example 59 from 2-[4-(3-ethyl-5-methyl-4-phenyl-1H-pyrazol-1-yl)phenyl]ethanol (step 3): MS (ESI) m/z 332 [M+H]$^+$, $^1$H-NMR (CDCl$_3$) δ 7.48–7.26 (9H, m), 4.44 (2H, t, J=6.8 Hz), 3.12 (3H, s), 3.10 (2H, t, J=6.8 Hz), 2.71 (2H, q, J=7.5 Hz), 2.26 (3H, s), 1.18 (3H, t, J=7.5 Hz).

Step 5. 1-[4-(2-Azidoethyl)phenyl]-3-ethyl-5-methyl-4-phenyl-1H-pyrazole The title compound was prepared according to the procedure described in step 3 of Example 59 from 2-[4-(3-ethyl-5-methyl-4-phenyl-1H-pyrazol-1-yl)phenyl]ethyl methanesulfonate (step 4): MS (ESI) m/z 332 [M+H]$^+$.

Step 6. 2-[4-(3-Ethyl-5-methyl-4-phenyl-1H-pyrazol-1-yl)phenyl]ethanamine

The title compound was prepared according to the procedure described in step 3 of Example 14 from 1-[4-(2-azidoethyl)phenyl]-3-ethyl-5-methyl-4-phenyl-1H-pyrazole (step 5): $^1$H-NMR (CDCl$_3$) δ 7.45–7.27 (9H, m), 3.00 (2H, t, J=6.5 Hz), 2.81 (2H, t, J=6.5 Hz), 2.73 (2H, d, J=7.6 Hz), 2.27 (3H, s), 1.19 (3H, t, J=7.6 Hz).

Step 7. 4-Chloro-N-[({2-[4-(3-ethyl-5-methyl-4-phenyl-1H-pyrazol-1-yl)phenyl]ethyl}amino)carbonyl]benzenesulfonamide The title compound was prepared according to the procedure described in step 4 of Example 14 from 2-[4-(3-ethyl-5-methyl-4-phenyl-1H-pyrazol-1-yl)phenyl]ethanamine (step 6) and 4-chlorobenzeneisocyanate: MS (ESI) m/z 523 [M+H]$^+$, 521 [M–H]$^-$, $^1$H-NMR (CDCl$_3$) δ 7.89 (2H, d, J=8.7 Hz), 7.50–7.19 (11H, m), 6.05 (1H, br.s), 3.45 (2H, t, J=6.2 Hz), 2.83 (2H, t, J=6.2 Hz), 2.74 (2H, q, J=7.4 Hz), 1.20 (3H, t, J=7.4 Hz).

Example 64

2,4-Dimethyl-N-{[(2-{4-[5-methyl-4-phenyl-3-(trifluoromethyl)-1H-pyrazol-1-yl]phenyl}ethyl)amino]carbonyl}-1,3-thiazole-5-sulfonamide The title compound was prepared according to the procedure described in step 1 of Example 42 from phenyl 2-{4-[5-methyl-4-phenyl-3-(trifluoromethyl)-1H-pyrazol-1-yl]phenyl}ethylcarbamate (step 7 of Example 52) and 2,4-dimethyl-1,3-thiazole-5-sulfonamide: MS (ESI) m/z 564 [M+H]$^+$, 562 [M–H]$^-$, $^1$H-NMR (CDCl$_3$) δ 7.45–7.32 (9H, m), 6.19 (1H, br.s), 3.49 (2H, t, J=6.6 Hz), 2.89 (2H, t, J=6.6 Hz), 2.67 (3H, s), 2.60 (3H, s), 2.21 (3H, s).

Example 65

N-{[(2-{4-[5-Methyl-4-phenyl-3-(trifluoromethyl)-1H-pyrazol-1-yl]phenyl}ethyl)amino]carbonyl}-1,3-benzenedisulfonamide The title compound was prepared according to the procedure described in step 1 of Example 42 from phenyl 2-{4-[5-methyl-4-phenyl-3-(trifluoromethyl)-1H-pyrazol-1-yl]phenyl}ethylcarbamate (step 7 of Example 52) and 1,3-benzenedisulfonamide: MS (ESI) m/z 608 [M+H]$^+$, 606 [M–H]$^-$, $^1$H-NMR (CDCl$_3$) δ 8.62 (1H, br.s), 8.14 (2H, br.s), 7.70 (1H, br.s), 7.39–7.21 (9H, m), 6.18 (1H, br.s), 3.35 (2H, br.s), 2.76 (2H, br.s), 2.15 (3H, s).

Example 66

5-Chloro-N-{[(2-{4-[5-methyl-4-phenyl-3-(trifluoromethyl)-1H-pyrazol-1-yl]phenyl}ethyl)amino]carbonyl}-2-pyridinesulfonamide The title compound was prepared according to the procedure described in step 1 of Example 42 from phenyl 2-{4-[5-methyl-4-phenyl-3-(trifluoromethyl)-1H-pyrazol-1-yl]phenyl}ethylcarbamate (step 7 of Example 52) and 5-chloro-2-pyridinesulfonamide: MS (ESI) m/z 564 [M+H]$^+$, 562 [M–H]$^-$, $^1$H-NMR (CDCl$_3$) δ 78.54 (1H, s), 7.96–7.90 (2H, m), 7.47–7.19 (7H, m), 6.91–6.79 (2H, m), 6.65 (1H, br.s) 5.98 (1H, br.s), 3.44 (2H, t, J=6.6 Hz), 2.83 (2H, t, J=6.7 Hz), 2.20 (3H, s).

Example 67

3-Hydroxy-N-{[(2-{4-[5-methyl-4-phenyl-3-(trifluoromethyl)-1H-pyrazol-1-yl]phenyl}ethyl)amino]carbonyl}benzenesulfonamide The title compound was prepared according to the procedure described in step 1 of Example 42 from phenyl 2-{4-[5-methyl-4-phenyl-3-(trifluoromethyl)-1H-pyrazol-1-yl]phenyl}ethylcarbamate (step 7 of Example 52) and 3-hydroxybenzenesulfonamide: MS (ESI) m/z 545 [M+H]$^+$, 543 [M–H]$^-$, $^1$H-NMR (CDCl$_3$) δ 7.48–7.01 (13H, m), 6.32 1H, br.s), 3.50 (2H, t, J=6.1 Hz), 2.85 (2H, t, J=6.1 Hz), 2.20 (3H, s).

Example 68

N-[({2-[4-(3,5-Dimethyl-4-phenyl-1H-pyrazol-1-yl)phenyl]ethyl}amino)carbonyl]benzene-1,4-disulfonamide Mono-sodium Salt Step 1. N-[({2-[4-(3,5-dimethyl-4-phenyl-1H-pyrazol-1-yl)phenyl]ethyl}amino) carbonyl]benzene-1,4-disulfonamide The title compound was prepared according to the procedure described in step 2 of Example 22 from phenyl 2-[4-(3,5-dimethyl-4-phenyl-1H-pyrazol-1-yl)phenyl] ethylcarbamate (step 1 of Example 22) and benzene-1,4-disulfonamide: $^1$H-NMR (DMSO-d$_6$) δ 8.10–8.01 (4H, m), 7.63 (2H, s), 7.48–7.27 (9H, m), 6.62–6.59 (1H, m), 3.28–3.21 (2H, m), 2.73 (21H, t, J=7.2 Hz), 2.27 (3H, s), 2.23 (3H, s).

Step 2. N-[({2-[4-(3,5-dimethyl-4-phenyl-1H-pyrazol-1-yl)phenyl]ethyl}amino)carbonyl]benzene-1,4-disulfonamide Mono-sodium Salt The title compound was prepared according to the procedure described in step 4 of Example 8 from N-[({2-[4-(3,5-dimethyl-4-phenyl-1H-pyrazol-1-yl)phenyl]ethyl) amino) carbonyl]benzene-1;4-disulfonamide (step 1): MS (ESI) m/z 554 [M+H]$^+$, 552 [M–H]$^-$.

Example 69

N-[({2-[4-(3,5-Dimethyl-4-phenyl-1H-pyrazol-1-yl)phenyl]ethyl}amino)carbonyl]-1-methyl-1H-tetrazole-5-sulfonamide Mono-sodium Salt Step 1. N-[(2-[4-(3,5-dimethyl-4-phenyl-1H-pyrazol-1-yl)phenyl]ethyl}amino)carbonyl]-1-methyl-1H-tetrazole-5-sulfonamide The title compound was prepared according to the procedure described in step 1 of Example 42 from phenyl 2-[4-(3,5-dimethyl-4-phenyl-1H-pyrazol-1-yl)phenyl] ethylcarbamate (step 1 of Example 22) and 1-methyl-1H-tetrazole-5-sulfonamide: $^1$H-NMR (CDCl$_3$) δ 7.42–7.15 (9H, m), 5.97 (1H, br.s), 4.18 (3H, s), 3.31–3.22 (2H, m), 2.71–2.64 (2H, m), 2.25 (3H, s), 2.18 (3H, s).

Step 2. N-[({2-[4-(3,5-dimethyl-4-phenyl-1H-pyrazol-1-yl)phenyl]ethyl}amino)carbonyl]-1-methyl-1H-tetrazole-5-sulfonamide Mono-sodium Salt The title compound was prepared according to the procedure described in step 4 of Example 8 from N-[({2-[4-(3,5-dimethyl-4-phenyl-1H-pyrazol-1-yl)phenyl]ethyl}amino) carbonyl]-1-methyl-1H-tetrazole-5-sulfonamide (step 1): MS (ESI) m/z 481 [M+H]$^+$, 479 [M–H]$^-$.

Example 70

N-[({2-[4-(3,5-Dimethyl-4-phenyl-1H-pyrazol-1-yl) phenyl]ethyl}amino)carbonyl]pyridine-3-sulfonamide Mono-sodium Salt Step 1. N-[({2-[4-(3,5-dimethyl-4-phenyl-1H-pyrazol-1-yl) phenyl]ethyl}amino)carbonyl]pyridine-3-sulfonamide The title compound was prepared according to the procedure described in step 2 of Example 22 from phenyl 2-[4-(3,5-dimethyl-4-phenyl-1H-pyrazol-1-yl)phenyl] ethylcarbamate (step 1 of Example 22) and pyridine-3-sulfonamide: $^1$H-NMR [CDCl$_3$/CD$_3$OD(10:1)] δ 9.10 (1H, d, J=2.2 Hz), 8.71–8.70 (1H, m), 8.24 (1H, d, J=8.3 Hz), 7.45–7.16 (1H, m), 6.26 (1H, br.s), 3.42–3.33 (2H, m), 2.80–2.73 (2H, m), 2.29 (3H, s), 2.20 (3H, s).

Step 2. N-[({2-[4-(3,5-dimethyl-4-phenyl-1H-pyrazol-1-yl) phenyl]ethyl}amino)carbonyl]pyridine-3-sulfonamide Mono-sodium Salt The title compound was prepared according to the procedure described in step 4 of Example 8 from N-[({2-[4-(3,5-dimethyl-4-phenyl-1H-pyrazol-1-yl)phenyl]ethyl}amino) carbonyl]pyridine-3-sulfonamide (step 1): MS (ESI) m/z 4767 [M+H]$^+$, 474 [M–H]$^-$.

Example 71

N-[({2-[4-(3,5-Dimethyl-4-phenyl-1H-pyrazol-1-yl) phenyl]ethyl}amino)carbonyl]-4,5-dimethyl-1,3-thiazole-2-sulfonamide Mono-sodium Salt Step 1. N-[({2-[4-(3,5-dimethyl-4-phenyl-1H-pyrazol-1-yl) phenyl]ethyl}amino)carbonyl]-4,5-dimethyl-1,3-thiazole-2-sulfonamide The title compound was prepared according to the procedure described in step 1 of Example 42 from phenyl 2-[4-(3,5-dimethyl-4-phenyl-1H-pyrazol-1-yl)phenyl] ethylcarbamate (step 1 of Example 22) and 4,5-dimethyl-1,3-thiazole-2-sulfonamide: $^1$H-NMR (CDCl$_3$) δ 7.45–7.24 (9H, m), 6.47 (1H, br.s), 3.50–3.42 (2H, m), 2.88–2.82 (2H, m), 2.41 (3H, s), 2.35 (3H, s), 2.31 (3H, s), 2.24 (3H, s).

Step 2. N-[({2-[4-(3,5-dimethyl-4-phenyl-1H-pyrazol-1-yl) phenyl]ethyl}amino)carbonyl]-4,5-dimethyl-1,3-thiazole-2-sulfonamide mono-sodium salt The title compound was prepared according to the procedure described in step 4 of Example 8 from N-[({2-[4-(3,5-dimethyl-4-phenyl-1H-pyrazol-1-yl)phenyl]ethyl}amino) carbonyl]-4,5-dimethyl-1,3-thiazole-2-sulfonamide (step 1): MS (ESI) m/z 510 [M+H]$^+$, 508 [M–H]$^-$.

Example 72

[4-({[({2-[4-(3,5-Dimethyl-4-phenyl-1H-pyrazol-1-yl)phenyl]ethyl}amino)carbonyl]amino}sulfonyl) benzyl]acetamide Mono-sodium Salt Step 1. N-[4-({[({2-[4-(3,5-dimethyl-4-phenyl-1H-pyrazol-1-yl)phenyl]ethyl}amino)carbonyl]amino}sulfonyl)benzyl] acetamide The title compound was prepared according to the procedure described in step 1 of Example 42 from phenyl 2-[4-(3,5-dimethyl-4-phenyl-1H-pyrazol-1-yl)phenyl] ethylcarbamate (step 1 of Example 22) and N-[4-(aminosulfonyl)benzyl]acetamide: $^1$H-NMR [CDCl$_3$/CD$_3$OD(4:1)] δ 7.90–7.87 (2H, m), 7.48–7.26 (11H, m), 4.44 (2H, s), 3.45–3.41 (2H, m), 2.87–2.82 (2H, m), 2.32 (3H, s), 2.27 (3H, s), 2.03 (3H, s).

Step 2. N-[4-({[({2-[4-(3,5-dimethyl-4-phenyl-1H-pyrazol-1-yl)phenyl]ethyl}amino)carbonyl]amino}sulfonyl)benzyl] acetamide mono-sodium salt The title compound was prepared according to the procedure described in step 4 of Example 8 from N-[4-({[({2-[4-(3,5-dimethyl-4-phenyl-1H-pyrazol-1-yl)phenyl] ethyl}amino)carbonyl]amino}sulfonyl)benzyl]acetamide (step 1): MS (ESI) m/z 546 [M+H]$^+$, 544 [M–H]$^-$.

Example 73

N-[({2-[4-(3,5-Dimethyl-4-phenyl-1H-pyrazol-1-yl) phenyl]ethyl}amino)carbonyl]-4-(Methylsulfonyl) benzenesulfonamide Mono-p-toluenesulfonate Salt Step 1. N-[({2-[4-(3,5-dimethyl-4-phenyl-1H-pyrazol-1-yl) phenyl]ethyl}amino) carbonyl]-4-(methylsulfonyl) benzenesulfonamide The title compound was prepared according to the procedure described in step 2 of Example 22 from phenyl 2-[4-(3,5-dimethyl-4-phenyl-1H-pyrazol-1-yl)phenyl] ethylcarbamate (step 1 of Example 22) and 4-(methylsulfonyl)benzenesulfonamide: $^1$H-NMR (CDCl$_3$) δ 8.16–8.08 (4H, m), 7.47–7.20 (9H, m), 6.04 (1H, br.s), 3.46–3.41 (2H, m), 3.10 (3H, s), 2.87–2.82 (2H, m), 2.33 (3H, s), 2.22 (3H, s).

Step 2. N-[({2-[4-(3,5-dimethyl-4-phenyl-1H-pyrazol-1-yl) phenyl]ethyl}amino)carbonyl]-4-(methylsulfonyl) benzenesulfonamide Mono-p-toluenesulfonate Salt The title compound was prepared according to the procedure described in step 6 of Example 15 from N-[({2-[4-(3,5-dimethyl-4-phenyl-1H-pyrazol-1-yl)phenyl] ethyl}amino)carbonyl]-4-(methylsulfonyl) benzenesulfonamide (step 1): MS (ESI) m/z 553 [M+H]$^+$, 551 [M–H]$^-$.

Example 74

N-[({2-[4-(3,5-Dimethyl-4-phenyl-1H-pyrazol-1-yl) phenyl]ethyl}amino)carbonyl]-4,6-dimethylpyrimidine-2-sulfonamide Mono-sodium Salt Step 1. N-[({2-[4-(3,5-dimethyl-4-phenyl-1H-pyrazol-1-yl) phenyl]ethyl}amino)carbonyl]-4,6-dimethylpyrimidine-2-sulfonamide The title compound was prepared according to the procedure described in step 1 of Example 42 from phenyl 2-[4-(3,5-dimethyl-4-phenyl-1H-pyrazol-1-yl)phenyl] ethylcarbamate (step 1 of Example 22) and 4,6-dimethylpyrimidine-2-sulfonamide: $^1$H-NMR (CDCl$_3$) δ 7.46–7.23 (10H, m), 6.82 (1H, br.s), 3.54–3.47 (2H, m), 2.89–2.84 (2H, m), 2.58 (6H, s), 2.33 (3H, s), 2.27 (3H, s).

Step 2. N-[({2-[4-(3,5-dimethyl-4-phenyl-1H-pyrazol-1-yl) phenyl]ethyl}amino)carbonyl]-4,6-dimethylpyrimidine-2-sulfonamide mono-sodium salt The title compound was prepared according to the procedure described in step 4 of Example 8 from N-[({2-[4-(3,5-dimethyl-4-phenyl-1H-pyrazol-1-yl)phenyl]ethyl}amino) carbonyl]-4,6-dimethylpyrimidine-2-sulfonamide (step 1): MS (ESI) m/z 505 [M+H]$^+$, 503 [M–H]$^-$.

Example 75

N-[({2-[4-(3,5-Dimethyl-4-phenyl-1H-pyrazol-1-yl) phenyl]ethyl}amino)carbonyl]-1,2-dimethyl-1H-imidazole-4-sulfonamide Mono-sodium Salt Step 1. N-[({2-[4-(3,5-dimethyl-4-phenyl-1H-pyrazol-1-yl) phenyl]ethyl}amino)carbonyl]-1,2-dimethyl-1H-imidazole-4-sulfonamide The title compound was prepared according to the procedure described in step 2 of Example 22 from phenyl 2-[4-(3,5-dimethyl-4-phenyl-1H-pyrazol-1-yl)phenyl] ethylcarbamate (step 1 of Example 22) and 1,2-dimethyl-1H-imidazole-4-sulfonamide: $^1$H-NMR (CDCl$_3$) δ

7.50–7.27 (10H, m), 3.62 (3H, s), 3.46–3.41 (2H, m), 2.87–2.82 (2H, m), 2.37 (3H, s), 2.32 (3H, s), 2.27 (3H, s).

Step 2. N-[({2-[4-(3,5-dimethyl-4-phenyl-1H-pyrazol-1-yl)phenyl]ethyl}amino)carbonyl]-1,2-dimethyl-1H-imidazole-4-sulfonamide Mono-sodium Salt The title compound was prepared according to the procedure described in step 4 of Example 8 from N-[({2-[4-(3,5-dimethyl-4-phenyl-1H-pyrazol-1-yl)phenyl]ethyl}amino)carbonyl]-1,2-dimethyl-1H-imidazole-4-sulfonamide (step 1): MS (ESI) m/z 493 [M+H]$^+$, 491 [M–H]$^-$.

Example 76

4-[2-(Dimethylamino)ethoxy]-N-[({2-[4-(3,5-dimethyl-4-phenyl-1H-pyrazol-1-yl)phenyl]ethyl}amino)carbonyl]benzenesulfonamide Mono-sodium Salt Step 1. 4-[2-(dimethylamino)ethoxy]-N-[({2-[4-(3,5-dimethyl-4-phenyl-1H-pyrazol-1-yl)phenyl]ethyl}amino)carbonyl]benzenesulfonamide The title compound was prepared according to the procedure described in step 1 of Example 42 from phenyl 2-[4-(3,5-dimethyl-4-phenyl-1H-pyrazol-1-yl)phenyl]ethylcarbamate (step 1 of Example 22) and 4-[2-(dimethylamino)ethoxy]benzenesulfonamide: $^1$H-NMR [CDCl$_3$/CD$_3$OD(4:1)] δ δ 7.87–7.84 (2H, m), 7.48–7.26 (9H, m), 7.01–6.98 (2H, m), 4.19–4.15 (2H, m), 3.46–3.41 (2H, m), 2.92–2.82 (4H, m), 2.45 (6H, s), 2.32 (3H, s), 2.27 (3H, s).

Step 2. 4-[2-(dimethylamino)ethoxy]-N-[({2-[4-(3,5-dimethyl-4-phenyl-1H-pyrazol-1-yl)phenyl]ethyl}amino)carbonyl]benzenesulfonamide Mono-sodium Salt The title compound was prepared according to the procedure described in step 4 of Example 8 from 4-[2-(dimethylamino)ethoxy]-N-[({2-[4-(3,5-dimethyl-4-phenyl-1H-pyrazol-1-yl)phenyl]ethyl}amino)carbonyl]benzenesulfonamide (step 1): MS (ESI) m/z 562 [M+H]$^+$, 560 [M–H]$^-$.

Example 77

2-[4-(4-Chloro-3,5-dimethyl-1H-pyrazol-1-yl)phenyl]ethyl (4-methylphenyl)sulfonylcarbamate Step 1. 2-[4-(4-chloro-3,5-dimethyl-1H-pyrazol-1-yl)phenyl]ethanol The title compound was prepared according to the procedure described in step 1 of Example 1 from 2-(4-hydrazinophenyl)ethanol hydrochloride and 3-chloropentane-2,4-dione: MS (ESI) m/z 251 [M+H]$^+$, $^1$H-NMR (CDCl$_3$) δ 7.32–7.25 (4H, m), 3.76 (2H, t, J=6.7 Hz), 2.85 (2H, t, J=6.7 Hz), 2.32 (1H, br.s), 2.28 (3H, s), 2.27 (3H, s).

Step 2. 2-[4-(4-chloro-3,5-dimethyl-1H-pyrazol-1-yl)phenyl]ethyl (4-methylphenyl)sulfonylcarbamate The title compound was prepared according to the procedure described in step 2 of Example 1 from 2-[4-(4-chloro-3,5-dimethyl-1H-pyrazol-1-yl)phenyl]ethanol (step 1): MS (ESI) m/z 448 [M+H]$^+$, $^1$H-NMR (CDCl$_3$) δ 7.88–7.85 (2H, m), 7.32–7.17 (6H, m), 4.26 (2H, t, J=6.8 Hz), 2.90 (2H, t, J=6.8 Hz), 2.42 (3H, s), 2.28 (3H, s), 2.26 (3H, s).

Example 78

N-{[(2-{4-[5-Phenyl-3-(trifluoromethyl)-1H-pyrazol-1-yl]phenyl}ethyl)amino]carbonyl}pyridine-3-sulfonamide Mono-sodium Salt Step 1. 2-{4-[5-phenyl-3-(trifluoromethyl)-1H-pyrazol-1-yl]phenyl}ethylmethanesulfonate The title compound was prepared according to the procedure described in step 2 of Example 59 from 2-{4-[5-phenyl-3-(trifluoromethyl)-1H-pyrazol-1-yl]phenyl}ethanol (step 1 of Example 1): MS (ESI) m/z 411 [M+H]$^+$.

Step 2. 1-[4-(2-azidoethyl)phenyl]-5-phenyl-3-(trifluoromethyl)-1H-pyrazole

The title compound was prepared according to the procedure described in step 3 of Example 59 from 2-{4-[5-phenyl-3-(trifluoromethyl)-1H-pyrazol-1-yl]phenyl}ethyl methanesulfonate (step 1): MS (ESI) m/z 358 [M+H]$^+$, $^1$H-NMR (CDCl$_3$) δ 7.37–7.20 (9H, m), 6.75 (1H, s), 3.50 (2H, t, J=7.1 Hz), 2.91 (2H, t, J=7.1 Hz).

Step 3. 2-{4-[5-phenyl-3-(trifluoromethyl)-1H-pyrazol-1-yl]phenyl}ethanamine

The title compound was prepared according to the procedure described in step 3 of Example 14 from 1-[4-(2-azidoethyl)phenyl]-5-phenyl-3-(trifluoromethyl)-1H-pyrazole (step 2): MS (ESI) m/z 332 [M+H]$^+$, 373 [M+H+CH$_3$CN]$^+$.

Step 4. phenyl 2-{4-[5-phenyl-3-(trifluoromethyl)-1H-pyrazol-1-yl]phenyl}Ethylcarbamate The title compound was prepared according to the procedure described in step 1 of Example 22 from 2-{4-[5-phenyl-3-(trifluoromethyl)-1H-pyrazol-1-yl]phenyl}ethanamine (step 3): MS (ESI) m/z 452 [M+H]$^+$, $^1$H-NMR (CDCl$_3$) δ 7.38–7.08 (14H, m), 6.75 (1H, s), 5.00 (1H, br.s), 3.56–3.49 (2H, m), 2.92 (2H, t, J=7.0 Hz).

Step 5. N-{[(2-{4-[5-phenyl-3-(trifluoromethyl)-1H-pyrazol-1-yl]phenyl}ethyl)amino]carbonyl}pyridine-3-sulfonamide The title compound was prepared according to the procedure described in step 1 of Example 0.42 from phenyl 2-{4-[5-phenyl-3-(trifluoromethyl)-1H-pyrazol-1-yl]phenyl}ethylcarbamate (step 4) and pyridine-3-sulfonamide: $^1$H-NMR (CDCl$_3$) δ 9.04 (1H, d, J=2.0 Hz), 8.78 (1H, d, J=3.7 Hz), 8.08–8.04 (1H, m), 7.48–7.44 (1H, m), 7.34–7.10 (9H, m), 6.76 (1H, s), 6.28 (1H, br.s), 3.48–3.42 (2H, m), 2.83–2.78 (2H, m).

Step 6. N-{[(2-{4-[5-phenyl-3-(trifluoromethyl)-1H-pyrazol-1-yl]phenyl}ethyl)amino]carbonyl}pyridine-3-sulfonamide Mono-sodium Salt The title compound was prepared according to the procedure described in step 4 of Example 8 from N-{[(2-{4-[5-phenyl-3-(trifluoromethyl)-1H-pyrazol-1-yl]phenyl}ethyl)amino]carbonyl}pyridine-3-sulfonamide (step 5): MS (ESI) m/z 516 [M+H]$^+$, 514 [M–H]$^-$.

Example 79

N-{[(2-{4-[5-Phenyl-3-(trifluoromethyl)-1H-pyrazol-1-yl]phenyl}ethyl)amino]carbonyl}pyridine-4-sulfonamide Mono-sodium Salt Step 1. N-{[(2-{4-[5-Phenyl-3-(trifluoromethyl)-1H-pyrazol-1-yl]phenyl}ethyl)amino]carbonyl}pyridine-4-sulfonamide The title compound was prepared according to the procedure described in step 1 of Example 42 from phenyl 2-{4-[5-phenyl-3-(trifluoromethyl)-1H-pyrazol-1-yl]phenyl}ethylcarbamate (step 4 of Example 78) and pyridine-4-sulfonamide: $^1$H-NMR (CDCl$_3$) δ 8.79–8.73 (2H, m), 7.64–7.62 (2H, m), 7.31–7.07 (9H, m), 6.76 (1H, s), 6.24 (1H, br.s), 3.46–3.37 (2H, m), 2.81–2.72 (2H, m).

Step 2. N-{[(2-{4-[5-phenyl-3-(trifluoromethyl)-1H-pyrazol-1-yl]phenyl}ethyl)amino]carbonyl}pyridine-4-sulfonamide mono-sodium salt The title compound was prepared according to the procedure described in step 4 of Example 8 from N-{[(2-{4-[5-phenyl-3-(trifluoromethyl)-1H-pyrazol-1-yl]phenyl}ethyl)amino]carbonyl}pyridine-4-sulfonamide (step 1): MS (ESI) m/z 516 [M+H]$^+$, 514 [M–H]$^-$.

Example 80

N-{[(2-{4-[5-Amino-4-phenyl-3-(trifluoromethyl)-1H-pyrazol-1-yl]phenyl}ethyl)amino]carbonyl}-2,4-difluorobenzenesulfonamide Mono-sodium Salt

Step 1. 2-{4-[5-amino-4-phenyl-3-(trifluoromethyl)-1H-pyrazol-1-yl]phenyl}ethyl methanesulfonate The title compound was prepared according to the procedure described in step 2 of Example 59 from 2-{4-[5-amino-4-phenyl-3-(trifluoromethyl)-1H-pyrazol-1-yl]phenyl}ethanol (step 1 of Example 7): MS (ESI) m/z 426 [M+H]$^+$, 424 [M−H]$^-$, $^1$H-NMR (CDCl$_3$) δ 7.59–7.34 (9H, m), 4.43 (2H, t, J=6.6 Hz), 3.95 (2H, br.s), 3.11 (2H, t, J=6.6 Hz), 2.92 (3H, s).

Step 2. 1-[4-(2-azidoethyl)phenyl]-4-phenyl-3-(trifluoromethyl)-1H-pyrazol-5-amine The title compound was prepared according to the procedure described in step 3 of Example 59 from 2-{4-[5-amino-4-phenyl-3-(trifluoromethyl)-1H-pyrazol-1-yl]phenyl}ethyl methanesulfonate (step 1): MS (ESI) m/z 373 [M+H]$^+$, 371 [M−H]$^-$, $^1$H-NMR (CDCl$_3$) δ 7.61–7.57 (2H, m), 7.49–7.34 (7H, m), 3.92 (2H, br.s), 3.56 (21H, t, J=7.0 Hz), 2.97 (2H, t, J=7.0 Hz).

Step 3. 1-[4-(2-aminoethyl)phenyl]-4-phenyl-3-(trifluoromethyl)-1H-pyrazol-5-amine The title compound was prepared according to the procedure described in step 3 of Example 14 from 1-[4-(2-azidoethyl)phenyl]-4-phenyl-3-(trifluoromethyl)-1H-pyrazol-5-amine (step 2): MS (ESI) m/z 347 [M+H]$^+$, 345 [M−H]$^-$.

Step 4. phenyl 2-{4-[5-amino-4-phenyl-3-(trifluoromethyl)-1H-pyrazol-1-yl]phenyl}ethylcarbamate The title compound was prepared according to the procedure described in step 1 of Example 22 from 1-[4-(2-aminoethyl)phenyl]-4-phenyl-3-(trifluoromethyl)-1H-pyrazol-5-amine (step 3): MS (ESI) m/z 467 [M+H]$^+$, $^1$H-NMR (CDCl$_3$) δ 7.62–7.58 (2H, m), 7.49–7.09 (12H, m), 5.05 (1H, br.s), 3.91 (2H, br.s), 3.60–3.53 (2H, m), 3.00–2.95 (2H, m).

Step 5. N-{[(2-{4-[5-amino-4-phenyl-3-(trifluoromethyl)-1H-pyrazol-1-yl]phenyl}ethyl)amino]carbonyl 1-2,4-difluorobenzenesulfonamide The title compound was prepared according to the procedure described in step 1 of Example 42 from phenyl 2-{4-[5-amino-4-phenyl-3-(trifluoromethyl)-1H-pyrazol-1-yl]phenyl}ethylcarbamate (step 4) and 2,4-difluorobenzenesulfonamide: $^1$H-NMR (CDCl$_3$) δ 7.93–7.85 (1H, m), 7.49–7.28 (9H, m), 7.06–6.93 (2H, m), 6.17–6.13 (1H, br.s), 3.98 (2H, br.s), 3.51–3.45 (2H, m), 2.88–2.83 (2H, m).

Step 6. N-{[(2-{4-[5-amino-4-phenyl-3-(trifluoromethyl)-1H-pyrazol-1-yl]phenyl}ethyl)amino]carbonyl}-2,4-difluorobenzenesulfonamide mono-sodium salt The title compound was prepared according to the procedure described in step 4 of Example 8 from N-{[(2-{4-[5-amino-4-phenyl-3-(trifluoromethyl)-1H-pyrazol-1-yl]phenyl}ethyl)amino]carbonyl}-2,4-difluorobenzenesulfonamide (step 5): MS (ESI) m/z 566 [M+H]$^+$, 564 [M−H]$^-$.

Example 81

N-{[(2-{4-[5-Amino-4-phenyl-3-(trifluoromethyl)-1H-pyrazol-1-yl] phenyl}ethyl)amino]Carbonyl}-4-chlorobenzenesulfonamide Mono-sodium Salt

Step 1. N-{[(2-{4-[5-amino-4-phenyl-3-(trifluoromethyl)-1H-pyrazol-1-yl]phenyl}ethyl)amino]carbonyl}-4-chlorobenzenesulfonamide The title compound was prepared according to the procedure described in step 1 of Example 42 from phenyl 2-{4-[5-amino-4-phenyl-3-(trifluoromethyl)-1H-pyrazol-1-yl]phenyl}ethylcarbamate (step 4 of Example 80) and 4-chlorobenzenesulfonamide: $^1$H-NMR (CDCl$_3$) δ 7.85–7.80 (2H, m), 7.51–7.27 (11H, m), 6.08–6.03 (1H, m), 3.99 (2H, br.s), 3.50–3.44 (2H, m), 2.88–2.84 (2H, m).

Step 2. N-{[(2-{4-[5-amino-4-phenyl-3-(trifluoromethyl)-1H-pyrazol-1-yl]phenyl}ethyl)amino]carbonyl)-4-chlorobenzenesulfonamide Mono-sodium Salt The title compound was prepared according to the procedure described in step 4 of Example 8 from N-{[(2-{4-[5-amino-4-phenyl-3-(trifluoromethyl)-1H-pyrazol-1-yl]phenyl}ethyl)amino]carbonyl}-4-chlorobenzenesulfonamide (step 1): MS (ESI) m/z 564 [M+H]$^+$, 562 [M−H]$^-$.

Example 82

2-{4-[5-Pyridin-4-yl-3-(trifluoromethyl)-1H-pyrazol-1-yl]phenyl}ethyl (4-methylphenyl) sulfonylcarbamate

Step 1. 2-[4-[5-pyridin-4-yl-3-(trifluoromethyl)-1H-pyrazol-1-yl]phenyl}ethanol

The title compound was prepared according to the procedure described in step 1 of Example 1 from 2-(4-hydrazinophenyl)ethanol hydrochloride and 4,4,4-trifluoro-1-pyridin-4-ylbutane-1,3-dione: MS (ESI) m/z 334 [M+H]$^+$, $^1$H-NMR (CDCl$_3$) δ 8.60–8.58 (2H, m), 7.28–7.24 (4H, m), 7.14–7.12 (2H, m), 6.88 (1H, s), 3.90–3.86 (2H, m), 2.92 (2H, t, J=6.6 Hz), 1.52 (1H, br.s).

Step 2. 2-{4-[5-pyridin-4-yl-3-(trifluoromethyl)-1H-pyrazol-1-yl]phenyl}ethyl (4-methylphenyl) sulfonylcarbamate The title compound was prepared according to the procedure described in step 2 of Example 1 from 2-{4-[5-pyridin-4-yl-3-(trifluoromethyl)-1H-pyrazol-1-yl]phenyl}ethanol (step 1): MS (ESI) m/z 531 [M+H]$^+$, 529 [M−H]$^-$, $^1$H-NMR (CDCl$_3$) δ 8.59–8.57 (2H, m), 7.93–7.90 (2H, m), 7.75–7.72 (2H, m), 7.41–7.17 (7H, m), 4.37 (2H, t, J=6.6 Hz), 2.99 (2H, t, J=6.6 Hz), 2.43 (3H, s).

Example 83

4-Chloro-N-[({2-[6-(3,5-dimethyl-4-phenyl-1H-pyrazol-1-yl)pyridin-3-yl]ethyl}amino)carbonyl]benzenesulfonamide mono-sodium salt

Step 1. ethyl 6-(3,5-dimethyl-4-phenyl-1H-pyrazol-1-yl)nicotinate

A mixture of 3,5-dimethyl-4-phenyl-1H-pyrazole (2.50 g, 14.5 mmol), ethyl 6-chloronicotinate (5.39 g, 29.0 mmol), potassium carbonate (8.02 g, 58.1 mmol) and dimethyl sulfoxide (100 mL) was stirred at 160° C. for 16 h. After cooling to room temperature, the mixture was diluted with ethyl acetate and toluene (2:1) and washed with water. The organic fraction was dried over MgSO$_4$ and concentrated under reduced pressure. The residue was purified by silica-gel column chromatography eluting with hexane/ethyl acetate (8:1) to afford 2.43 g (52%) of the title compound: MS (ESI) m/z 322 [M+H]$^+$, $^1$H-NMR (CDCl$_3$) δ 9.06–9.05 (1H, m), 8.39–8.36 (1H, m), 8.04–8.01 (1H, m), 7.48–7.29 (5H, m), 4.42 (2H, q, J=7.2 Hz), 2.67 (3H, s), 2.32 (3H, s), 1.43 (3H, t, J=7.2 Hz).

Step 2. [6-(3,5-dimethyl-4-phenyl-1H-pyrazol-1-yl)pyridin-3-yl]methanol

To a stirred solution of lithium aluminum hydride (0.72 g, 15.1 mmol) and tetrahydrofuran (20 mL) was added slowly a solution of ethyl 6-(3,5-dimethyl-4-phenyl-1H-pyrazol-1- yl)nicotinate (step 1, 2.43 g, 7.56 mmol) and tetrahydrofuran (40 mL) at 0° C. After 2 h, sodium sulfate decahydrate and potassium fluoride were added slowly to the mixture at 0° C. The mixture was filtered through a bed of celite, and the filtrate was concentrated in vacuo. The residue was purified by silica-gel column chromatography eluting with hexane/ethyl acetate (1:1) to give 1.51 g (72%) of title compound as white solids: MS (ESI) m/z 280 [M+H]$^+$, $^1$H-NMR (CDCl$_3$) δ 8.42–8.41 (1H, m), 7.83–7.82 (2H, m), 7.47–7.28 (5H, m), 4.75 (2H, s), 2.58 (3H, s), 2.33 (3H, s), 2.30 (3H, s).

Step 3. [6-(3,5-dimethyl-4-phenyl-1H-pyrazol-1-yl)pyridin-3-yl]acetonitrile

To a stirred solution of [6-(3,5-dimethyl-4-phenyl-1H-pyrazol-1-yl)pyridin-3-yl]methanol (step 2, 1.51 g, 5.41 mmol), triethylamine (0.90 mL, 6.49 mmol), and dichloromethane (30 mL) was added methanesulfonyl chloride (0.46 mL, 5.95 mmol) at 0° C. The mixture was warmed to room temperature and stirred for 1 h. The mixture was diluted with dichloromethane and washed with water. The organic layer was dried over MgSO$_4$, and concentrated under reduced pressure. The residue was treated with potassium cyanide (1.76 g, 27.0 mmol), N,N-dimethylformamide (25 mL) and water (5 mL) at 65° C. for 16 h. After cooling to room temperature, the mixture was diluted with ethyl acetate and toluene (2:1) and washed with water. The organic fraction was dried over MgSO$_4$ and concentrated under reduced pressure. The residue was purified by silica-gel column chromatography eluting with hexane/ethyl acetate (6:1) to afford 0.63 g (41%) of the title compound: MS (ESI) m/z 289 [M+H]$^+$, 287 [M–H]$^-$, $^1$H-NMR (CDCl$_3$) δ 8.39–8.38 (1H, m), 7.94 (1H, d, J=8.6 Hz), 7.79–7.76 (1H, m), 7.46–7.29 (5H, m), 3.77 (2H, s), 2.61 (3H, s), 2.31 (3H, s).

Step 4. 2-[6-(3,5-dimethyl-4-phenyl-1H-pyrazol-1-yl)pyridin-3-yl]ethanamine

A mixture of [6-(3,5-dimethyl-4-phenyl-1H-pyrazol-1-yl)pyridin-3-yl]acetonitrile (step 3, 633 mg, 2.20 mmol), Raney Ni (W2, 0.5 g), hydrazine monohydrate (1.1 mL, 22.0 mmol), and ethanol (20 mL) was stirred at 60° C. for 6 h. After cooling to room temperature, the mixture was filtered through a bed of celite. The filtrate was evaporated to afford 642 mg (quant.) of title compound: MS (ESI) m/z 293 [M+H]$^+$.

Step 5. phenyl 2-[6-(3,5-dimethyl-4-phenyl-1H-pyrazol-1-yl)pyridin-3-yl]ethylcarbamate The title compound was prepared according to the procedure described in step 1 of Example 22 from phenyl 2-[6-(3,5-dimethyl-4-phenyl-1H-pyrazol-1-yl)pyridin-3-yl]ethanamine (step 4): MS (ESI) m/z 413 [M+H]$^+$, $^1$H-NMR (CDCl$_3$) δ 8.34 (1H, d, J=2.0 Hz), 7.84 (1H, d, J=8.2 Hz), 7.70 (1H, dd, J=8.2 and 2.0 Hz), 7.47–7.10 (10H, m), 5.10 (1H, br.s), 3.60–3.52 (2H, m), 2.97–2.92 (2H, m), 2.60 (3H, s), 2.32 (3H, s).

Step 6. 4-chloro-N-[({2-[6-(3,5-dimethyl-4-phenyl-1H-pyrazol-1-yl)pyridin-3-yl]ethyl}amino)carbonyl]benzenesulfonamide The title compound was prepared according to the procedure described in step 1 of Example 42 from phenyl 2-[6-(3,5-dimethyl-4-phenyl-1H-pyrazol-1-yl)pyridin-3-yl]ethylcarbamate (step 5) and 4-chlorobenzenesulfonamide: $^1$H-NMR (CDCl$_3$) δ 8.20 (1H, br.s), 7.83–7.77 (22H, m), 7.63–7.26 (9H, m), 6.68 (1H, br.s), 3.52–3.45 (2H, m), 2.84–2.79 (2H, m), 2.48 (3H, s), 2.67 (3H, s).

Step 7. 4-chloro-N-[({2-[6-(3,5-dimethyl-4-phenyl-1H-pyrazol-1-yl)pyridin-3-yl]ethyl}amino)carbonyl]benzenesulfonamide mono-sodium salt The title compound was prepared according to the procedure described in step 4 of Example 8 from 4-chloro-N-[({2-[6-(3,5-dimethyl-4-phenyl-1H-pyrazol-1-yl)pyridin-3-yl]ethyl}amino)carbonyl]benzenesulfonamide (step 6): MS (ESI) m/z 510 [M+H]$^+$, 508 [M–H]$^-$.

Example 84

N-[({2-[6-(3,5-Dimethyl-4-phenyl-1H-pyrazol-1-yl)pyridin-3-yl]ethyl}amino)carbonyl]benzene-1,3-disulfonamide Mono-sodium Salt Step 1. N-[({2-[6-(3,5-dimethyl-4-phenyl-1H-pyrazol-1-yl)pyridin-3-yl]ethyl}amino)carbonyl]benzene-1,3-disulfonamide The title compound was prepared according to the procedure described in step 1 of Example 42 from phenyl 2-[6-(3,5-dimethyl-4-phenyl-1H-pyrazol-1-yl)pyridin-3-yl]ethylcarbamate (step 5 of Example 83) and 1,3-benzenedisulfonamide: $^1$H-NMR (CDCl$_3$) δ 8.48–8.43 (1H, m), 8.10–7.76 (3H, m), 7.48–7.20 (8H, m), 6.61 (1H, br.s), 3.43–3.24 (2H, m), 2.73–2.59 (2H, m), 2.37 (3H, s), 2.25 (3H, s).

Step 2. N-[({2-[6-(3,5-dimethyl-4-phenyl-1H-pyrazol-1-yl)pyridin-3-yl]ethyl}amino)carbonyl]benzene-1,3-disulfonamide mono-sodium salt The title compound was prepared according to the procedure described in step 4 of Example 8 from N-[({2-[6-(3,5-dimethyl-4-phenyl-1H-pyrazol-1-yl)pyridin-3-yl]ethyl}amino)carbonyl]benzene-1,3-disulfonamide (step 1): MS (ESI) m/z 555 [M+H]$^+$, 553 [M–H]$^-$.

Example 85

2-[4-(3,5-Diphenyl-1H-pyrazol-1-yl)phenyl]ethyl (4-methylphenyl)sulfonylcarbamate Step 1. 2-[4-(3,5-Diphenyl-1H-pyrazol-1-yl)phenyl]ethanol The title compound was prepared according to the procedure described in step 1 of Example 1 from 1,3-diphenylpropane-1,3-dione and 2-(4-hydrazinophenyl)ethanol hydrochloride: MS (ESI) m/z 341 [M+H]$^+$, $^1$H-NMR (CDCl$_3$) δ 7.93–7.91 (2H, m), 7.46–7.20 (12H, m), 6.82 (1H, s), 3.87 (2H, br), 2.89 (2H, t, J=6.6 Hz).

Step 2. 2-[4-(3,5-Diphenyl-1H-pyrazol-1-yl)phenyl]ethyl (4-methylphenyl)sulfonylcarbamate The title compound was prepared according to the procedure described in step 2 of Example 1 from 2-[4-(3,5-diphenyl-1H-pyrazol-1-yl)phenyl]ethanol (step 1): MS (ESI) m/z 538 [M+H]$^+$, 536 [M–H]$^-$, $^1$H-NMR (CDCl$_3$) δ 7.92–7.80 (5H, m), 7.45–7.25 (11H, m), 7.10 (2H, d, J=6.4 Hz), 4.27 (2H, t, J=6.8 Hz), 2.89 (2H, t, J=6.8 Hz), 2.41 (3H, s).

Example 86

2-[4-(3-Methyl-5-phenyl-1H-pyrazol-1-yl)phenyl]ethyl (4-methylphenyl)sulfonylcarbamate The title compound was prepared according to the procedure described in step 2 of Example 1 from 2-[4-(3-methyl-5-phenyl-1H-pyrazol-1-yl)phenyl]ethanol (step 1 of Example 3): MS (ESI) m/z 476 [M+H]$^+$, 474 [M–H]$^-$, $^1$H-NMR (CDCl$_3$) δ 7.87 (2H, d, J=7.3 Hz), 7.29–7.10 (9H, m), 7.00 (2H, d, J=7.3 Hz), 6.29 (1H, s), 4.20 (2H, t, J=6.8 Hz), 2.82 (2H, t, J=6.8 Hz), 2.40 (3H, s), 2.37 (3H, s).

Example 87

2-[4-(5-Butyl-3-methyl-1H-pyrazol-1-yl)phenyl]ethyl (4-methylphenyl)sulfonylcarbamate Step 1. 2-[4-(5-Butyl-3-methyl-1H-pyrazol-1-yl)phenyl]ethanol and 2-[4-(3-Butyl-5-methyl-1H-pyrazol-1-yl)phenyl]ethanol The title compounds were prepared according to the procedure described in step 1 of Example 1 from octane-2, 4-dione and 2-(4-hydrazinophenyl)ethanol hydrochloride: 2-[4-(5-Butyl-3-methyl-1H-pyrazol-1-yl)phenyl]ethanol; $^{1}$H-NMR (CDCl$_3$) δ 7.31–7.23 (4H, m), 5.99 (1H, s), 3.70 (2H, d, J=6.8 Hz), 2.83 (2H, t, J=6.8 Hz), 2.29 (3H, s), 1.59–1.49 (2H, m), 1.37–1.25 (2H, m), 0.86 (3H, t, J=7.3 Hz): 2-[4-(3-Butyl-5-methyl-1H-pyrazol-1-yl)phenyl]ethanol; $^{1}$H-NMR (CDCl$_3$) δ 7.36–7.33 (2H, d, J=8.4 Hz), 7.27–7.24 (2H, d, J=8.5 Hz), 6.00 (1H, s), 3.75 (2H, d, J=6.8 Hz), 2.85 (2H, t, J=6.8 Hz), 2.63 (2H, d, J=7.5 Hz), 2.28 (3H, s), 1.70–1.60 (2H, m), 1.47–1.35 (2H, m), 0.94 (3H, t, J=7.5 Hz).

Step 2. 2-[4-(5-Butyl-3-methyl-1H-pyrazol-1-yl)phenyl]ethyl (4-methylphenyl)sulfonylcarbamate The title compound was prepared according to the procedure described in step 2 of Example 1 from 2-[4-(5-butyl-3-methyl-1H-pyrazol-1-yl)phenyl]ethanol (step 1): MS (ESI) m/z 456 [M+H]$^+$, 454 [M−H]$^-$, $^{1}$H-NMR (CDCl$_3$) δ 7.89 (2H, d, J=8.4 Hz), 7.31–7.26 (4H, m), 7.17 (2H, d, J=8.4 Hz), 6.00 (1H, s), 4.25 (2H, t, J=6.8 Hz), 2.89 (2H, t, J=6.8 Hz), 2.57 (3H, t, J=7.7 Hz), 2.41 (3H, s), 2.30 (3H, s), 1.59–1.49 (2H, m), 1.37–1.28 (2H, m), 0.86 (3H, t, J=7.3 Hz).

Example 88

2-[4-(3-Butyl-5-methyl-1H-pyrazol-1-yl)phenyl]ethyl (4-methylphenyl)sulfonylcarbamate The title compound was prepared according to the procedure described in step 2 of Example 1 from 2-[4-(3-butyl-5-methyl-1H-pyrazol-1-yl)phenyl]ethanol (step 1 of Example 87): MS (ESI) m/z 456 [M+H]$^+$, 454 [M−H]$^-$, $^{1}$H-NMR (CDCl$_3$) δ 7.90 (2H, d, J=8.4 Hz), 7.32 (4H, m), 7.18 (2H, d, J=8.3 Hz), 6.00 (1H, s), 4.26 (2H, t, J=6.8 Hz), 2.90 (2H, t, J=6.8 Hz), 2.63 (2H, t, J=7.5 Hz), 2.42 (3H, s), 2.28 (3H, s), 1.70–1.60 (2H, m), 3.47–1.35 (2H, m), 0.94 (3H, t, J=7.3 Hz).

Example 89

2-[4-(4-Cyclohexyl-3,5-dimethyl-1H-pyrazol-1-yl)phenyl]ethyl (4-methylphenyl)sulfonylcarbamate Step 1. 2-[4-(4-Cyclohexyl-3,5-dimethyl-1H-pyrazol-1-yl)phenyl]ethanol The title compound was prepared according to the procedure described in step 1 of Example 1 from 3-cyclohexylpentane-2,4-dione (*Tetrahedron*, 1991, 47, 6511) and 2-(4-hydrazinophenyl)ethanol hydrochloride: $^{1}$H-NMR (CDCl$_3$) δ 7.36–7.30 (4H, m), 391 (2H, t, J=6.6 Hz), 2.91 (2H, t, J=6.6 Hz), 2.31 (3H, s), 2.24 (3H, s), 1.82–1.26 (11H, m).

Step 2. 2-[4-(4-Cyclohexyl-3,5-dimethyl-1H-pyrazol-1-yl)phenyl]ethyl (4-methylphenyl)sulfonylcarbamate The title compound was prepared according to the procedure described in step 2 of Example 1 from 2-[4-(4-cyclohexyl-3,5-dimethyl-1H-pyrazol-1-yl)phenyl]ethanol (step 1): MS (ESI) m/z 496 [M+H]$^+$, 494 [M−H]$^-$, $^{1}$H-NMR (CDCl$_3$) δ 7.90–7.87 (2H, d, J=8.4 Hz), 7.37–7.20 (4H, m), 7.18–7.14 (2H, d, J=8.3 Hz), 4.27 (2H, t, J=6.8 Hz), 2.91 (2H, t, J=6.8 Hz), 2.42 (3H, s), 2.31 (3H, s), 2.27 (3H, s), 1.86–1.60 (8H, m), 1.39–1.21 (4H, m).

Example 90

2-[4-(4-Cyclohepta-2,4,6-trien-1-yl-3,5-dimethyl-1H-pyrazol-1-yl)phenyl]ethyl (4-methylphenyl)sulfonylcarbamate Mono-p-toluenesulfonamide Step 1. 2-[4-(4-Cyclohepta-2,4,6-trien-1-yl-3,5-dimethyl-1H-pyrazol-1-yl)phenyl]ethanol The title compound was prepared according to the procedure described in step 1 of Example 1 from 3-cyclohepta-2,4,6-trien-1-ylpentane-2,4-dione and 2-(4-hydrazinophenyl)ethanol hydrochloride: MS (EI) m/z 306 [M]$^+$.

Step 2. 2-[4-(4-Cyclohepta-2,4,6-trien-1-yl-3,5-dimethyl-1H-pyrazol-1-yl)phenyl]ethyl (4-methylphenyl)sulfonylcarbamate The title compound was prepared according to the procedure described in step 2 of Example 1 from 2-[4-(4-cyclohepta-2,4,6-trien-1-yl-3,5-dimethyl-1H-pyrazol-1-yl)phenyl]ethanol (step 1): MS (ESI) m/z 504 [M+H]$^+$, 502 [M−H]$^-$.

Step 3. 2-[4-(4-Cyclohepta-2,4,6-trien-1-yl-3,5-dimethyl-1H-pyrazol-1-yl)phenyl]ethyl (4-methylphenyl)sulfonylcarbamate Mono-p-toluenesulfonamide The title compound was prepared according to the procedure described in step 6 of Example 15 from 2-[4-(4-cyclohepta-2,4,6-trien-1-yl-3,5-dimethyl-1H-pyrazol-1-yl)phenyl]ethyl (4-methylphenyl)sulfonylcarbamate (step 2): MS (ESI) m/z 504 [M+H]$^+$, 502 [M−H]$^-$.

Example 91

2-[4-(4-Benzyl-3,5-dimethyl-1H-pyrazol-1-yl)phenyl]ethyl (4-Methylphenyl)sulfonylcarbamate Mono-p-toluenesulfonamide Step 1. 2-[4-(4-Benzyl-3,5-dimethyl-1H-pyrazol-1-yl)phenyl]ethanol The title compound was prepared according to the procedure described in step 1 of Example 1 from 3-benzylpentane-2,4-dione and 2-(4-hydrazinophenyl)ethanol hydrochloride: $^{1}$H-NMR (CDCl$_3$) δ 7.39–7.15 (9H, m), 3.89–3.85 (2H, t, J=6.4 Hz), 3.48 (2H, s), 2.91 (2H, t, J=6.6 Hz), 2.29 (3H, s), 2.21 (3H, s).

Step 2. 2-[4-(4-Benzyl-3,5-dimethyl-1H-pyrazol-1-yl)phenyl]ethyl (4-methylphenyl)sulfonylcarbamate The title compound was prepared according to the procedure described in step 2 of Example 1 from 2-[4-(4-benzyl-3,5-dimethyl-1H-pyrazol-1-yl)phenyl]ethanol (step 1): MS (ESI) m/z 504 [M+H]$^+$, 502 [M−H]$^-$.

Step 3. 2-[4-(4-Benzyl-3,5-dimethyl-1H-pyrazol-1-yl)phenyl]ethyl (4-methylphenyl)sulfonylcarbamate mono-p-toluenesulfonamide The title compound was prepared according to the procedure described in step 6 of Example 15 from 2-[4-(4-benzyl-3,5-dimethyl-1H-pyrazol-1-yl)phenyl]ethyl (4-methylphenyl)sulfonylcarbamate (step 2): MS (ESI) m/z 504 [M+H]$^+$, 502 [M−H]$^-$.

Example 92

2-(4-{4-[4-(Acetylamino)phenyl]-3,5-dimethyl-1H-pyrazol-1-yl}phenyl)ethyl (4-methylphenyl)sulfonylcarbamate Mono-p-toluenesulfonamide Step 1. N-(4-{1-[4-(2-Hydroxyethyl)phenyl]-3,5-dimethyl-1H-pyrazol-4-yl}phenyl)acetamide The title compound was prepared according to the procedure described in step 1 of Example 12 from 2-[4-(4-iodo-3,5-dimethyl-1H-pyrazol-1-yl)phenyl]ethanol (step 2 of Example 11) and 4'-(4,4,5,5-tetramethyl-1,3,2-dioxaborolan-2-yl)acetanilide: MS (EI) m/z 385 [M]+, $^{1}$H-NMR (CDCl$_3$) δ 7.44–7.26 (8H, m), 3.92–3.90 (2H, br), 3.08 (3H, s), 2.94 (2H, t, J=6.6 Hz), 2.32 (3H, s), 2.29 (3H, s).

Step 2. 2-(4-{4-[4-(Acetylamino)phenyl]-3,5-dimethyl-1H-pyrazol-1-yl}phenyl)ethyl (4-methylphenyl)sulfonylcarbamate The title compound was prepared according to the procedure described in step 2 of Example 1 from N-(4-{1-[4-

(2-hydroxyethyl)phenyl]-3,5-dimethyl-1H-pyrazol-4-yl}phenyl)acetamide (step 1): MS (ESI) m/z 547 [M+H]⁺, 545 [M–H]⁻.

Step 3. 2-(4-{4-[4-(Acetylamino)phenyl]-3,5-dimethyl-1H-pyrazol-1-yl} phenyl)ethyl (4-methylphenyl)sulfonylcarbamate mono-p-toluenesulfonamide The title compound was prepared according to the procedure described in step 6 of Example 15 from 2-(4-{4-[4-(acetylamino)phenyl]-3,5-dimethyl-1H-pyrazol-1-yl}phenyl)ethyl (4-methylphenyl)sulfonylcarbamate (step 2): MS (ESI) m/z 547 [M+H]⁺, 545 [M–H]⁻.

Example 93

2-[4-(3,5-Dimethyl-4-{4-[(Methylsulfonyl)amino]phenyl}-1H-pyrazol-1-yl)phenyl]ethyl (4-methylphenyl)sulfonylcarbamate Mono-p-toluenesulfonamide Step 1. N-(4-{1-[4-(2-Hydroxyethyl)phenyl]-3,5-dimethyl-1H-pyrazol-4-yl}phenyl)methanesulfonamide The title compound was prepared according to the procedure described in step 1 of Example 12 from 2-[4-(4-iodo-3,5-dimethyl-1H-pyrazol-1-yl)phenyl]ethanol (step 2 of Example 11) and N-[4-(4,4,5,5-tetramethyl-1,3,2-dioxaborolan-2-yl)phenyl]methanesulfonamide: MS (EI) m/z 385 [M]⁺, ¹H-NMR (CDCl₃) δ 7.44–7.26 (8H, m), 3.92–3.90 (2H, br), 3.08 (3H, s), 2.94 (2H, t, J=6.6 Hz), 2.32 (3H, s), 2.29 (3H, s).

Step 2. 2-[4-(3,5-Dimethyl-4-4-[(methylsulfonyl)amino]phenyl}-1H-pyrazol-1-yl)phenyl]ethyl (4-methylphenyl)sulfonylcarbamate The title compound was prepared according to the procedure described in step 2 of Example 1 from N-(4-{1-[4-(2-hydroxyethyl)phenyl]-3,5-dimethyl-1H-pyrazol-4-yl}phenyl)methanesulfonamide (step 1): MS (ESI) m/z 583 [M+H]⁺, 581 [M–H]⁻, ¹H-NMR (CDCl₃) δ 7.90 (2H, d, J=8.4 Hz), 7.40–7.22 (10H, m), 4.30 (2H, t, J=6.8 Hz), 2.94 (2H, t, J=6.8 Hz), 3.08 (3H, s), 2.43 (3H, s), 2.31 (3H, s), 2.26 (3H, s).

Step 3. 2-[4-(3,5-Dimethyl-4-{4-[(methylsulfonyl)amino]phenyl}-1H-pyrazol-1-yl)phenyl]ethyl (4-methylphenyl)sulfonylcarbamate Mono-p-toluenesulfonamide The title compound was prepared according to the procedure described in step 6 of Example 15 from 2-[4-(3,5-dimethyl-4-{4-[(methylsulfonyl)amino]phenyl}-1H-pyrazol-1-yl)phenyl]ethyl (4-methylphenyl)sulfonylcarbamate (step 2): MS (ESI) m/z 583 [M+H]⁺, 581 [M–H]⁻.

Example 94

2-{4-[4-(4-Methoxyphenyl)-3,5-dimethyl-1H-pyrazol-1-yl]phenyl}ethyl (4-methylphenyl)sulfonylcarbamate Mono-p-toluenesulfonamide Step 1. 2-{4-[4-(4-Methoxyphenyl)-3,5-dimethyl-1H-pyrazol-1-yl]phenyl}ethanol The title compound was prepared according to the procedure described in step 1 of Example 12 from 2-[4-(4-iodo-3,5-dimethyl-1H-pyrazol-1-yl)phenyl]ethanol (step 2 of Example 11) and 4-methoxyphenylboronic acid: MS (ESI) m/z 323 [M+H]+H-NMR (CDCl₃) δ 7.39 (2H, d, J=8.1 Hz), 7.29–7.22 (4H, m), 6.98 (2H, d, J=9.6 Hz), 3.86 (3H, s), 3.74 (2H, br), 2.86 (2H, t, J=6.6 Hz), 2.33 (3H, s), 2.28 (3H, s).

Step 2. 2-{4-[4-(4-Methoxyphenyl)-3,5-dimethyl-1H-pyrazol-1-yl]phenyl}ethyl (4-methylphenyl)sulfonylcarbamate The title compound was prepared according to the procedure described in step 2 of Example 1 from 2-{4-[4-(4-methoxyphenyl)-3,5-dimethyl-1H-pyrazol-1-yl]phenyl}ethanol (step 1): MS (ESI) m/z 520 [M+H]⁺, 518 [M–H]⁻.

Step 3. 2-{4-[4-(4-Methoxyphenyl)-3,5-dimethyl-1H-pyrazol-1-yl]phenyl}ethyl (4-methylphenyl)sulfonylcarbamate Mono-p-toluenesulfonamide The title compound was prepared according to the procedure described in step 6 of Example 15 from 2-{4-[4-(4-methoxyphenyl)-3,5-dimethyl-1H-pyrazol-1-yl]phenyl}ethyl (4-methylphenyl)sulfonylcarbamate (step 2): MS (ESI) m/z 520 [M+H]⁺, 518 [M–H]⁻.

Example 95

2-{4-[3,5-Dimethyl-4-(1,3-thiazol-2-yl)-1H-pyrazol-1-yl]phenyl}ethyl (4-Methylphenyl)sulfonylcarbamate Mono-sodium Salt Step 1. 2-{4-[3,5-Dimethyl-4-(1,3-thiazol-2-yl)-1H-pyrazol-1-yl]phenyl}ethanol A mixture of 2-[4-(4-iodo-3,5-dimethyl-1H-pyrazol-1-yl)phenyl]ethanol (step 2 of Example 11) (855 mg, 2.5 mmol), 2-tributylstannylthiazole (3 mmol) and tetrakistriphenylophosphinepalladium (346 mg, 0.3 mol) in m-xylene (6 mL) was refluxed for 16 h. The mixture was filtered through a pad of Celite and the filtrate was concentrated. The crude product was purified by TLC with hexane/ethyl acetate (1:1) to afford 39 mg (5%) of the title compound as yellow oil: MS (EI) m/z 299 [M]⁺.

Step 2. 2-{4-[3,5-Dimethyl-4-(1,3-thiazol-2-yl)-1H-pyrazol-1-yl]phenyl}ethyl (4-methylphenyl)sulfonylcarbamate The title compound was prepared according to the procedure described in step 2 of Example 1 from 2-{4-[3,5-dimethyl-4-(1,3-thiazol-2-yl)-1H-pyrazol-1-yl]phenyl}ethanol (step 1): MS (ESI) m/z 497 [M+H]⁺, 495 [M–H]⁻, ¹H-NMR (CDCl₃) δ 7.87 (1H, d, J=3.5 Hz), 7.80 (2H, d, J=8.3 Hz), 7.58 (1H, d, J=3.5 Hz), 7.34–7.29 (6H, m), 4.22 (2H, t, J=6.8 Hz), 2.94 (2H, t, J=6.8 Hz), 2.48 (3H, s), 2.47 (3H, s), 2.36 (3H, s).

Step 3. 2-{4-[3,5-Dimethyl-4-(1,3-thiazol-2-yl)-1H-pyrazol-1-yl]phenyl}ethyl (4-methylphenyl)sulfonylcarbamate mono-sodium salt The title compound was prepared according to the procedure described in step 4 of Example 8 from 2-{4-[3,5-dimethyl-4-(1,3-thiazol-2-yl)-1H-pyrazol-1-yl]phenyl}ethyl (4-methylphenyl)sulfonylcarbamate (step 2): MS (ESI) m/z 497 [M+H]⁺, 495 [M–H]⁻.

Example 96

2-{4-[5-Methyl-4-phenyl-3-(trifluoromethyl)-1H-pyrazol-1-yl]phenyl}ethyl (4-methylphenyl)sulfonylcarbamate The title compound was prepared according to the procedure described in step 2 of Example 1 from 2-{4-[5-methyl-4-phenyl-3-(trifluoromethyl)-1H-pyrazol-1-yl]phenyl}ethanol (step 3 of Example 52): MS (ESI) m/z 544 [M+H]⁺, 542 [M–H]⁻.

Example 97

2-[4-(3-Tert-butyl-5-methyl-4-phenyl-1H-pyrazol-1-yl)phenyl]ethyl (4-methylphenyl)sulfonylcarbamate Step 1. 2-[4-(3-tert-butyl-5-methyl-1H-pyrazol-1-yl)phenyl]ethanol The title compound was prepared according to the procedure described in step 1 of Example 63 from propynylmagnesium bromide, pivaloyl chloride and 2-(4-hydrazinophenyl)ethanol hydrochloride: MS (EI) m/z 334 [M]+, ¹H-NMR (CDCl₃) δ 7.39–7.29 (4H, m), 6.05 (1H, s), 3.85 (2H, m), 2.90 (2H, m), 2.30 (3H, s), 1.60 (1H, br.s), 1.33 (9H, s).

Step 2. 2-[4-(4-bromo-3-tert-butyl-5-methyl-1H-pyrazol-1-yl)phenyl]ethanol

The title compound was prepared according to the procedure described in step 2 of Example 52 from 2-[4-(3-tert-butyl-5-methyl-1H-pyrazol-1-yl)phenyl]ethanol (step 1): MS (EI) m/z 336 [M]⁺.

Step 3. 2-[4-(3-tert-butyl-5-methyl-4-phenyl-1H-pyrazol-1-yl)phenyl]ethanol

The title compound was prepared according to the procedure described in step 1 of Example 95 from 2-[4-(4-bromo-3-tert-butyl-5-methyl-1H-pyrazol-1-yl)phenyl]ethanol (step 2): MS (EI) m/z 334 [M]⁺.

Step 4. 2-[4-(3-tert-butyl-5-methyl-4-phenyl-1H-pyrazol-1-yl)phenyl]ethyl (4-methylphenyl)sulfonylcarbamate The title compound was prepared according to the procedure described in step 2 of Example 1 from 2-[4-(3-tert-butyl-5-methyl-4-phenyl-1H-pyrazol-1-yl)phenyl]ethanol (step 3): MS (ESI) m/z 532 [M+H]⁺, 530 [M−H]⁻.

Example 98

N-{[(2-{4-[4-(3,4-Dimethoxyphenyl)-3,5-dimethyl-1H-pyrazol-1-yl]phenyl}ethyl)amino]carbonyl}-4-methylbenzenesulfonamide Mono-sodium Salt Step 1. 2-[4-[4-(3,4-Dimethoxyphenyl)-3,5-dimethyl-1H-pyrazol-1-yl]phenyl}ethanol The title compound was prepared according to the procedure described in step 1 of Example 12 from 2-[4-(4-iodo-3,5-dimethyl-1H-pyrazol-1-yl)phenyl]ethanol (step 2 of Example 11) and 3,4-dimethoxyphenylboronic acid: MS (ESI) m/z 353 [M+H]⁺.

Step 2. 2-{4-[4-(3,4-Dimethoxyphenyl)-3,5-dimethyl-1H-pyrazol-1-yl]phenyl}ethyl Methanesulfonate The title compound was prepared according to the procedure described in step 4 of Example 52 from 2-{4-[4-(3,4-dimethoxyphenyl)-3,5-dimethyl-1H-pyrazol-1-yl]phenyl}ethanol (step 1): MS (ESI) m/z 431 [M+H]⁺, 429 [M−H]⁻, ¹H-NMR (CDCl₃) δ 7.49–7.39 (3H, m), 6.98–6.82 (3H, m), 4.48–4.43 (2H, t, J=6.7 Hz), 3.93 (3H, s), 3.91 (3H, s), 3.93 (3H, s), 3.91 (3H, s), 3.15–3.10 (2H, t, J=6.7 Hz), 2.36 (3H, s), 2.30 (3H, s).

Step 3. 1-[4-(2-Azidoethyl)phenyl]-4-(3,4-dimethoxyphenyl)-3,5-dimethyl-1H-pyrazole The title compound was prepared according to the procedure described in step 2 of Example 14 from 2-{4-[4-(3,4-dimethoxyphenyl)-3,5-dimethyl-1H-pyrazol-1-yl]phenyl}ethyl methanesulfonate (step 2): MS (ESI) m/z 378 [M+H]⁺, ¹H-NMR (CDCl₃) δ 7.45 (2H, d, J=8.4 Hz), 7.33 (2H, d, J=8.4 Hz), 6.96 (1H, d, J=8.1 Hz), 6.88–6.85 (2H, m), 3.93 (3H, s), 3.92 (3H, s), 3.55 (2H, t, J=7.2 Hz), 2.96 (2H, t, J=7.2 Hz), 2.33 (3H, s), 2.30 (3H, s).

Step 4. 2-{4-[4-(3,4-Dimethoxyphenyl)-3,5-dimethyl-1H-pyrazol-1-yl]phenyl}ethanamine The title compound was prepared according to the procedure described in step 3 of Example 14 from 1-[4-(2-azidoethyl)phenyl]-4-(3,4-dimethoxyphenyl)-3,5-dimethyl-1H-pyrazole (step 3): ¹H-NMR (CDCl₃) δ 7.40–7.27 (4H, m), 6.93–6.82 (2H, m), 6.82 (1H, s), 3.89 (3H, s), 3.88 (3H, s), 2.99 (2H, t, J=6.8 Hz), 2.85 (2H, t, J=6.8 Hz), 2.64 (2H, br.s), 2.29 (3H, s), 2.25 (3H, s).

Step 5. N-{[2-{4-[4-(3,4-Dimethoxyphenyl)-3,5-dimethyl-1H-pyrazol-1-yl]phenyl}ethyl)amino]carbonyl}-4-methylbenzenesulfonamide The title compound was prepared according to the procedure described in step 2 of Example 1 from 2-{4-[4-(3,4-dimethoxyphenyl)-3,5-dimethyl-1H-pyrazol-1-yl]phenyl}ethanamine (step 4): ¹H-NMR (CDCl₃) δ 7.68 (2H, d, J=8.3 Hz), 7.41 (2H, d, J=8.2 Hz), 7.33–7.26 (4H, m), 6.96–6.84 (2H, m), 6.84 (1H, s), 6.68 (1H, br.s), 3.93 (3H, s), 3.91 (3H, s), 3.52 (2H, br.s), 2.87 (2H, br.s), 2.42 (3H, s), 2.33 (3H, s), 2.28 (3H, s).

Step 6. N-{[(2-{4-[4-(3,4-Dimethoxyphenyl)-3,5-dimethyl-1H-pyrazol-1-yl]phenyl}ethyl)amino]carbonyl}-4-methylbenzenesulfonamide mono-sodium salt The title compound was prepared according to the procedure described in step 4 of Example 8 from N-{[(2-{4-[4-(3,4-dimethoxyphenyl)-3,5-dimethyl-1H-pyrazol-1-yl]phenyl}ethyl)amino]carbonyl}-4-methylbenzenesulfonamide (step 5): MS (ESI) m/z 549 [M+H]⁺, 547 [M−H]⁻.

Example 99

4-Chloro-N-{[(2-{4-[5-methyl-4-phenyl-3-(trifluoromethyl)-1H-pyrazol-1-yl]phenyl}ethyl)amino]carbonyl}benzenesulfonamide Mono-sodium Salt Step 1. 4-Chloro-N-{[(2-{4-[5-methyl-4-phenyl-3-(trifluoromethyl)-1H-pyrazol-1-yl]phenyl}ethyl)amino]carbonyl}benzenesulfonamide The title compound was prepared according to the procedure described in step 4 of Example 14 from 2-{4-[5-methyl-4-phenyl-3-(trifluoromethyl)-1H-pyrazol-1-yl]phenyl}ethanamine (step 6 of Example 52): MS (ESI) m/z 563 [M+H]⁺, 561 [M−H]⁻.

Step 2. 4-Chloro-N-{[(2-{4-[5-methyl-4-phenyl-3-(trifluoromethyl)-1H-pyrazol-1-yl]phenyl}ethyl)amino]carbonyl}benzenesulfonamide mono-sodium salt The title compound was prepared according to the procedure described in step 4 of Example 8 from 4-chloro-N-{[(2-{4-[5-methyl-4-phenyl-3-(trifluoromethyl)-1H-pyrazol-1-yl]phenyl}ethyl)amino]carbonyl}benzenesulfonamide (step 1): MS (ESI) m/z 563 [M+H]⁺, 561 [M−H]⁻.

Example 100

2-[4-(3-Methyl-4-phenyl-1H-pyrazol-1-yl)phenyl]ethyl (4-methylphenyl)sulfonylcarbamate Step. 1 4-(2-Hydroxyethyl)phenylboronic acid To a stirred solution of 4-bromophenethylalcohol (5.00 g, 24.9 mmol) in tetrahydrofuran (80 mL) was added a solution of 1.5 M n-butyl lithium in hexane (39.8 mL, 59.7 mmol) at −78° C. over 30 min. After 1 h, a solution of triisopropyl borate (8.61 mL, 37.3 mmol) in tetrahydrofuran (20 mL) was added slowly to the mixture at −78° C. The resultant mixture was warmed to room temperature, and treated with 2 M HCl (100 mL) for 1 h. This mixture was extracted with dichloromethane and dried (MgSO₄). After evaporation in vacuo, the residue was purified by silica-gel column chromatography eluting with dichloromethane/methanol (20:1) to afford 2.61 g (63%) of the title compound as white solids: MS (ESI) m/z 165 [M−H]⁻, ¹H-NMR (CD₃OD) δ 7.64–7.48 (2H, m), 7.19–7.13 (2H, m), 3.70 (2H, t, J=7.2 Hz), 2.77 (2H, t, J=7.2 Hz).

Step 2. 4-{2-[({[(4-Methylphenyl)sulfonyl]amino}carbonyl)oxy]ethyl}phenylboronic Acid 4-(2-Hydroxyethyl)phenylboronic acid (step 1, 1.00 g, 6.02 mmol) was treated with pyridine (90 mL) and p-toluenesulfonylisocyanate (1.01 mL, 6.63 mmol) at room temperature for 2 h. The mixture was poured into ice-2 M HCl (200 mL) and extracted with ethyl acetate, (300 mL), and the organic fraction was dried (MgSO$_4$). After removal of solvent, the residue was purified by silica-gel column chromatography eluting with dichloromethane/methanol (20:1) to give 2.20 g (quant.) of the title compound as white solids: MS (ESI) m/z 381 [M+NH$_4$]$^+$, 362 [M–H]$^-$, $^1$H-NMR (DMSO-d$_6$) δ 11.95 (1H, br.s), 7.97 (1H, s), 7.75–7.67 (2H, m), 7.40 (2H, d, J=8.6 Hz), 7.13 (2H, d, J=7.7 Hz), 4.18 (2H, t, J=6.6 Hz), 2.81 (2H, t, J=6.6 Hz), 2.40 (3H, s).

Step 3. 2-[4-(3-Methyl-4-phenyl-1H-pyrazol-1-yl)phenyl] ethyl (4-methylphenyl)sulfonylcarbamate A mixture of 4-{2-[({[(4-methylphenyl)sulfonyl]amino}carbonyl)oxy]ethyl}phenylboronic acid (200 mg, 0.55 mmol), 3-methyl-4-phenylpyrazole (87 mg, 0.55 mmol), Copper(II) acetate (120 mg, 0.66 mmol), triethylamine (0.23 mL, 1.65 mmol), molecular sieves 4A (200 mg), and dichloromethane (8 mL) was stirred at room temperature for 3 days. After filtration through a bed of celite, the filtrate was diluted with dichloromethane, and washed with water. The organic fraction was dried over MgSO$_4$. After concentration under reduced pressure, the residue was purified by TLC with dichloromethane/ethylacetate (10:1) to afford 56 mg (21%) of the title compound as white solids: MS (ESI) m/z 476 [M+H]$^+$, 474 [M–H]$^-$, $^1$H-NMR (CDCl$_3$) δ 7.88 (2H, d, J=8.5 Hz), 7.61–7.19 (11H, m), 4.31 (2H, t, J=6.6 Hz), 2.92 (2H, t, J=6.6 Hz), 2.49 (3H, s), 2.42 (3H, s).

General Procedure From Example 101 to 115

(1$^{st}$ Step)

A mixture of 2-[4-(4-iodo-3,5-dimethyl-1H-pyrazol-1-yl)phenyl]ethanol (step 2 of Example 11, 30 mg, 0.0877 mmol, 1eq), PdCl$_2$(PPh$_3$)$_2$ (20 mol %) and boronic acid (3 eq) in dimethoxyethane-2 M K$_2$CO$_3$ aq. (4:1, 1.1 mL) was agitated under 80° C. for 16 h. After the mixture was cooled, to the residue were added CHCl$_3$ (2 mL) and aqueous sat. NaCl (0.22 mL). The organic layers were extracted and loaded onto Varian Chem Elute (1 mL) (removal of a small amount of water layer and Pd black). After 10 min, the organic solution was eluted with CHCl$_3$ (6 mL) and concentrated in vacuo. The residue was diluted with CHCl$_3$/CH$_3$OH (3:1, 3 mL), and loaded onto SPE-SCX (1 g/6 mL) pre-washed with CH$_3$OH (8 mL). The solid phase matrix was washed with CHCl$_3$/CH$_3$OH(3:1, 4 mL) followed by CH$_3$OH (4 mL) and then eluted with 2 M NH$_3$ in CH$_3$OH (5 mL). The solution was concentrated in vacuo to afford the coupling product {2-[4-(4-aryl-3,5-dimethyl-1H-pyrazol-1-yl)phenyl]ethanol}.

(2$^{nd}$ Step)

The coupling product (step 1, 2-[4-(4-aryl-3,5-dimethyl-1H-pyrazol-1-yl)phenyl]ethanol)} was diluted with CHCl$_3$ (1 mL). Then 1 M solution of p-toluenesulfonyl isocyanate (2 eq.) in CHCl$_3$ was added to the mixture at room temperature and the mixture was shaken with a shaker for 30 min. (The reaction was checked by LC/MS. If the reaction was not completed, more reagent was added.) After the starting material was disappeared, to the resultant mixture was added CH$_3$OH (250 μL) and shaken for 15 min. The mixture was then loaded onto SPE-SCX (1 g/6 mL) pre-washed with CH$_3$OH (8 mL). The solid phase matrix was washed with CHCl$_3$—CH$_3$OH (3:1, 4 mL) followed by CH$_3$OH (4 mL) and then eluted with 2 M NH$_3$ in CH$_3$OH (5 mL). The eluted solution was concentrated in vacuo to afford the coupling product. When the purity was not enough, the residue was purified by preparative LC/MS (Shiseido capcell pack UG80 C18 (4.6×50 mm) eluting with CH$_3$OH/0.1% NH$_3$ (v/v, 20:80 to 90:10) to give the title compound. The following examples were synthesized by the described protocol.

Example 101

2-{4-[4-(4-Fluorophenyl)-3,5-imethyl-1H-pyrazol-1-yl]phenyl}ethyl (4-methylphenyl)sulfonylcarbamate Ammonium Salt MS (ESI) m/z 508.03 [M+H]$^+$.

Example 102

2-{4-[3,5-Dimethyl-4-(4-methylphenyl)-1H-pyrazol-1-yl]phenyl}ethyl (4-methylphenyl) sulfonylcarbamate Ammonium Salt MS (ESI) m/z 503.97 [M+H]$^+$.

Example 103

2-{4-[3,5-Dimethyl-4-(2-Naphthyl)-1H-pyrazol-1-yl]phenyl}ethyl (4-methylphenyl)sulfonylcarbamate Ammonium Salt MS (ESI) m/z 539.95 [M+H]$^+$.

Example 104

2-{4-[3,5-Dimethyl-4-(3-methylphenyl)-1H-pyrazol-1-yl]phenyl}ethyl (4-methylphenyl) sulfonylcarbamate Ammonium Salt MS (ESI) m/z 503.99 [M+H]$^+$.

Example 105

2-(4-{3,5-Dimethyl-4-[3-(trifluoromethyl)phenyl]-1H-pyrazol-1-yl}Phenyl)ethyl (4-methylphenyl) sulfonylcarbamate, Ammonium Salt MS (ESI) m/z 557.99 [M+H]$^+$.

Example 106

2-{4-[4-(3-Methoxyphenyl)-3,5-dimethyl-1H-pyrazol-1-yl]phenyl}ethyl (4-methylphenyl) sulfonylcarbamate Ammonium Salt MS (ESI) m/z 520.04 [M+H]$^+$.

Example 107

2-{4-[4-(3,5-Difluorophenyl)-3,5-dimethyl-1H-pyrazol-1-yl]phenyl}ethyl (4-Methylphenyl) sulfonylcarbamate Ammonium Salt MS (ESI) m/z: 526.09 [M+H]$^+$.

Example 108

2-{4-[4-(3,4-Dimethoxyphenyl)-3,5-dimethyl-1H-pyrazol-1-yl]phenyl}ethyl (4-methylphenyl) sulfonylcarbamate Ammonium Salt MS (ESI) m/z 550.22 [M+H]$^+$.

Example 109

2-{4-[4-(4-Ethoxyphenyl)-3,5-dimethyl-1H-pyrazol-1-yl]phenyl}ethyl (4-methylphenyl) sulfonylcarbamate Ammonium Salt MS (ESI) m/z 534.2 [M+H]$^+$.

Example 110

2-{4-[4-(3-Fluorophenyl)-3,5-dimethyl-1H-pyrazol-1-yl]phenyl}ethyl (4-methylphenyl)sulfonylcarbamate After the described procedure, further purification was performed by the preparative TLC (8% CH$_3$OH in CHCl$_3$): MS (ESI) m/z 508.25 [M+H]$^+$.

Example 111

2-{4-[4-(3-Hydroxyphenyl)-3,5-dimethyl-1H-pyrazol-1-yl]phenyl}ethyl (4-methylphenyl)sulfonylcarbamate Ammonium Salt MS (ESI) m/z 506.34 [M+H]$^+$.

Example 112

2-(4-{4-[6-(Dimethylamino)-3-pyridinyl]-3,5-dimethyl-1H-pyrazol-1-yl}Phenyl)ethyl (4-methylphenyl)sulfonylcarbamate Ammonium Salt MS (ESI) m/z 534.41 [M+H]$^+$.

Example 113

2-{4-[4-(4-Hydroxyphenyl)-3,5-dimethyl-1H-pyrazol-1-yl]phenyl}ethyl (4-methylphenyl)sulfonylcarbamate After the described procedure, further purification was performed by the preparative TLC (8% CH$_3$OH in CHCl$_3$): MS (ESI) m/z 506.31 [M+H]$^+$.

Example 114

2-[4-(3,5-Dimethyl-4-quinolin-3-yl-1H-pyrazol-1-yl)phenyl]ethyl (4-methylphenyl)sulfonylcarbamate After the described procedure, further purification was performed by the preparative TLC (8% CH$_3$OH in CHCl$_3$): MS (ESI) m/z 541.23 [M+H]$^+$.

Example 115

2-{4-[4-(3,4-Dichlorophenyl)-3,5-dimethyl-1H-pyrazol-1-yl]phenyl}ethyl (4-methylphenyl)sulfonylcarbamate Ammonium Salt MS (ESI) m/z 558.06 [M+H]$^+$.

What is claimed is:

1. A compound of the following formula (I):

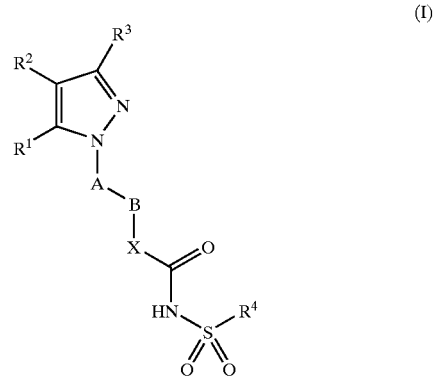

wherein:

R$^1$ represents a hydrogen atom, an alkyl group having from 1 to 6 carbon atoms, an amino group, mono- or di-alkylamino groups, the alkyl group(s) having from 1 to 6 carbon atoms, or an aryl group;

R$^2$ represents a hydrogen atom, a halogen atom, an alkyl group having from 1 to 6 carbon atoms, a cycloalkyl group having from 3 to 8 carbon atoms, a cycloalkenyl group having from 3 to 10 carbon atoms, an aralkyl group, or an aryl group;

R$^3$ represents an alkyl group having from 1 to 6 carbon atoms, a haloalkyl group having from 1 to 6 carbon atoms, a hydroxyalkyl group having from 1 to 6 carbon atoms, or an aryl group;

R$^4$ represents an aryl group;

A represents an aryl group having from 6 to 10 carbon atoms;

B represents an alkylene group having from 1 to 6 carbon atoms;

X represents NH, N[(C$_1$–C$_6$)alkyl], oxygen or sulfur;

said aryl groups have 6 to 14 carbon atoms;

said aryl groups are unsubstituted or are substituted by at least one substituent selected from the group consisting of substituents α, defined below;

said aralkyl groups are alkyl groups having from 1 to 6 carbon atoms and which are substituted by at least one aryl group as defined above;

said substituents α are selected from the group consisting of an aryl group as defined above, hydroxy group, halogen atoms, alkyl group having from 1 to 6 carbon atoms, alkoxy group having from 1 to 6 carbon atoms, alkylthio group having from 1 to 6 carbon atoms, alkanoyl group having from 1 to 6 carbon atoms, alkanoylamino group having from 1 to 6 carbon atoms, alkanoylaminoalkyl group having from 1 to 6 carbon atoms in the alkanoyl and alkyl part, amino group, mono- or di-alkylamino group having from 1 to 6 carbon atoms, haloalkyl group having from 1 to 6 carbon atoms, haloalkoxy group having from 1 to 6 carbon atoms, carbamoyl group, cyano group, a hydroxyalkyl group having from 1 to 6 carbon atoms, alkylsufinyl group having from 1 to 6 carbon atoms, alkylsufonyl group having from 1 to 6 carbon atoms, aminoalkoxy group having from 1 to 6 carbon atoms, mono- or di-alkylaminoalkoxy group, the alkyl group(s) having from 1 to 6 carbon atoms in the alkyl and alkoxy part, alkylsulfonylamino group having from 1 to 6 carbon atoms and aminosulfonyl group; with the proviso that said aryl group in said substituents α are not substituted by an aryl group; or a pharmaceutically acceptable ester of such compound, or a pharmaceutically acceptable salt thereof.

2. A compound according to claim 1, wherein $R^1$ represents an alkyl group having from 1 to 6 carbon atoms, an amino group or an aryl group.

3. A compound according to claim 1, wherein $R^2$ represents a hydrogen atom, a halogen atom, an alkyl group having from 1 to 6 carbon atoms, a cycloalkyl group having from 3 to 8 carbon atoms, an aralkyl group, or an aryl group.

4. A compound according to claim 1, wherein $R^2$ represents a hydrogen atom, an alkyl group having from 1 to 6 carbon atoms, a cycloalkyl group having from 3 to 8 carbon atoms, or an aryl group; said aryl groups are unsubstituted or are substituted by at least one substituent selected from the group consisting of substituents α, defined below; said substituents α are selected from the group consisting of alkyl groups having from 1 to 6 carbon atoms, hydroxy groups, halogen atoms, alkoxy groups having from 1 to 6 carbon atoms, alkanoylamino groups having from 1 to 6 carbon atoms, di-alkylamino groups, the alkyl group(s) having from 1 to 6 carbon atoms, haloalkyl groups having from 1 to 6 carbon atoms and carbamoyl groups.

5. A compound according to claim 1, wherein $R^3$ represents an alkyl group having from 1 to 6 carbon atoms, a haloalkyl group having from 1 to 6 carbon atoms or an unsubstituted aryl group having from 6 to 10 carbon atoms.

6. A compound according to claim 1, wherein $R^4$ represents an aryl group; said aryl group is unsubstituted or is substituted by at least one substituent selected from the group consisting of substituents α, defined below;
said substituents α are selected from the group consisting of alkyl groups having from 1 to 6 carbon atoms, hydroxy groups, halogen atoms, alkoxy groups having from 1 to 6 carbon atoms, haloalkoxy groups having from 1 to 6 carbon atoms, alkanoyl groups having from 1 to 6 carbon atoms, alkanoylaminoalkyl groups having from 1 to 6 carbon atoms in the alkanoyl and alkyl part, haloalkyl groups having from 1 to 6 carbon atoms, carbamoyl groups, cyano groups and aminosulfonyl groups.

7. A compound according to claim 1, wherein $R^4$ represents an aryl group having from 6 to 10 carbon atoms; said aryl groups is unsubstituted or is substituted by at least one substituent selected from the group consisting of substituents α, defined below; and
said substituents α are selected from the group consisting of alkyl groups having from 1 to 6 carbon atoms, hydroxy groups, halogen atoms, alkoxy groups having from 1 to 6 carbon atoms, haloalkoxy groups having from 1 to 6 carbon atoms, alkanoyl groups having from 1 to 6 carbon atoms, haloalkyl groups having from 1 to 6 carbon atoms, carbamoyl groups, cyano groups and aminosulfonyl groups.

8. A compound according to claim 1, wherein
A represents a phenylene.

9. A compound according to claim 1, wherein X represents NH, oxygen or sulfur.

10. A compound according to claim 1 selected from
2-[4-(3,5-dimethyl-4-phenyl-1H-pyrazol-1-yl)phenyl]ethyl (4methylphenyl)sulfonylcarbamate;
2-[4-(4-ethyl-3,5-dimethyl-1H-pyrazol-1-yl)phenyl]ethyl (4-methylphenyl)sulfonylcarbamate;
2-{4-[4-(4-fluorophenyl)-3,5-dimethyl-1H-pyrazol-1-yl] phenyl}ethyl (4-methylphenyl)sulfonylcarbamate;
2-{4-[3,5-dimethyl-4-(4-methylphenyl)-1H-pyrazol-1-yl] phenyl}ethyl (4-methylphenyl)sulfonylcarbamate;
N-[({2-[4-(3,5-dimethyl-4-phenyl-1H-pyrazol-1-yl)phenyl] ethyl}amino)carbonyl]-4-methylbenzenesulfonamide;
N-{[(2-{4-[4-(4-ethoxyphenyl)-3,5-dimethyl-1H-pyrazol-1-yl]phenyl}ethyl)amino]carbonyl}-4-methylbenzenesulfonamide;
N-{[(2-{4-[4-(3,5-difluorophenyl)-3,5-dimethyl-1H-pyrazol-1-yl]phenyl}ethyl)amino]carbonyl}-4-methylbenzenesulfonamide;
N-[({2-[4-(3,5-dimethyl-4-phenyl-1H-pyrazal-1-yl)phenyl] ethyl}amino)carbonyl]-4-(methyloxy) benzenesulfonamide;
N-[({2-[4-(3,5-dimethyl-4-phenyl-1H-pyrazol-1-yl)phenyl] ethyl}amino)carbonyl]-4-trifluoromethyl)oxy] benzenesulfonamide;
N-[({2-[4-(3,5-dimethyl-4-phenyl-1H-pyrazol-1-yl)phenyl] ethyl}amino)carbonyl]-2-methylbenzenesulfonamide;
N-[({2-[4-(3,5-dimethyl-4-phenyl-1H-pyrazol-1-yl)phenyl] ethyl}amino)carbonyl]-4-chlorobenzenesulfonamide;
N-[({2-[4-(3,5-dimethyl-phenyl-1H-pyrazol-1-yl)phenyl] ethyl}amino)carbonyl]-3-methylbenzenesulfonamide;
N-[({2-[4-(3,5-dimethyl-4-phenyl-1H-pyrazol-1-yl)phenyl] ethyl}amino)carbonyl]-2-fluorobenzenesulfonamide;
N-[({2-[4-(3,5-dimethyl-4-phenyl-1H-pyrazol-1-yl)phenyl] ethyl}amino)carbonyl]-3,4-dimethoxybenzesulfonamide;
N-[({2-[4-(3,5-dimethyl-4-phenyl-1H-pyrazol-1-yl)phenyl] ethyl}amino)carbonyl]-2,4-difluorobenzenesulfonamide;
N-[({2-[4-(3,5-dimethyl-4-phenyl-1H-pyrazol-1-yl)phenyl] ethyl}amino)carbonyl]-3,4-difluorobenzenesulfonamide;
2,4-difluoro-N-{[(2-{4-[5-methyl-4-phenyl-3-(trifluoromethyl)-1H-pyrazol-1-yl]phenyl}ethyl)amino] carbonyl}benzenesulfonamide;
2-fluoro-N-{[(2-{4-[5-methyl-4-phenyl-3-(trifluoromethyl)-1H-pyrazol-1-yl]phenyl}ethyl)amino] carbonyl}benzenesulfonamide;
2-{4-[3,5-dimethyl-4-(3-methylphenyl)-1H-pyrazol-1-yl] phenyl}ethyl (4methylphenyl)sulfonylcarbamate;
2-{4-[4-(3-methoxyphenyl)-3,5-dimethyl-1H-pyrazol-1-yl] phenyl}ethyl (4-methylphenyl)sulfonylcarbamate;
2-{4-[4-(3,4-dimethoxyphenyl)-3,5-dimethyl-1H-pyrazol-1-yl]phenyl}ethyl (4-methylphenyl)sulfonylcarbamate;
4-chloro-N-[({2-[4-(3-ethyl-5-methyl-4-phenyl-1H-pyrazol-1-yl)phenyl]ethyl}amino)carbonyl] benzenesulfonaimide; and
2-{4-[4-(4-ethoxyphenyl)-3,5-dimethyl-1H-pyrazol-1-yl] phenyl}ethyl (4-methylphenyl)sulfonylcarbamate.

11. A compound according to claim 1, selected from
2-[4-(3,5-dimethyl-4-phenyl-1H-pyrazol-1-yl)phenyl]ethyl (4-methylphenyl)sulfonylcarbamate;
N-[({2-[4-(3,5-dimethyl-4-phenyl-1H-pyrazol-1-yl)phenyl] ethyl}amino)carbonyl]-4-methylbenzenesulfonamide;
N-{[(2-{4-[4-4ethoxyphenyl)-3,5-dimethyl-1H-pyrazol-1-yl]phenyl}ethyl)amino]carbonyl}-4-methylbenzenesulfonamide;
N-[({2-[4-(3,5-dimethyl-4-phenyl-1H-pyrazol-1-yl)phenyl] ethyl}amino)carbonyl]-4-(methyloxy) benzenesulfonamide;
N-[({2-[4-(3,5-dimethyl-4-phenyl-1H-pyrazol-1-yl)phenyl] ethyl}amino)carbonyl]-3,4-dimethoxybenzenesulfonamide;
2,4-difluoro-N-{[(2-{4-[5-methyl-4-phenyl-3-(trifluoromethyl)-1H-pyrazol-1-yl]phenyl}ethyl)amino] carbonyl}benzenesulfonamide; and
2-fluoro-N-{[(2-{4-[5-methyl-4-phenyl-3-(trifluoromethyl)-1H-pyrazol-1-yl]phenyl}ethyl)amino] carbonyl}benzenesulfonamide.

12. A pharmaceutical composition for the treatment of a disorder or condition mediated by prostaglandin in a mammal comprising an effective amount of a compound according to claim 1 and a pharmaceutically acceptable diluent or carrier.

13. A pharmaceutical composition according to claim 12 where the disease condition is selected from the group consisting of pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures, bone fracture, immune and autoimmune diseases; cellular neoplastic transformations or metastic tumor growth; diabetic retinopathy, tumor angiogenesis; prostanoid-induced smooth muscle contraction associated with dysmenorrhea, premature labor, allergic rhinitis, atopic dermatitis, asthma or eosinophil related disorders, hyperimmunoglobulinaemia, Castleman's disease, myeloma; Alzheimer's disease, sleep disorders, endocrine disturbance; glaucoma bone loss; osteoporosis; promotion of bone formation; Paget's disease: cytoprotection in peptic ulcers, gastritis, regional enteritis, ulcerative colitis, diverticulitis or other gastrointestinal lesions; GI bleeding and patients undergoing chemotherapy; coagulation disorders selected from hypoprothrombinemia; hemophilia and other bleeding problems; kidney disease; thrombosis; occlusive vascular disease; presurgery and anti-coagulation.

\* \* \* \* \*